(12) United States Patent
Saitoh et al.

(10) Patent No.: US 10,603,506 B2
(45) Date of Patent: Mar. 31, 2020

(54) COIL APPARATUS FOR USE IN TRANSCRANIAL MAGNETIC STIMULATION APPARATUS FOR INCREASING CURRENT GENERATED BY INDUCED ELECTRIC FIELD

(71) Applicants: The University of Tokyo, Tokyo (JP); OSAKA UNIVERSITY, Suita-shi, Osaka (JP)

(72) Inventors: Youichi Saitoh, Ikeda (JP); Masaki Sekino, Tokyo (JP); Yu Miyawaki, Tokyo (JP); Keita Yamamoto, Tokyo (JP)

(73) Assignees: THE UNIVERSITY OF TOKYO, Tokyo (JP); OSAKA UNIVERSITY, Osaka (JP)

( * ) Notice: Subject to any disclaimer, the term of this patent is extended or adjusted under 35 U.S.C. 154(b) by 249 days.

(21) Appl. No.: 15/563,705

(22) PCT Filed: Apr. 1, 2016

(86) PCT No.: PCT/JP2016/060965
§ 371 (c)(1),
(2) Date: Oct. 2, 2017

(87) PCT Pub. No.: WO2016/159371
PCT Pub. Date: Oct. 6, 2016

(65) Prior Publication Data
US 2018/0071545 A1 Mar. 15, 2018

Related U.S. Application Data

(60) Provisional application No. 62/259,768, filed on Nov. 25, 2015, provisional application No. 62/166,860, (Continued)

(51) Int. Cl.
*A61N 1/00* (2006.01)
*A61N 2/02* (2006.01)
(Continued)

(52) U.S. Cl.
CPC .............. *A61N 2/02* (2013.01); *A61N 1/40* (2013.01); *A61N 2/006* (2013.01); *A61N 2/008* (2013.01)

(58) Field of Classification Search
CPC . A61N 2/02; A61N 2/00; A61N 2/004; A61N 2/006; A61N 2/008
(Continued)

(56) References Cited

U.S. PATENT DOCUMENTS 8,740,765 B1 6/2014 Fischell et al.
2006/0287566 A1 12/2006 Zangen et al.
(Continued)

FOREIGN PATENT DOCUMENTS

GB 2 360 213 A 9/2001
JP 5-59920 U 8/1993
(Continued)

OTHER PUBLICATIONS

Communication dated Nov. 2, 2018, from the European Patent Office in counterpart European Application No. 16773251.0.
(Continued)

*Primary Examiner* — John P Lacyk
(74) *Attorney, Agent, or Firm* — Sughrue Mion, PLLC

(57) ABSTRACT

A coil apparatus for use in a transcranial magnetic stimulation apparatus is provided in which the coil apparatus includes a coil arranged to oppose a surface of a head of a human to generate a current by an induced electric field in a magnetic stimulation-target region in a brain by electromagnetic induction, and to stimulate neurons. The coil apparatus includes the coil configured by winding a con-
(Continued)

ductive wire along a predetermined reference surface; and a magnetic body arranged between the head and the coil to oppose the coil, and arranged at a position at an opposite side of the head. The magnetic body is provided for flowing a current therein by an induced electric field when the coil is driven, and for increasing the current flowing by the induced electric field in a magnetic stimulation-target region of the brain as compared with that with no magnetic body.

13 Claims, 44 Drawing Sheets

Related U.S. Application Data filed on May 27, 2015, provisional application No. 62/142,610, filed on Apr. 3, 2015.

(51) Int. Cl.
*A61N 1/40* (2006.01)
*A61N 2/00* (2006.01)

(58) Field of Classification Search
USPC ...................................................... 600/9–15
See application file for complete search history.

(56) References Cited

U.S. PATENT DOCUMENTS

| | | |
|---|---|---|
| 2011/0046432 A1 | 2/2011 | Simon et al. |
| 2012/0157752 A1 | 6/2012 | Nishikawa et al. |
| 2014/0357935 A1 | 12/2014 | Ilmoniemi et al. |
| 2015/0018667 A1 | 1/2015 | Radman et al. |
| 2016/0346562 A1 | 12/2016 | Saitoh et al. |

FOREIGN PATENT DOCUMENTS

| | | |
|---|---|---|
| JP | 2012-125546 A | 7/2012 |
| JP | 2014-155867 A | 8/2014 |
| WO | 2010/147064 A1 | 12/2010 |
| WO | 2015/109000 A1 | 7/2015 |
| WO | 2015/122506 A1 | 8/2015 |

OTHER PUBLICATIONS

Keita Yamamoto, et al., "Characteristics of bowl-shaped coils for transcranial magnetic stimulation", Journal of Applied Physics, Mar. 17, 2015, pp. 17A318-1 to 17A318-4, vol. 117, Issue 17.
International Search Report for PCT/JP2016/060965 dated May 17, 2016 [PCT/ISA/210].
International Preliminary Report on Patentability with translation of Written Opinion dated Oct. 12, 2017, issued by the International Searching Authority in application No. PCT/JP2016/060965.

Fig.43B
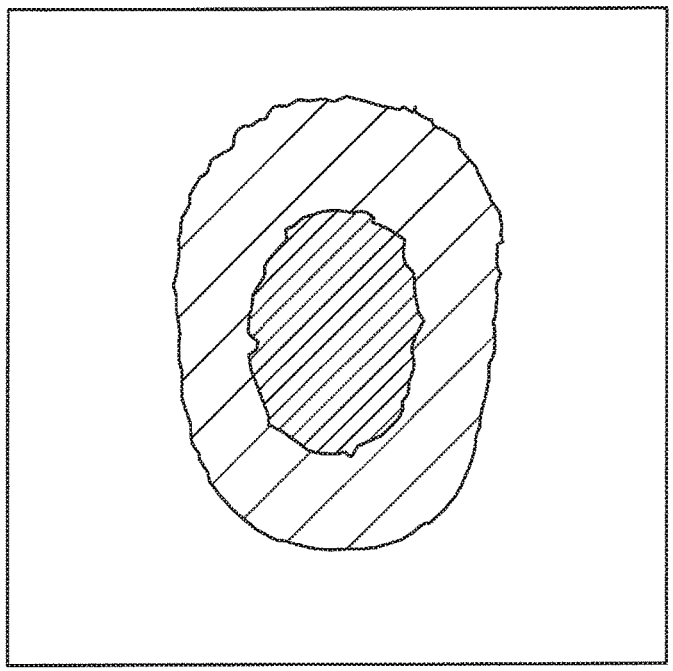
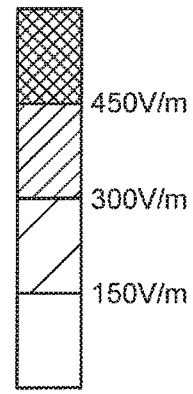
Fig.43C
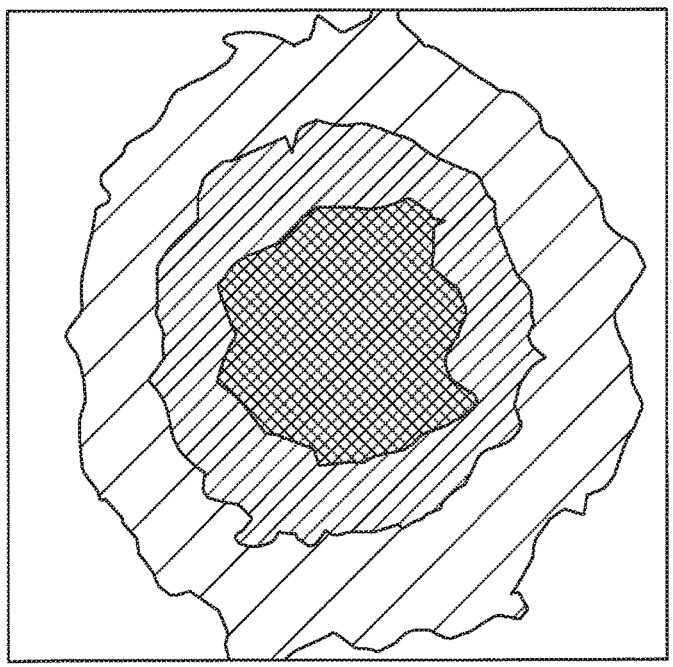
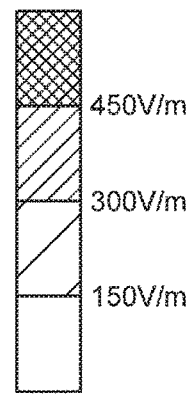

{ → INDUCED ELECTRIC FIELDS GENERATED BY ECCENTRIC FIGURE-EIGHT-SHAPED COIL
⇒ INDUCED ELECTRIC FIELDS GENERATED BY INDUCED CURRENTS IN IRON CORE

{ → INDUCED ELECTRIC FIELDS GENERATED BY ECCENTRIC FIGURE-EIGHT-SHAPED COIL
⇒ INDUCED ELECTRIC FIELDS GENERATED BY INDUCED CURRENTS IN IRON CORE

- 22 — MAGNETIC BODY OF IRON CORE
- 91 — MAGNETIC SHIELD OF Ni-Zn FERRITE
- 91F — FLANGE OF Ni-Zn FERRITE

Fig.63A 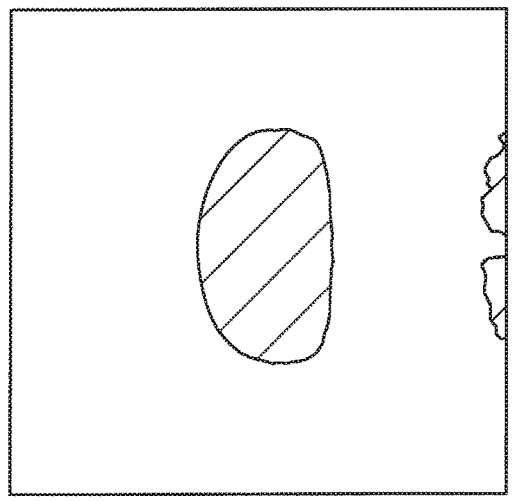 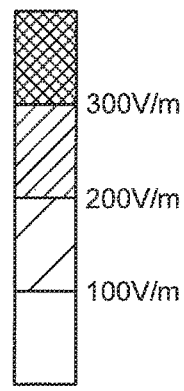
Fig.63B 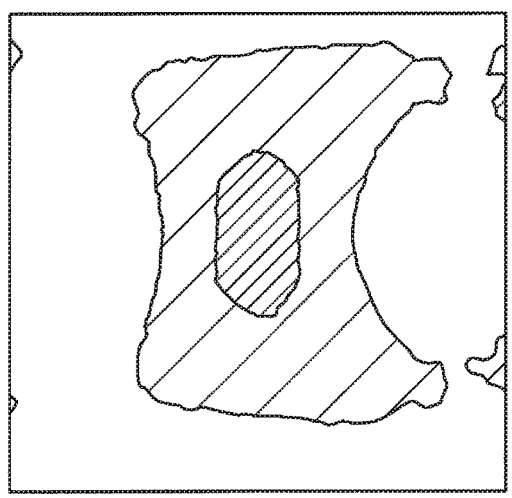 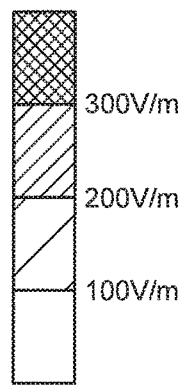
Fig.63C 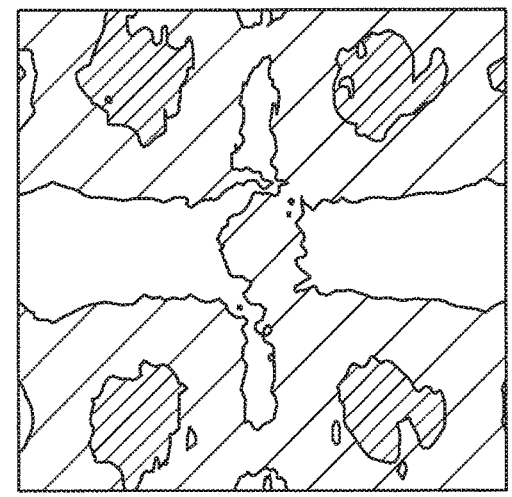 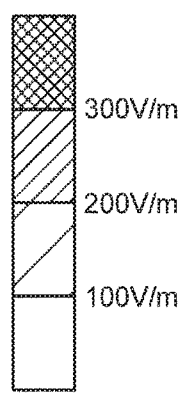

COIL APPARATUS FOR USE IN TRANSCRANIAL MAGNETIC STIMULATION APPARATUS FOR INCREASING CURRENT GENERATED BY INDUCED ELECTRIC FIELD

CROSS REFERENCE TO RELATED APPLICATIONS

This application is a National Stage of International Application No. PCT/JP2016/060965, filed on Apr. 1, 2016, which claims priority from U.S. Patent Provisional Application No. 62/259,768, filed on Nov. 25, 2015, U.S. Patent Provisional Application No. 62/166,860, filed on May 27, 2015, and U.S. Patent Provisional Application No. 62/142,610, filed on Apr. 3, 2015, the contents of all of which are incorporated herein by reference in their entirety.

TECHNICAL FIELD

The present invention relates to a coil apparatus for use in a transcranial magnetic stimulation apparatus, and to a transcranial magnetic stimulation apparatus provided with the above described coil apparatus.

BACKGROUND ART

1.1 Prior Art

Recently, the number of the patients of lifestyle diseases such as stroke is increasing. One of the after effects of the lifestyle diseases is a neuropathic pain. The neuropathic pain is a pain in a hand, leg, or foot caused by nerves damaged for some reason.

Normally, medication is the first to be selected as a treatment method of the neuropathic pain. However, medication has a small treatment target range and is not effective to all patients. Under such circumstances, a method of directly electrically stimulating the primary motor cortex of the cerebrum by using electrodes embedded in the head has been proposed. However, the electrical stimulation treatment using the embedded electrodes requires a craniotomy. Therefore, this treatment has such a problem that the burdens on patients are extremely heavy.

Therefore, Saito, et al. of Osaka University have carried out extensive studies, proposed a transcranial magnetic stimulation method of non-invasively stimulating the primary motor cortex of the cerebrum without using embedded electrodes (specifically, a method of stimulating the brain with pulse magnetic fields generated by flowing an alternating current in a coil), and elucidated that the transcranial magnetic stimulation method can improve neuropathic pains after strokes. However, although the transcranial magnetic stimulation method is advantageous in the point that this method does not require craniotomy, the patient of this method has to take magnetic stimulation treatment every day since the treatment effects thereof last only about one day.

1.2 Transcranial Magnetic Stimulation Method

Transcranial magnetic stimulation is a method of generating a pulse magnetic field from a coil incorporated in a coil apparatus placed on the surface of the head and magnetically stimulating the brain with the electric field induced in the brain by the pulse magnetic fields. In order to carry out this, the coil connects to a drive circuit. According to the present drive circuit, in order to generate an instantaneous current in the coil, electric charge from a power supply apparatus (including an alternating-current power supply, a power supply circuit, and a voltage booster circuit.) accumulates in a capacitor. Then, when a thyristor is turned on, a current flows in the stimulation coil. After the current flows in the resonance circuit of the stimulation coil and the capacitor through a diode, the thyristor is turned off. As a result, the current corresponding to one cycle of a sine wave flows in the stimulation coil. When the above described operation is repeated, an alternating current having a constant cycle is applied to the coil to generate a variable magnetic field, an eddy current in the opposite direction of the coil current is induced in the brain because of the influence of the variable magnetic field, and stimulating neurons with the eddy current generates an action voltage potential.

As a result of magnetically stimulating the primary motor cortex of the brain in this manner, influence appears in the body part corresponding to the stimulated part. For example, when the primary motor cortex connected to the nerves of a hand or a foot is magnetically stimulated, the nerves of the hand or foot are stimulated, and a corresponding part moves. This is conceivably for the reason that the current flowing in the coil induces the current in the opposite direction thereof in the brain, the induced current stimulates interneurons and, further, corticospinal neurons, and the part of the body corresponding to the stimulated brain part moves.

An advantageous point of the magnetic stimulation is extremely low invasiveness. Specifically, the magnetic field reaches the interior of the brain without being affected by living tissues. Therefore, the magnetic stimulation does not stimulate the scalp having algesiroreceptors, almost at all, and there is almost no pain caused by the stimulation.

Historically, the magnetic stimulation for humans was first reported in 1985, and then, has been clinically applied in diagnoses of neural diseases. In addition, there have been reports that repeatedly applying transcranial magnetic stimulations to the patients having various neural diseases or mental illness improves the symptoms thereof, and, recently, applications thereof to treatment are advancing. For example, in relation to the treatment of depression, it has been found out that stimulation to the prefrontal area was effective, and U.S. Food and Drug Administration approved the magnetic stimulation treatment for medication-resistant depression in 2008. Also in relation to the treatment of Parkinson's syndromes, many clinical researches have been carried out, and the findings that indicate the effectiveness of magnetic stimulation have been accumulated. As described above, the magnetic stimulation treatment exerts pain-removing effects also for neuropathic pains. Therefore, today, in Japan, magnetic stimulation treatment is carried out for the patients of various neural diseases in well-equipped medical institutions.

However, a conventional magnetic stimulation apparatus has a weight of about 70 Kg and, in addition, requires electric construction for installation. Therefore, the conventional medical stimulation apparatus can be used only in well-equipped medical institutions. In addition, since a stimulation position is determined with reference to MRI data of a patient in actual treatment, treatment by a skilled healthcare worker is required. Therefore, in reality, only the treatment by professionals of medication institutions is carried out, and patients have to visit the medical institutions every day in order to continuously obtain the pain-removing effects. Therefore, in order to reduce the burden on the patients, development of a home magnetic stimulation treatment apparatus which can be used only by the operations by a non-healthcare worker is demanded.

1.3 Transcranial Magnetic Stimulation Apparatus

Today, in medical practice, various transcranial magnetic stimulation apparatuses are introduced and used. These magnetic stimulation apparatuses are built on the assumption that the apparatuses are operated by healthcare workers such as doctors, and the parts to be stimulated are determined by doctors. As an example of specific treatment, in treatment of a neuropathic pain, a vicinity of the primary motor cortex of the brain of a patient is stimulated to confirm a spasm phenomenon called twitch in which his fingers moves, the position of the brain at which the twitch has been confirmed is set to a stimulation point, and the current that is 90% of the stimulation intensity at which the twitch can be confirmed is applied to the coil in treatment. When the stimulation position in the brain is shifted even by several millimeters, the part different from an aimed stimulation part is stimulated. Therefore, it is important to install the coil precisely at the aimed part so as to apply the stimulation having an appropriate intensity to the aimed stimulation part.

However, in many cases, the patients of neuropathic pains have extremely low Quality of Life (QOL) due to the pains in the hand, leg, and/or foot. In addition, it has been reported that the pain-removing effects brought about by the transcranial magnetic stimulation lasts only for about one day. Therefore, a safe, low cost, and small home magnetic stimulation treatment apparatus that is capable of appropriately and easily adjusting the position of a coil onto a stimulation part is desired.

1.4 Conventional Stimulation-Position Adjusting System for Use in Transcranial Magnetic Stimulation As described above, in transcranial magnetic stimulation, it is important to precisely stimulate an aimed brain part. In order to do that, various position adjusting systems have been developed. For example, a position adjusting system using an infrared camera has been proposed. According to this system, images of a plurality of marks on the head (brain) and a stimulation coil are taken with an accompanying optical camera, and the positional relations of the head (brain) and the coil are displayed by a monitor screen. In addition, when MRI image data of the patient and the image of the camera are combined, the relative positions of the coil and the brain can be precisely perceived, and more precise position adjustment can be carried out. In practice, misalignment errors somewhat vary, but are approximately about several millimeters. However, there are problems that the size of the system is large, in addition, the system cannot be handled by those who are not healthcare workers, and, further, the cost thereof is high.

1.5 Conventional Stimulation Coil for Use in Transcranial Magnetic Stimulation As described above, a home magnetic stimulation apparatus is desired to be compact. On the other hand, the size of an electric-power supplying part is inversely proportional to the stimulation efficiency of a coil. Therefore, the higher the stimulation efficiency becomes, the lower the electric-power supply amount required becomes. In this case, the lower the number of circuit components becomes, the apparatus becomes smaller and more inexpensive. Therefore, various stimulation coils capable of more efficiently applying stimulation have been developed. In addition, since the transcranial magnetic stimulation has different treatment effects depending on the stimulation characteristics thereof, various coils having various stimulation characteristics have been developed.

For example, in 1985, a circular coil having a characteristic that the coil is capable of strongly stimulating the part immediately below the center of the circular coil was developed. In addition, in 1988, a figure-eight-shaped coil was developed [Reference Documents 1, 2].

(a) Circular Coil

A circular coil is commercially provided by MagVenture of U.S.A. This circular coil is, for example, a single spiral coil, which is a single conductive wire (conductor) bent spirally along the Archimedes spiral, incorporated in a casing. The circular coil has such an advantageous effect that the stimulation can be carried out in a wide range and, on the other hand, has a disadvantage that stimulation efficiency is bad. The stimulation intensity of the part at the center of the coil is almost zero. Therefore, it is conceived that the circular coil is not appropriate for use in tests or treatment in which a narrow part is locally stimulated.

(b) Figure-Eight-Shaped Coil

A figure-eight-shaped coil has been developed by Magstim of U.S.A. This figure-eight-shaped coil is obtained by incorporating a figure-eight-shaped spiral coil, which is obtained by bending a single conductive wire (conductor) and has two spiral coil parts, in a casing.

In the operation, a current flows in one of the circular coils in a clockwise direction, and a current flows in the other circular coil counterclockwise. By virtue of this, the part corresponding to a central part of both of the circular coils can be strongly stimulated. As compared with the above described circular coil, high stimulation efficiency can be obtained since the local stimulation can be carried out. However, there is such a problem that robustness (the property of the capability of generating eddy currents in wider range and the capability of effectively applying magnetic stimulation even with slight misalignment) is low. Generally speaking, the figure-eight-shaped coil has such an advantageous effect that the brain can be stimulated with high resolution since the spatial resolution thereof is within 5 mm.

(c) H-Coil

In 2005, an H-coil has been proposed by Zangen, et al. The H-coil has such an advantageous effect that a deep part of the brain can be stimulated by the current which flows in the parts having directional components perpendicular to the brain. For example, the stimulation can reach the depth that is about 2.5 times compared with that of the figure-eight-shaped coil. However, the H-coil has a problem of bad stimulation efficiency. Therefore, the H-coil is conceived to be effective in the treatment of depression, etc. that requires stimulation of the dorsolateral prefrontal area in a deep part. In addition, the H-coil has such a characteristic that attenuation of induced electric fields is small when the deep part is stimulated. Therefore, the H-coil has such an advantageous effect that, in magnetic stimulation, a patient does not easily feel an instantaneous pain.

PRIOR ART DOCUMENTS

Patent Documents

[Patent Document 1] Japanese Patent Laid-open Publication No. JP2012-125546A
[Patent Document 2] International Publication No. WO2010/147064A1

[Patent Document 3] International Publication No. WO2015/122506A1

SUMMARY OF THE INVENTION

Problems to be Solved by the Invention

1.6 Research Trends about Position Adjusting System for Use in Transcranial Magnetic Stimulation As described above, the conventional position adjusting system is not appropriate as a home apparatus since the conventional position adjusting system uses expensive equipment and requires operation by a doctor. In order to solve this problem, Nishikawa, et al. of Osaka University developed a data-set-type magnetic-field navigation system, which can be more easily operated [Reference Document 3]. The data set referred to in this case is a combination of the intensities of magnetic fields emitted from permanent magnets attached to a stimulation coil and a three-dimensional position of the stimulation coil. The intensity of the magnetic field is measured by a plurality of magnetic sensors. In this method, first, an eyeglass-type fixer with the magnetic sensors is attached to a patient in a hospital. The magnetic force emitted from the plurality of permanent magnets attached to the coil is detected by the magnetic sensors in order to attach the eyeglass-type fixer to the same position. In addition, a doctor specifies an optimum stimulation position, and the optimum stimulation position and the three-dimensional position of the coil corresponding thereto are acquired in advance. When the patient himself/herself performs position adjustment of the coil, the patient uses the data set obtained in advance, determines how to move the eyeglass-type fixer to move the fixer to the optimum stimulation position while watching a monitor, and carries out operation. A misalignment error when a healthy man in his twenties used this system was about 5 mm.

1.7 Research Trends about High-Efficiency Stimulation Coil for Use in Transcranial Magnetic Stimulation As described above, it is important for a home magnetic stimulation apparatus to be compact. For this, a highly-efficient stimulation coil is demanded. The coils developed in the past have various stimulation characteristics, but are required to improve efficiency for home use. In addition, the apparatuses are on the assumption that, for example, they are to be operated by doctors, and the coils capable of carrying out stimulation in a wide range and having high robustness have not yet been developed.

1.7.1 Modified Figure-Eight-Shaped Coil

Today, various modified figure-eight-shaped coils are used [Reference Documents 4 to 15]. These modified figure-eight-shaped coils are categorized into a type in which two spiral coil parts are partially overlapped (overlapping type: see FIG. 11) and a type in which two spiral coil parts are disposed in parallel without overlapping (non-overlapping type: See FIG. 3). In addition, the figure-eight-shaped spiral coils are categorized into an Archimedes type in which two spiral coil parts are bent along the Archimedes spiral (non-eccentric type) and a type developed by Sekino, et al. in 2000, in which the respective centers of two spiral coil parts are made to be eccentric toward the other spiral coil part (eccentric type). Among these, the eccentric-type figure-eight-shaped spiral coil has the structure in which the center of a circular coil is close to the other circular coil, and conductive wires are densely disposed at a central part of the figure-eight-shaped coil. Therefore, since eddy currents can be concentrated immediately below the central part by flowing currents in the opposite directions to the coil parts at which the two spiral coil parts are close to each other or to the overlapped coil parts, there is such a feature that local stimulation having better efficiency than that of the non-eccentric figure-eight-shaped coil is obtained. However, also regarding the modified figure-eight-shaped coil, there is a room for improvement in robustness.

Other than that, some modified figure-eight-shaped coils are proposed, but do not have drastic differences in basic performance. For example, Magstim 70 mm (P/N 9790) developed by Magstim located in Spring Gardens, Whitland, Carmarthenshire SA34 0HR, UK is a general figure-eight-shaped coil. In addition, the Medtronic-Dantec MCB70 double coils developed by Magpro located in Lucerne-marken 15, DK-3520, Farum, Denmark have patient-opposing surfaces of circular coil parts in both sides that are bent to fit the brain. Regarding these figure-eight-shaped coils, according to the results of comparison analysis carried out by Axel Thielscher, et al. [Reference Document 16], Medtronic was advantageous by 19% in terms of stimulation efficiency. In terms of stimulation ranges, there was almost no difference between both of the figure-eight-shaped coils. The areas that can be stimulated with a stimulation intensity of 50% of the maximum stimulation intensity are compared, and then, it was confirmed that Medtronic was capable of stimulating the area in a wider range by 16%. As shown in above results, a plurality of modified figure-eight-shaped coils is provided, but there is no large improvement in terms of stimulation efficiency and stimulation robustness. In addition, commercially-available coils have a problem that the influence of the magnetic fields generated by the coils is not taken into consideration almost at all [Reference Documents 17 and 18].

1.7.2 Coil Using Iron Core

In order to improve stimulation characteristics, many methods have been proposed other than the methods of changing coil shapes, etc. For example, in 2003, B. H. Han, et al. proposed to improve stimulation efficiency by attaching an iron core of a ferromagnetic body to a circular coil [Reference Documents 19 to 21]. For example, in a model in which, above a circular coil, a laminated iron core having approximately the same size as that was disposed, the stimulation intensity thereof was confirmed to improve at most by 50 to 60% compared with a model with no iron core. According to this method, compared with the previous method, stimulation efficiency improvement was improved by about 3 times. However, regarding figure-eight-shaped spiral coils, practical uses thereof as clinical trial devices are considered, but researches about the shape/disposition of iron cores for improving the stimulation characteristics thereof have not yet been carried out.

There is a case in which analysis of stimulation efficiency has been carried out for a model in which an iron core is attached not only to a circular coil, but also to an H-coil which generates induced currents perpendicular to the brain [Reference Document 22]. For example, according to reports by R. Salvador, et al., in the case of the model in which the iron core was attached to the H-coil, the induced electric field intensity on the surface of the brain was confirmed to increase by 50% as compared with a model without an iron core. Appropriate iron-core shapes are different depending on the shapes of stimulation coils. However, at present, the iron-core shape effective only for circular coils has been studied. In addition, the effects of iron cores for the eccentric figure-eight-shaped coils, which have been already used in the transcranial magnetic stimulation method, have not been verified.

1.7.3 Dome-Shaped Coil

In order to facilitate the position adjustment of a magnetic stimulation system, Patent Document 3 proposes a coil having higher stimulation robustness. An analysis model of the coil proposed in the Patent Document has the following parameters:

the number of turns of a conductive wire is 20;
the upper sphere radius of the conductive wire is 56 mm; and
the lower sphere radius of the conductive wire is 100 mm.

A current (pulsating current) of 5.28 kA with a pulse width of 298 μs was applied to this model, and an induced current density on the surface of a semispherical brain model (electric conductivity: 0.1065 S/m) was analyzed. As a result, compared with the conventional figure-eight-shaped coil, improvement in stimulation robustness was confirmed. However, further improvement in stimulation efficiency is desired.

It is an object of the present invention to provide a coil apparatus that is capable of generating a higher induced electric field intensity onto a magnetic stimulation-target region (this means a region to be magnetically stimulated) of the brain, than that of the conventional techniques, has more robustness than that of the conventional techniques, and can be used in, for example, a home magnetic stimulation apparatus and to provide a transcranial magnetic stimulation apparatus provided with the coil apparatus.

Means for Dissolving the Problems

According to one aspect of the present invention, there is provided a coil apparatus for use in a transcranial magnetic stimulation apparatus, where the coil apparatus includes a coil arranged to oppose a surface of a head of a human to generate a current by an induced electric field in a magnetic stimulation-target region in a brain by electromagnetic induction, and to stimulate neurons. The coil apparatus includes the coil configured by winding a conductive wire along a predetermined reference surface; and a magnetic body arranged between the head and the coil to oppose the coil, and arranged at a position at an opposite side of the head. The magnetic body is provided for flowing a current therein by an induced electric field when the coil is driven, and for increasing the current flowing by the induced electric field in a magnetic stimulation-target region of the brain as compared with that with no magnetic body.

Effect of the Invention

Therefore, according to the present invention, the present invention is capable of generating a higher induced electric field intensity onto the magnetic stimulation-target region of the brain, than that of the conventional techniques, having more robustness than that of the conventional techniques, and being used, for example, in a home magnetic stimulation apparatus.

BRIEF DESCRIPTION OF THE DRAWINGS

FIG. 43B is a contour graph showing induced electric field intensities of a brain model surface.

FIG. 43C is a contour graph showing induced electric field intensities of a brain model surface.

FIG. 63A is a contour graph showing an induced electric field generated at an electric conductor surface.

FIG. 63B is a contour graph showing an induced electric field generated at an electric conductor surface.

FIG. 63C is a contour graph showing an induced electric field generated at an electric conductor surface.

MODES FOR CARRYING OUT THE INVENTION

Embodiments According to the Present Invention

Figure 1:
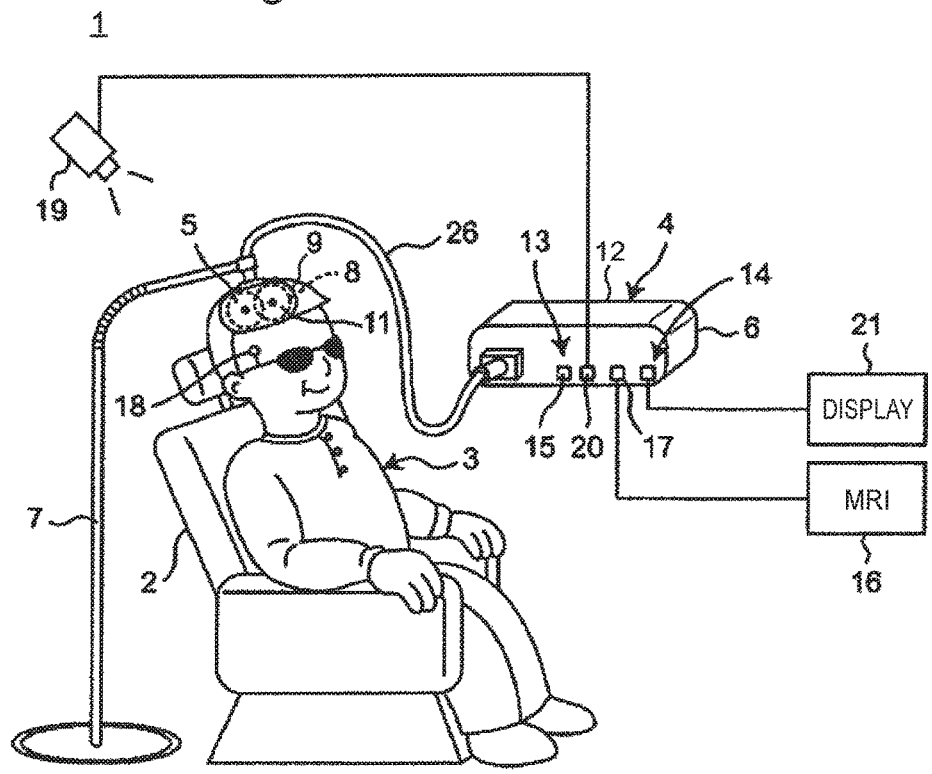
FIG. 1 is a perspective view showing a brief configuration of a transcranial magnetic stimulation apparatus according to an embodiment of the present invention.

Hereinafter, various embodiments according to the present invention will be described with reference to drawings. It is noted that, in the following embodiments, similar constituent elements are denoted by the same reference signs.

In the present embodiment, in order to provide a coil apparatus and a transcranial magnetic stimulation apparatus having the coil apparatus, which are capable of (a) generating a higher induced electric field intensity in a magnetic stimulation-target region of the brain of a human, than that of conventional techniques, (b) having more robustness than that of the conventional techniques, and (c) being used in, for example, a home magnetic stimulation apparatus, the present inventors carried out those described below and obtained knowledge.

(1) Eccentric figure-eight-shaped coils and dome-shaped coils were provided with various magnetic bodies (iron cores), induced electric field intensities on a brain model surface were obtained by numerical analysis for each of the combinations of the coils and the magnetic bodies, and then, the model of the magnetic body capable of carrying out magnetic stimulation with the highest efficiency was determined.

(2) For each of the combinations, stimulation robustness was evaluated based on the results of the numerical analysis, and the correlations between the shapes of the magnetic bodies and the stimulation robustness were summarized.

(3) The model for providing the eccentric figure-eight-shaped coil with a ferrite member in order to suppress leak magnetic fields was determined by numerical analysis, where the model minimizes the distance (the distance from the coil) for satisfying the magnetic-field safety standard (21 A/m) of the International Commission on Non-Ionizing Radiation Protection (ICNIRP).

Based on the knowledge based on the analysis results, which will be described later in detail, the present embodiment provides a new coil apparatus for use in a transcranial magnetic stimulation apparatus and a transcranial magnetic stimulation apparatus having the coil apparatus.

Specifically, a coil apparatus for use in a transcranial magnetic stimulation apparatus according to an aspect of the present invention has a coil including a conductive wire wound in a spiral shape along a reference surface and has a magnetic body disposed above the coil and along the coil. In this case, the reference surface may be a plane, a curved surface, or a spherical surface. More specifically, the coil apparatus for use in the transcranial magnetic stimulation apparatus according to the embodiment is provided. In this case, the coil apparatus includes a coil arranged to oppose a surface of a head of a human to generate a current by an induced electric field in a magnetic stimulation-target region in a brain by electromagnetic induction, and to stimulate neurons. The coil apparatus includes a coil configured by winding a conductive wire along a predetermined reference surface; and a magnetic body arranged between the head and the coil to oppose the coil, and arranged at a position at an opposite side of the head. The coil apparatus is characterized in that the magnetic body is provided for flowing a current therein by an induced electric field when the coil is driven, and for increasing the current flowing by the induced electric field in a magnetic stimulation-target region of the brain as compared with that with no magnetic body.

In addition, the coil may be any one of a non-eccentric spiral coil, an eccentric spiral coil, and a dome-shaped coil. Alternatively, the coil may be one of a non-eccentric figure-eight-shaped spiral coil, and an eccentric figure-eight-shaped spiral coil having two spiral coil parts.

Further, when a direction of a line connecting centers of the two spiral coil parts along the reference surface is defined as an X direction, and when a direction orthogonal to the X direction along the reference surface is defined as a Y direction, then the magnetic body may be configured by laminating a plurality of magnetic steel sheets in the X direction.

Furthermore, when a direction of a line connecting centers of the two spiral coil parts along the reference surface is defined as an X direction, and when a direction orthogonal to the X direction along the plane is defined as a Y direction, then the magnetic body may be configured by laminating a plurality of magnetic steel sheets in the Y direction.

Furthermore, when a direction of a line connecting centers of the two spiral coil parts along the reference surface is defined as an X direction, and when a direction orthogonal to the X direction along the plane is defined as a Y direction, then the magnetic body may include a first laminated magnetic body configured by laminating a plurality of magnetic steel sheets in the X direction; and a second laminated magnetic body configured by laminating a plurality of magnetic steel sheets in the Y direction.

In this case, the magnetic body may be configured by laminating in the winding direction of the coil. In other words, individual laminated plates of the magnetic body may be laminated and configured in the direction in which respective turn winding wires of the coil are laminated.

In addition, in the X direction, the second laminated magnetic body part may be disposed at the center of the coil apparatus, and the first laminated magnetic body parts may be disposed in both sides of the second laminated magnetic body part.

In another aspect of the present invention, when seen from a Z direction orthogonal to the X direction and the Y direction, the magnetic body may have a tetragonal shape, a polygonal shape, a circular shape, an elliptical shape, or an oblong shape.

In another aspect of the present invention, the magnetic body may have an opening at a center when seen from the Z direction orthogonal to the X direction and the Y direction.

The coil apparatus for use in the transcranial magnetic stimulation apparatus according to an embodiment includes a figure-eight-shaped coil having two spiral coil parts of a conductive wire wound in a spiral shape, and includes a magnetic body disposed above the coil and along the coil. In this case, the magnetic body is configured by laminating a plurality of magnetic steel sheets in the disposing direction of the conductive wire in a central part of the coil.

The coil apparatus for use in the transcranial magnetic stimulation apparatus according to another aspect of the present invention includes a figure-eight-shaped coil having two spiral coil parts of a conductive wire wound in a spiral shape; and includes a magnetic body disposed above the coil and along the coil. In this case, the magnetic body is configured by laminating a plurality of magnetic steel sheets in the direction orthogonal to the direction connecting the centers of the two spiral coil parts.

The transcranial magnetic stimulation apparatus according to the embodiments may include any one of the above described coil apparatuses.

First Embodiment

Referring to FIG. 1, a transcranial magnetic stimulation apparatus 1 includes a magnetic stimulation apparatus 4, which is supported by an unshown support mechanism (for example, a chair 2 or a bed) and applies magnetic stimulation to, for example, a magnetic stimulation-target region of the brain of a patient 3. The magnetic stimulation apparatus 4 includes a coil apparatus 5, and a control unit 6 for generating dynamic magnetic fields for applying the magnetic stimulation to the brain of the patient 3.

Referring to FIG. 1, the coil apparatus 5 is preferably supported by an appropriate positioning unit 7 so that the coil apparatus 5 can freely move along the surface of the head of the patient 3, and can be positioned at an arbitrary position. The coil apparatus 5 includes a coil 8, and a casing 9 made of an electric insulating material surrounding the coil 8. The casing 9 includes a holder 10, which is integrally formed with the casing 9, and is retained by the positioning unit 7 via the holder 10. In the embodiment, the coil 8 is a figure-eight-shaped coil. The figure-eight-shaped coil may be either one of overlapping type in which two spiral coil parts are partially overlapped with each other, and non-overlapping type in which two spiral coil parts are disposed in parallel without being overlapped with each other. In addition, the figure-eight-shaped coil may be either one of non-eccentric type in which the two spiral coil parts are bent along the Archimedes spiral; and eccentric type in which the center of each of the two spiral coil parts is moved toward another coil part.

The casing 9 integrally includes three or more observation targets (for example, a mark 11 or a target such as a projection). These observation targets are used for obtaining the relative position and direction of the coil 8 with respect to the head of the patient.

In addition, the transcranial magnetic stimulation apparatus 1 may be configured, for example, in the following manner.

The control unit 6 includes a box-shaped housing 12. The housing 12 has an input part 13, and an output part 14. The input part 13 includes:

a drive-condition setting part 15, which sets drive conditions (for example, the voltage, current, and frequency to be applied to the coil 8) of the transcranial magnetic stimulation apparatus 1;

a data receiving part 17, which receives tomographic image data of human body (in particular, a head) generated by a tomographic-image taking apparatus (for example, MRI, CT, PET) 16; and a data receiving part 20, which receives image data from a stereoscopic-image-taking optical 3-dimensional-position sensing camera (hereinafter, simply referred to as "a camera") 19, which simultaneously take images of the mark 11 provided on the casing 9 of the coil apparatus 5, and three or more observation targets (for example, a mark 18 or a projection) provided on a worn item (for example, eyeglasses) such as eyeglasses worn by the patient 3 or on the skin of the patient 3. Although not shown in the drawing, the camera 19 is attached to the positioning unit 7 or to a fixed part of a room housing the transcranial magnetic stimulation apparatus 1.

The above described tomographic-image taking apparatus 16, the data receiving part 17, the stereoscopic-image-taking optical three-dimensional-position sensing camera 19, the data receiving part 20, etc. are one implementation aspect used for carrying out positioning of the coil apparatus 5 onto a head irradiation part, and another aspect may be used.

In the present embodiment, it should be understood that the current applied to the coil includes not only the current that cyclically changes the directions of flow as time elapses (alternating current), but also the current that has a constant direction of flow and cyclically varies amplitude (so-called "pulsating current").

The output part 14 connects to a display 21 such as a liquid-crystal display apparatus or to a computer having a display (not shown) and is configured to be able to output the data (for example, image data), which is outputted from the control unit 6 to the display 21 so that a corresponding image is displayed on the display.

Figure 2:
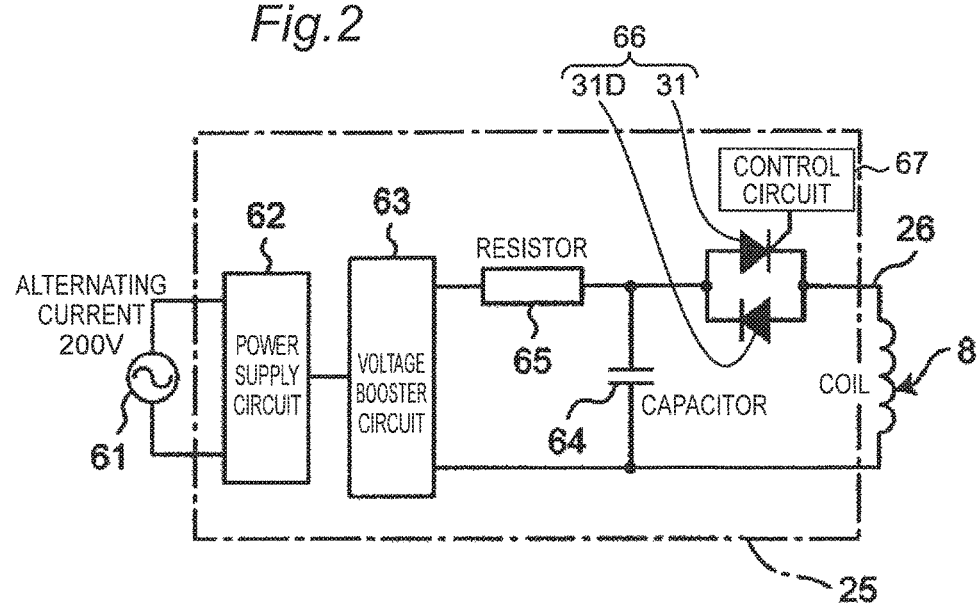
FIG. 2 is a circuit diagram showing a coil drive circuit incorporated in a system of FIG. 1.

A coil drive circuit 25 shown in FIG. 2 is housed in the housing 12, and the coil drive circuit 25 is electrically connected to the coil 8 via a cable 26.

When the patient is to be treated by using the transcranial magnetic stimulation apparatus 1 having the above configuration, the position of the coil 8 with respect to the head of the patient is obtained based on the images taken by the camera 19. The relative position of the coil 8 with respect to the head of the patient is displayed on the display 21. As a result, the coil 8 can be installed at an aimed location (for example, optimum stimulation position) of the head of the patient. Then, the coil drive circuit 25 drives the coil 8 based on the coil drive conditions inputted through the input part 15 and applies magnetic stimulation to the brain of the patient 3. Referring to FIG. 2, the coil drive circuit 25 includes: a power supply circuit 62, which converts the output voltage of a power supply 61 to a desired voltage; a voltage booster circuit 63, which increases the voltage of the output of the power supply circuit 62; a capacitor 64, which accumulates electric charge by using the output from the voltage booster circuit 63; a resistor 65, which adjusts the current flowing in the capacitor 64; and a semiconductor switch 66, which operates the output from the capacitor 64 at a predetermined timing and generates an alternating current. The semiconductor switch 66 is configured to include a thyristor 31 controlled to be turned on/off by a control circuit 67, and a diode 31D, which is connected in parallel in the opposite direction to that of the thyristor 31, and the current obtained by driving the semiconductor switch 66 is applied to the coil 8.

Figure 3:
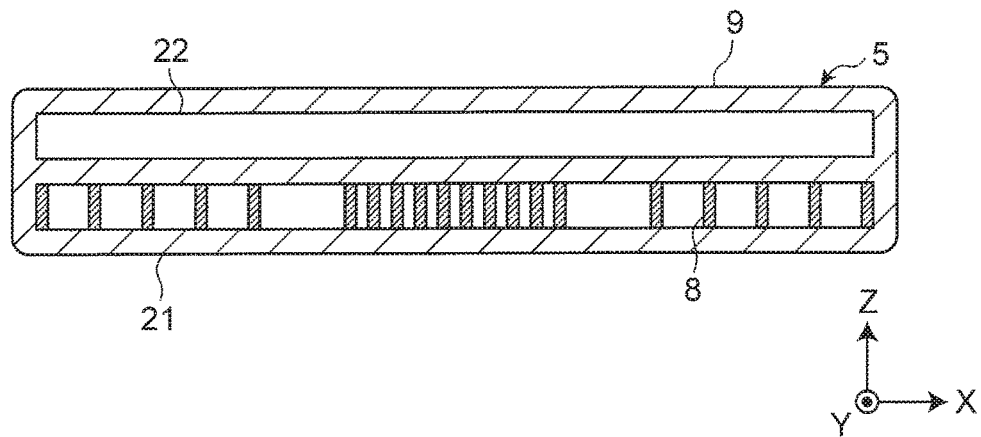
FIG. 3 is a cross-sectional view of a coil apparatus incorporated in the system shown in FIG. 1.

FIG. 3 shows a brief configuration of the coil apparatus 5. Referring to FIG. 3, the coil apparatus 5 includes the casing 9 made of a non-magnetic non-electrically-conductive material. In an embodiment of FIG. 3, a bottom surface 21 of the casing 9 opposing the head of the patient is a flat surface parallel to or substantially parallel to a plane (XY plane) including a left-right direction (X direction) of FIG. 3, and a front-rear direction (Y direction) of the view orthogonal thereto. In the present embodiment, this plane serves as a reference surface.

Figure 4:
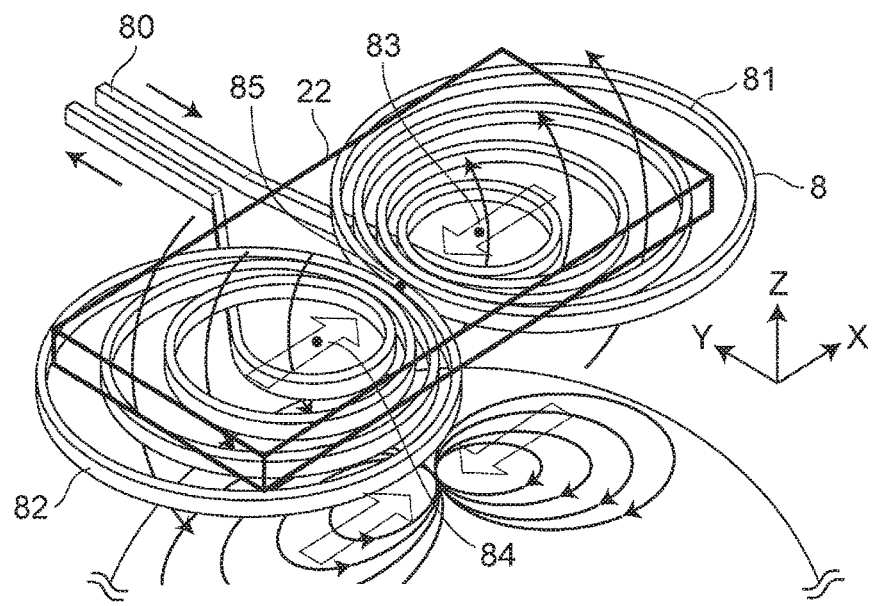
FIG. 4 is a perspective view showing a relation between a coil and a magnetic body in the coil apparatus shown in FIG. 1.

The coil 8 is housed in the casing 9. In the embodiment, the coil 8 is of eccentric type, in which two spiral coil parts 81 and 82 formed by spirally bending a single conductive wire 80 are disposed along the reference surface without overlapping with each other, and the center of each of the two spiral coil parts 81 and 82 is eccentric toward the other spiral coil part. In this case, the coil 8 is a figure-eight-shaped spiral coil of non-overlapping type. In the embodiment, as shown in FIG. 4, the direction (matching an eccentric direction), connecting the centers 83 and 84 of the two spiral coil parts 81 and 82 configuring the figure-eight-shaped spiral coil 8, is defined as an X direction. The direction parallel to the reference surface and orthogonal to the X direction is defined as a Y direction. The direction perpendicular to the reference surface is defined as a Z direction. In this case, in a central part 85 positioned in the middle between the centers 83 and 84 of the coil parts 81 and 82 and in a periphery thereof, the winding wire 80 extends in the Y direction.

Returning to FIG. 3, in the casing 9, a magnetic body 22 having a predetermined volume and a cubic shape is housed above the coil 8 with a predetermined interval between the magnetic body 22 and the coil 8. The magnetic body 22 may be a single sheet made of magnetic steel sheet (magnetic body of above described comparison model) or is a laminated body obtained by laminating thin magnetic steel sheets, which have surfaces covered with insulating coatings. In this case, the coil 8 is positioned so that the bottom surface of the coil 8 opposes the surface of the brain, and the top surface of the coil 8 opposes the magnetic body 22. By providing the magnetic body 22 at the upper side of the coil 8 which is the opposite side of the brain to the case with no magnetic body 22, there are such characteristics that an induced electric field intensity in a magnetic stimulation-target region of the brain can be significantly increased and that the induced electric field can be generated in a wider region.

Figure 6:
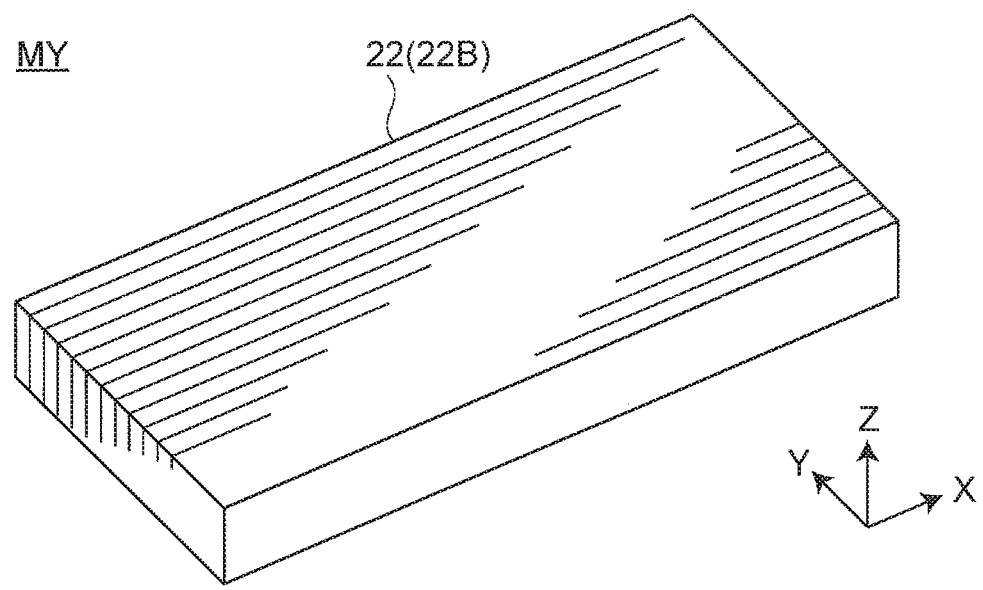
FIG. 6 is a perspective view of a non-rectangular-frame-shaped magnetic body which is obtained by laminating magnetic steel sheets in a Y direction and has a cubic shape.
Figure 7:
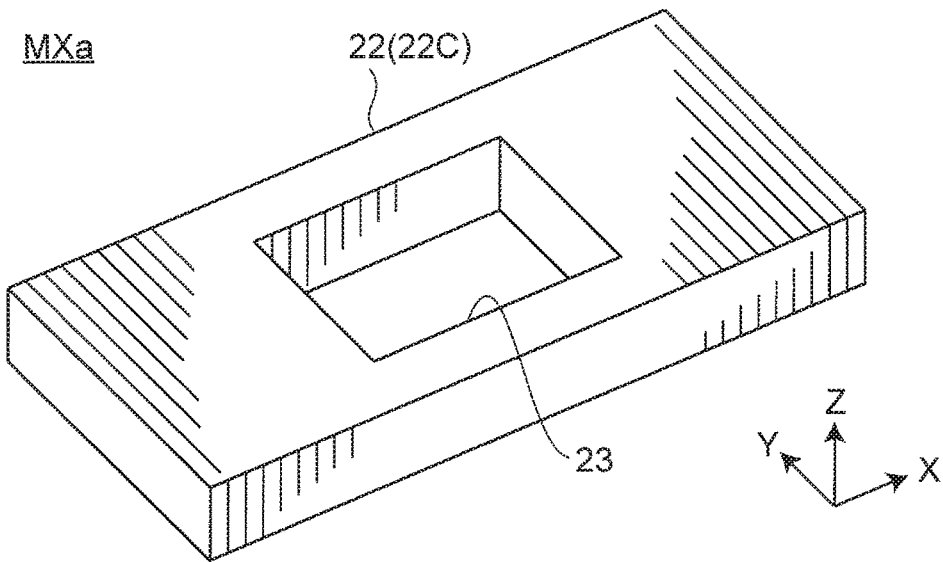
FIG. 7 is a perspective view of a rectangular-frame-shaped magnetic body which is obtained by laminating magnetic steel sheets in the X direction and has a cubic shape.

The magnetic body 22 may be any one of:

(a) laminated bodies 22A and 22C (See FIGS. 5 and 7) in which magnetic steel sheets are laminated in the X direction;

(b) laminated bodies 22B and 22D (See FIGS. 6 and 8) in which magnetic steel sheets are laminated in the Y direction; and (c) laminated bodies 22E to 22H (FIGS. 9 to 12) in which magnetic steel sheets are laminated in the X and Y directions.

The magnetic body 22 may be provide with an opening 23 penetrating through the top surface and the bottom surface thereof (See FIGS. 7, 8, 11 and 12) in the central part thereof. It is noted that, in the embodiments shown in FIGS. 9 and 11, the magnetic steel sheets in both-side regions are laminated in the X direction, and the magnetic steel sheets in the region therebetween are laminated in the Y direction. In the embodiments shown in FIG. 10 and FIG. 12, the magnetic steel sheets in both the side regions are laminated in the Y direction, and the magnetic steel sheets in the region therebetween are laminated in the X direction.

In this case, the models of FIGS. 5 to 12 will be named as the following model names.

Figure 5:
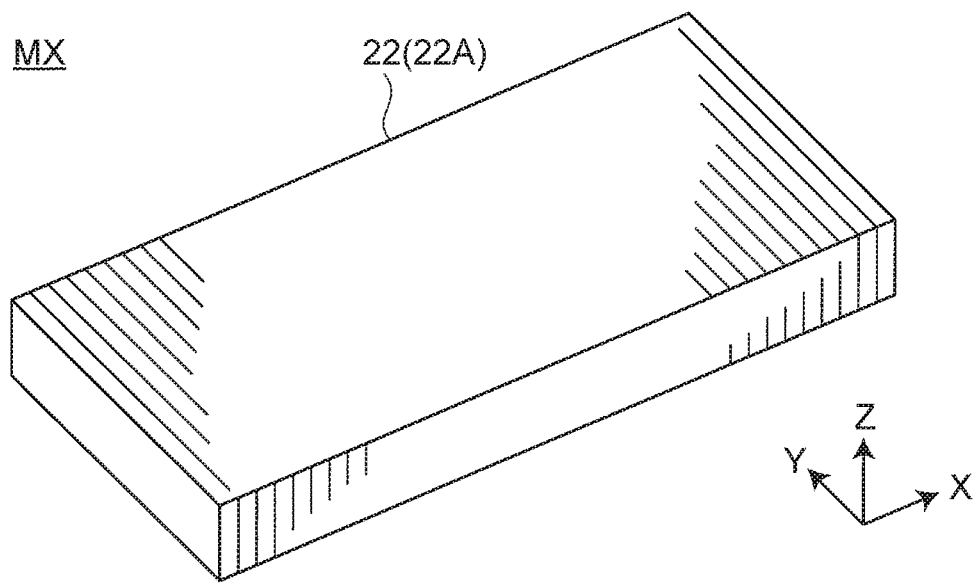
FIG. 5 is a perspective view of a non-rectangular-frame-shaped magnetic body which is obtained by laminating magnetic steel sheets in an X direction and has a cubic shape.

Model of FIG. 5: model MX;
Model of FIG. 6: model MY;
Model of FIG. 7: model MXa;
Model of FIG. 8: model MYa;
Model of FIG. 9: model MZY;
Model of FIG. 10: model MZX;
Model of FIG. 11: model MZYa; and
Model of FIG. 12: model MZXa.

A planar shape of the magnetic body 22 (shape when seen from the Z direction) may be any one of tetragonal shape, and non-tetragonal shape (for example, circular shape, elliptical shape, and oblong shape).

As described above, the coil 8 of FIGS. 3 and 4 is the figure-eight-shaped spiral coil of eccentric type and non-overlapping type. However, the types of the coil 8 are not limited to this, and any one of the following types can be used: a figure-eight-shaped spiral coil of eccentric type and overlapping type, a figure-eight-shaped spiral coil of non-eccentric type and overlapping type, and a figure-eight-shaped spiral coil of non-eccentric type and non-overlapping type.

In the above described embodiment, the bottom surface 21 of the casing 9 is a flat surface, but it may be a curved surface as shown in FIGS. 13 to 16. In this case, the coil 8 is not required to be parallel to the curved surface, but has a curved surface. The coil 8 is only required to be disposed "along" the reference surface. For example, the coil 8 may be disposed in parallel to a flat surface including the X direction and the Y direction, or may be disposed in parallel to the curved surface. Similarly, the magnetic body 22 is also not required to be parallel to the curved surface, but has a curved surface. The magnetic body 22 is only required to be disposed "along" the reference surface. For example, the magnetic body 22 may be disposed in parallel to the flat surface including the X direction and the Y direction or may be disposed in parallel to the curved surface. It is noted that a spherical coil can be formed by disposing a conductive wire along a spherical surface. In addition, a spherical laminated-type magnetic body can be formed, for example, by performing a press working on a flat laminated-type magnetic body to form a spherical shape.

Figure 17:
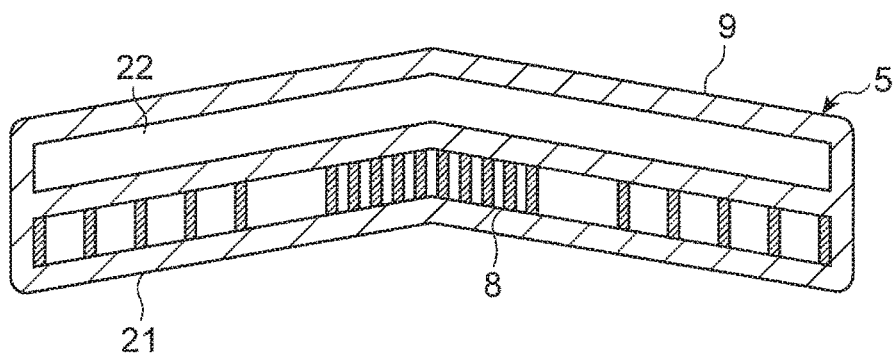
FIG. 17 is a cross-sectional view of a coil apparatus incorporating a flat coil (of overlapping type or non-overlapping type) and a magnetic body in a casing having a bent surface as a bottom surface.

Referring to FIG. 17, the bottom surface of the casing 9 may be a bent surface having two flat surfaces intersecting with each other by a predetermined angle. In this case, the coil 8 may be of eccentric type of non-eccentric type, and of overlapping type or non-overlapping type. In addition, the coil 8 and the magnetic body 22 have bent surfaces. The coil 8 and the magnetic body 22 are only required to be disposed "along" the reference surface. For example, the coil 8 and the magnetic body 22 may be disposed to be in parallel to the flat surface including the X direction and the Y direction, or may be disposed in parallel to the bent surface.

Although the bottom surface 21 of the casing 9 is not shown in the drawings, the bottom surface 21 of the casing 9 may be a spherical surface. In this case, the coil 8 has a spherical surface, but is not required to be parallel to the spherical surface. The coil 8 is only required to be disposed "along" the reference surface. For example, the coil 8 may be disposed in parallel to the flat surface including the X direction and the Y direction, or may be disposed in parallel to the spherical surface. Similarly, the magnetic body 22 also has a spherical surface, but is not required to be parallel to the spherical surface. The magnetic body 22 is only required to be disposed "along" the reference surface. For example, the magnetic body 22 may be disposed in parallel to the flat surface including the X direction and the Y direction, or may be disposed in parallel to the spherical surface.

The magnetic body 22 has preferably a size capable of entirely covering the coil 8. However, when the coil 8 is a figure-eight-shaped coil, the magnetic body 22 preferably has a size that covers at least the minimum inner-diameter region of the two spiral coil parts.

It is noted that, in the above described description, the coil is the figure-eight-shaped spiral coil including the two spiral coil parts. However, the present invention can be similarly applied to a spiral coil including three or four spiral coil parts.

According to the coil apparatus 5 configured in this manner, as described in the above described analysis, since the magnetic body is disposed along the coil, a larger induced electric field intensity can be generated on the surface of the brain, than that of the coil apparatus with no magnetic body. In particular, in the case of the coil apparatus including the figure-eight-shaped spiral coil, when the magnetic steel sheets are laminated in the direction orthogonal to the direction connecting the centers of the two spiral coil parts to configure the magnetic body, magnetic flux leakage can be minimally suppressed. In addition, a larger induced electric field intensity can be generated in a target treatment part, which is a magnetic stimulation-target region, with high robustness in a predetermined direction.

IMPLEMENTATION EXAMPLES 2.1 Numerical Analysis 1

Figure 18:
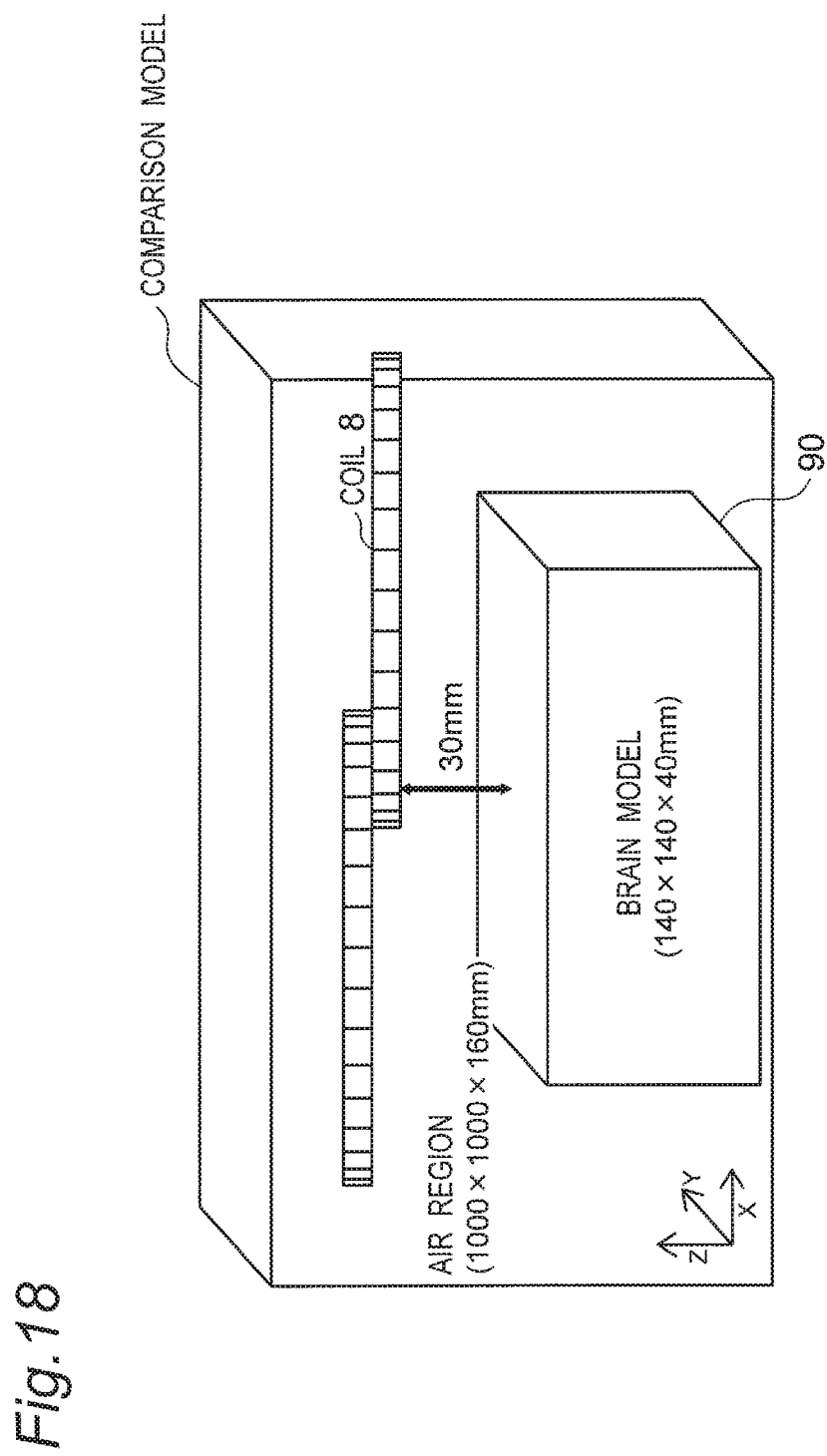
FIG. 18 is a perspective view showing a comparison model not including a magnetic body.
Figure 19:
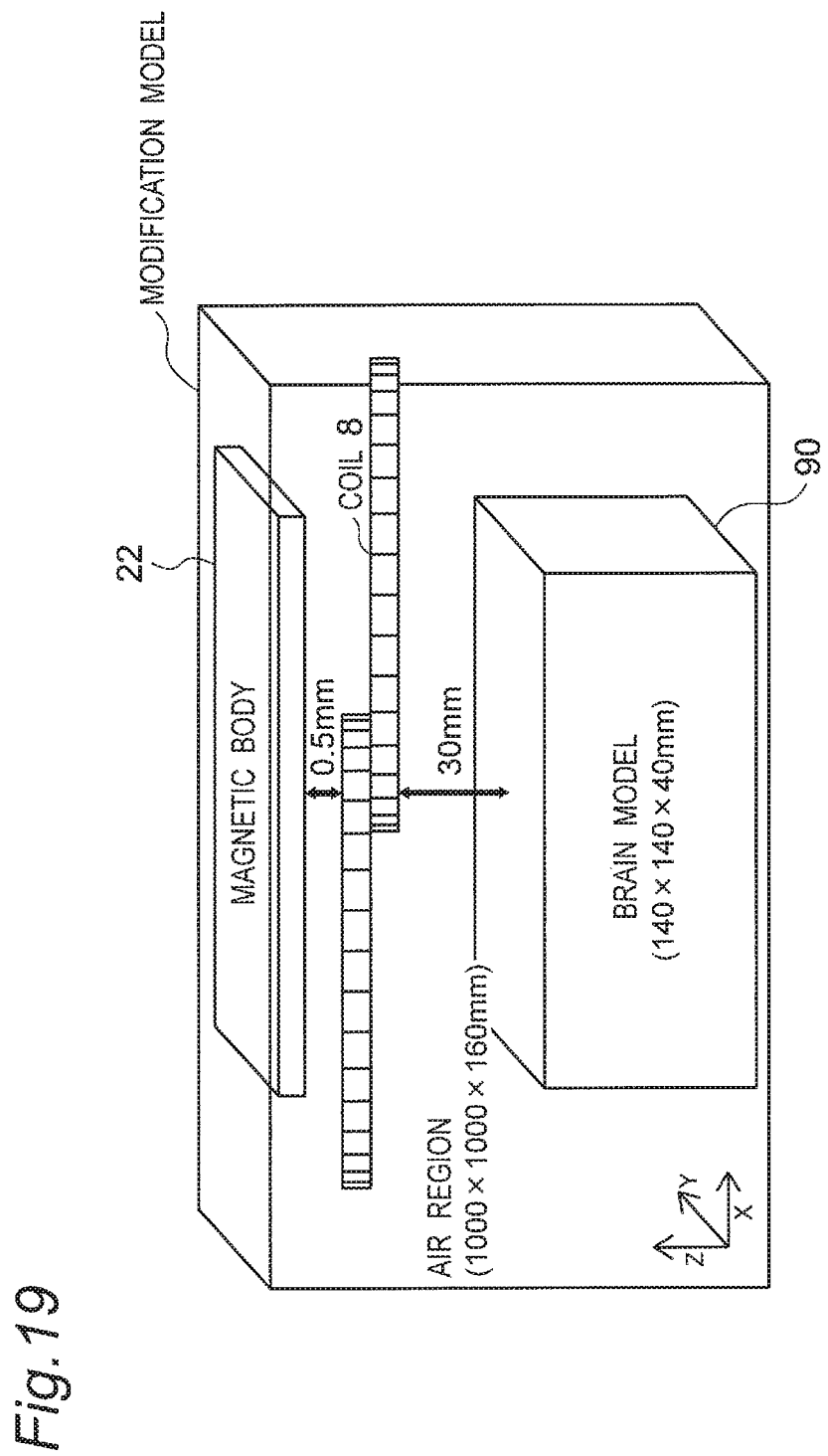
FIG. 19 is a perspective view showing a modification model including a magnetic body.

Regarding magnetic-stimulation coil apparatuses, the inventors of the invention of the present application created two analysis models and evaluated the intensity of an induced magnetic field by using a finite element method, magnetic field leakage, and locality, in order to improve magnetic stimulation efficiency, reduce magnetic field leakage, improve stimulation robustness, and to carry out downsizing. Referring to FIG. 18, one analysis model was a model in which a cuboidal (rectangular parallel piped) brain model and an overlapping-type eccentric figure-eight-shaped spiral coil were disposed in a cuboidal space (air region) (hereinafter, referred to as "a comparison model"). Referring to FIG. 19, another analysis model was a model in which a cubic magnetic body was disposed in addition to the above described cuboidal brain model and the eccentric figure-eight-shaped spiral coil in a cuboidal space (air region) (hereinafter, referred to as "a modification model").

2.1.1 Comparison Model and Modification Model

Figure 20:
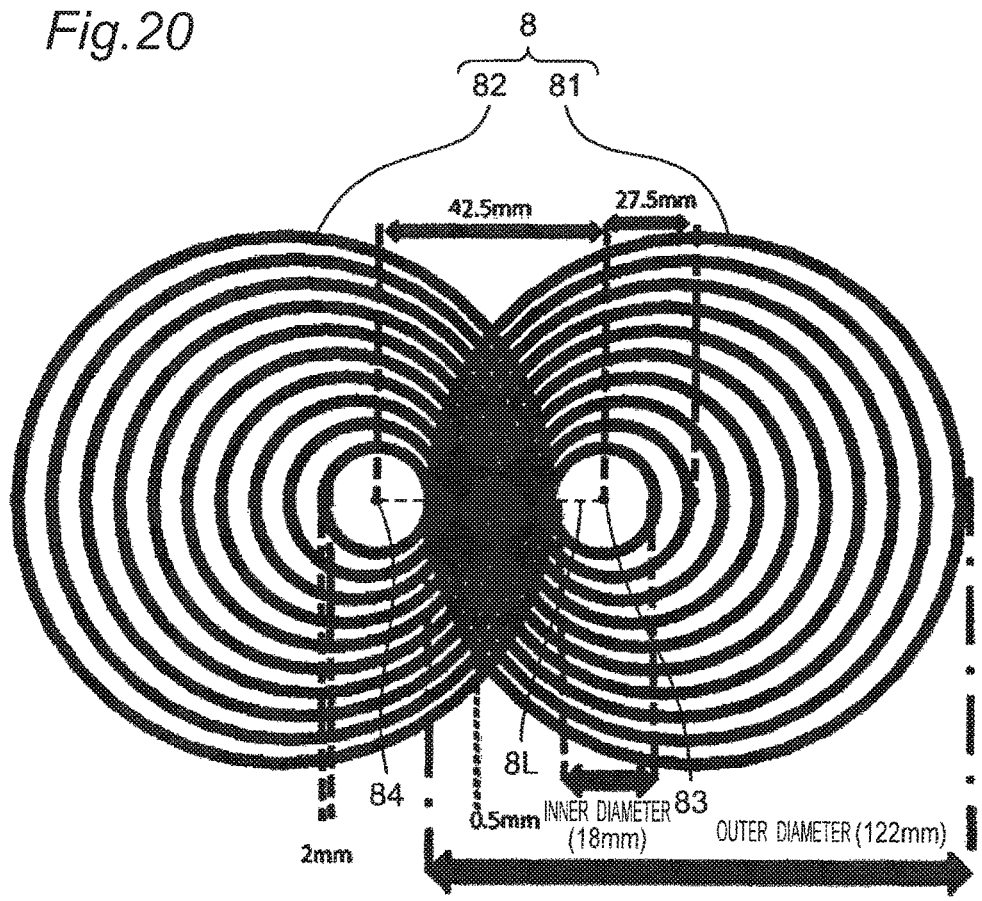
FIG. 20 is a pattern diagram of a coil used in analysis.

In the comparison model and the modification model, the size of the cuboidal space was 1000×1000×1600 mm (showing "X direction size×Y direction size×Z direction size". Hereinafter, sizes thereof are shown in a manner similar to that.), the size of the brain model was 140×140×40 mm. Referring to FIG. 20, the eccentric figure-eight-shaped spiral coil includes two spiral coil parts 81 and 82, by spirally winding a conductive wire (conductor) having a width of 2 mm and a height of 6 mm, along a single plane. In this case, the eccentric figure-eight-shaped spiral coil includes the two eccentric spiral coil parts 81 and 82 so that each of centers 83 and 84 of the two spiral coil parts 81 and 82 was eccentric toward the other coil part. Each of the eccentric spiral coil parts 81 and 82 had the following:

the minimum inner diameter of 18 mm;
the maximum outer diameter of 122 mm;
an eccentric degree (the distance between an outer-diameter center and an inner-diameter center of the eccentric spiral coil part) of 27.5 mm;
the distance between the inner-diameter centers of the left/right eccentric spiral coil parts 81 and 82 of 42.5 mm; and
an eccentric-side minimum coil gap (in FIG. 18, a left-side region in the eccentric spiral coil part 81 shown at the right side, and in a right-side region in the eccentric spiral coil part 82 shown at the left side) of 0.5 mm.

The eccentric figure-eight-shaped spiral coil 8 having the above described configuration was arranged so that a line 8L connecting the centers of the two eccentric spiral coil parts (hereinafter, this line will be referred to as "a central axis of the eccentric figure-eight-shaped spiral coil") was directed to be in parallel to the X direction.

As shown in FIGS. 18 and 19, the brain model and the eccentric figure-eight-shaped spiral coil were positioned at the center of the eccentric figure-eight-shaped spiral coil above the center of the brain model 90. A gap of 30 mm was provided between the brain model 90 and the eccentric figure-eight-shaped spiral coil 8. The eccentric figure-eight-shaped spiral coil 8 was arranged, so that the line connecting the centers 83 and 84 of the two eccentric spiral coil parts 81 and 82 (hereinafter, this line will be referred to as "a central axis of the eccentric figure-eight-shaped spiral coil") was directed to be in parallel to the X direction, and so that the direction on the plate surface of the coil and being orthogonal to the central axis 8L of the eccentric figure-eight-shaped spiral coil 8 was directed to be in parallel to the Y direction.

Figure 21:
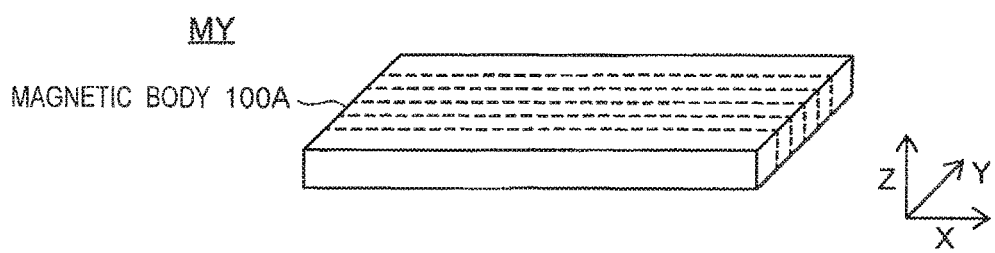
FIG. 21 is a perspective view of a non-rectangular-frame-shaped magnetic body which is obtained by laminating magnetic steel sheets in the X direction and has a cuboidal shape.
Figure 22:
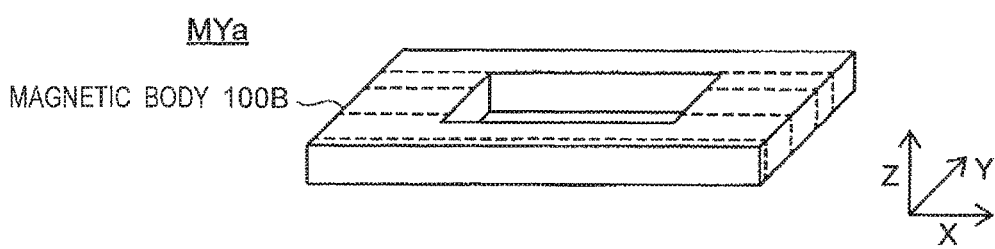
FIG. 22 is a perspective view of a non-rectangular-frame-shaped magnetic body which is obtained by laminating magnetic steel sheets in the Y direction and has a cuboidal shape.
Figure 23:
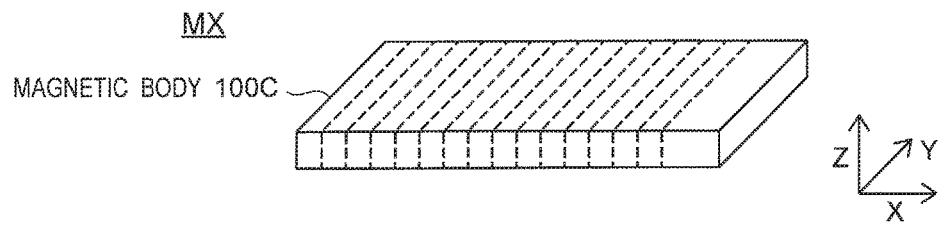
FIG. 23 is a perspective view of a rectangular-frame-shaped magnetic body which is obtained by laminating magnetic steel sheets in the X direction and has a cuboidal shape.
Figure 24:
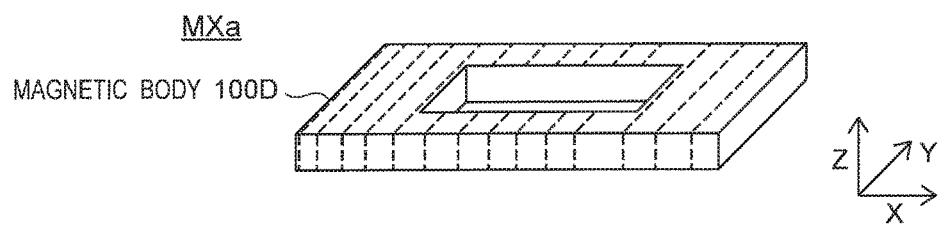
FIG. 24 is a perspective view a rectangular-frame-shaped magnetic body which is obtained by laminating magnetic steel sheets in the Y direction and has a cuboidal shape.

In the modification model shown in FIG. 19, for example, the cuboidal magnetic body 22 was disposed above the eccentric figure-eight-shaped spiral coil with a gap of 0.5 mm therebetween. As the cuboidal magnetic body 33, four types of magnetic bodies 100A to 100D shown in FIGS. 21 to 24 were prepared. The magnetic body 100A of FIG. 21 was a cuboidal magnetic body (non-rectangular-frame shape) configured by laminating magnetic steel sheets in the Y direction of FIG. 21. The magnetic body 100B of FIG. 22 was a cuboidal magnetic body (frame shape) including a tetragonal opening (45 mm×80 mm) at a center of the magnetic body 100A. The magnetic body 100C of FIG. 23 was a cuboidal magnetic body (non-rectangular-frame shape) configured by laminating magnetic steel sheets in the X direction of FIG. 23. The magnetic body 100D of FIG. 24 was a cuboidal magnetic body (frame shape) including a tetragonal opening (45 mm×80 mm) at a center of the magnetic body C. The size of each of the magnetic bodies 100A to 100D had a sufficient area for covering the entire top surface of the eccentric coil 8. In calculations, the thickness of the magnetic steel sheets was ignored.

The electric conductivity of the brain model 90 was 0.11 (S/m) (this was equivalent to that of the gray matter of the brain), and the relative magnetic permeability thereof was set to one. The electric conductivity of the air region was set to zero (S/m), and the relative magnetic permeability thereof was set to zero. The electric conductivity of the magnetic body was $10^7$ (S/m), and the relative magnetic permeability thereof was 5000. The number of elements of both of the analysis models was about 1,000,000. Hereinafter, modification models including the magnetic bodies 100A, 100B, 100C, and 100D will be referred to as "a modification model MY", "a modification model MYa", "a modification model MX", and "a modification model MXa", respectively.

2.1.2 Analysis Method
(a) Calculation Equations of Induced Electric Field

Analysis of a current density was carried out by the EDDY-jω method based on the finite element method. When a magnetic field is noted by "B", a vector potential of a coil current is noted by "Ac", a vector potential of an eddy current is noted by "Ae", an electric field is noted by "E", a current is noted by "J", a scalar potential is noted by "φ", and the time is noted by "t", then equations representing electromagnetic fields can be given such that a magnetic field is given by Equation (1), and an electric field E is given by Equation (2).

$$B = \Delta \times A \quad (1)$$

$$E = -\nabla \varphi - \frac{\partial}{\partial t}(A_c + A_e) \quad (2)$$

$$\nabla \times \frac{B}{\mu_0} = J \quad (3)$$

When a term of the vector potential of the eddy current of Equation (1) is substituted into Equation (3) with φ=0 and magnetic permeability $\mu_0$ of vacuum, the following Equation (4) is obtained.

$$\nabla \times \frac{1}{\mu_0} \nabla \times A_c = J_e \quad (4)$$

In this case, "Je" denotes an eddy current. The vector potential of the coil current is given by the following Equation (5) according to the publicly-known Biot-Savart law.

$$A_c = \frac{\mu_0 I}{4\pi} \int_C \frac{t(r')}{|r - r'|} dS' \quad (5)$$

Therefore, Equation (7) is obtained from Equations (2) to (4) and Equation (6).

$$J_e = \sigma E \quad (6)$$

$$\nabla \times \frac{1}{\mu_0} \nabla \times A_e = -\sigma \frac{\partial}{\partial t}\left(A_e + \frac{\mu_0 I}{4\pi} \int_C \frac{t(r')}{|r - r'|} dS'\right) \quad (7)$$

When the electromagnetic field changes in a form of sine wave, a complex field Ac (XYZ) is given by the following Equation (8).

$$A(x,y,z,t) = \mathrm{Re}(Ac(x,y,z)\exp(j\omega t)) \quad (8)$$

Therefore, when Equation (8) is substituted into Equation (7), the equation to be satisfied by the complex field is given by the following Equation (9).

$$\nabla \times \frac{1}{\mu_0} \nabla \times A_e = -j\omega\sigma\left(A_e + \frac{\mu_0 I}{4\pi} \int_C \frac{t(r')}{|r - r'|} dS'\right) \quad (9)$$

In the present analysis, this complex field was obtained as an analysis result.

(b) Analysis of Induced Electric Field Intensity

Figure 36:
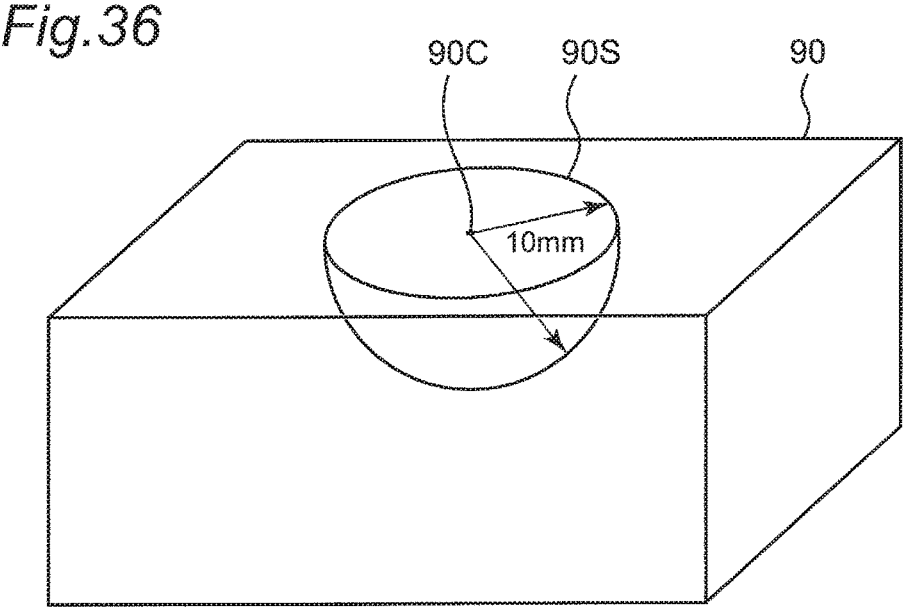
FIG. 36 is a perspective view showing elements used in calculations of an average induced electric field of a central part of the brain model.

In order to evaluate magnetic stimulation efficiency on each of the comparison model and the four modification models, the distribution of the induced electric field intensity on the top surface of the brain model 90 (hereinafter, referred to as "a brain-surface-induced electric field intensity") and an induced electric field at a central point on the top surface of the brain model 90 (hereinafter, referred to as "a target point".) were analyzed. In order to evaluate the induced electric field at the target point, as shown in FIG. 36, an average value of the induced electric fields of the brain elements in a hemisphere 90S having a radius of 10 mm from a target point 90C (elements of the brain model 90 defined for analysis) was referred to as an effective-stimulation brain-surface-induced electric field intensity.

(c) Analysis of Upward-Direction Magnetic Field Leakage of Coil

Figure 25:
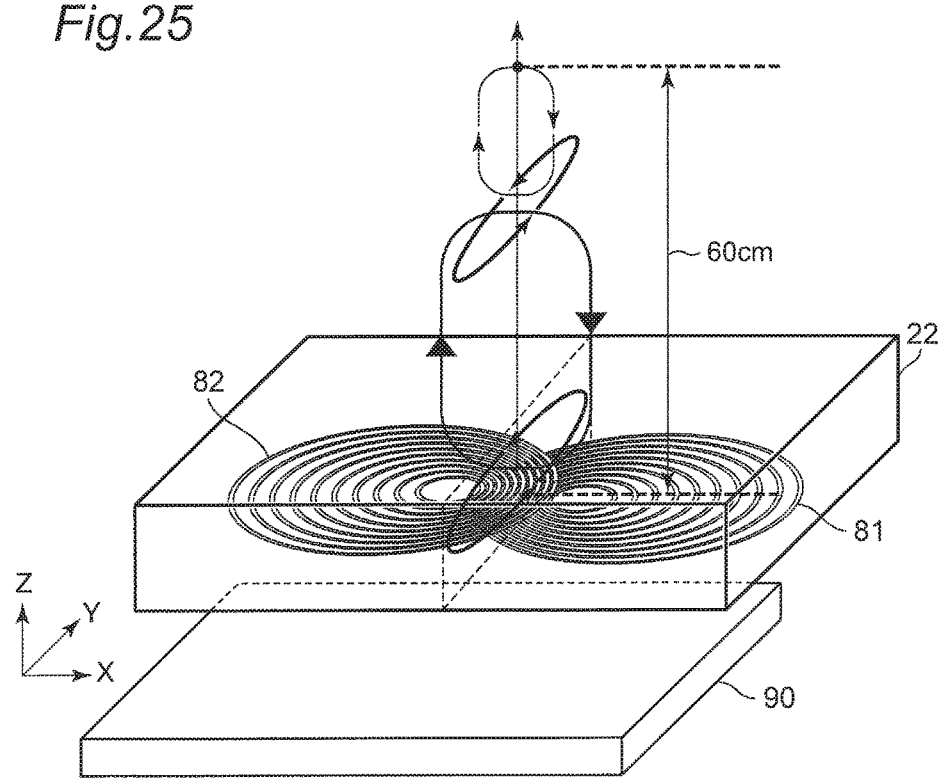
FIG. 25 is a perspective view showing an evaluation point of magnetic field leakage analysis.

Regarding the comparison model of FIG. 18 and the modification models of FIG. 19 including the four magnetic bodies 100A to 100D shown in FIGS. 21 to 24, as shown in FIG. 25, the magnetic-field intensity of an evaluation point which was distant from the target point by 60 cm at the upper side (Z-axis direction) was calculated.

(d) Analysis of Stimulation Robustness

In order to evaluate the size of the region capable of applying a desired stimulation intensity to an aimed stimulation position even if the stimulation coil 8 was misaligned from a predetermined position (robustness), 70% of the maximum induced electric field on the brain surface was set to an effective stimulation intensity, and the region having an electric field having an intensity which was the same as or higher than the effective stimulation intensity was set to an effective stimulation region. A width in the X direction and a width in the Y direction of the effective stimulation region were calculated, and half of each of the values thereof was defined as the maximum permissible misalignment error.

2.1.3 Analysis Results
(a) Induced Electric Field Intensity at Brain Surface

Figure 26:
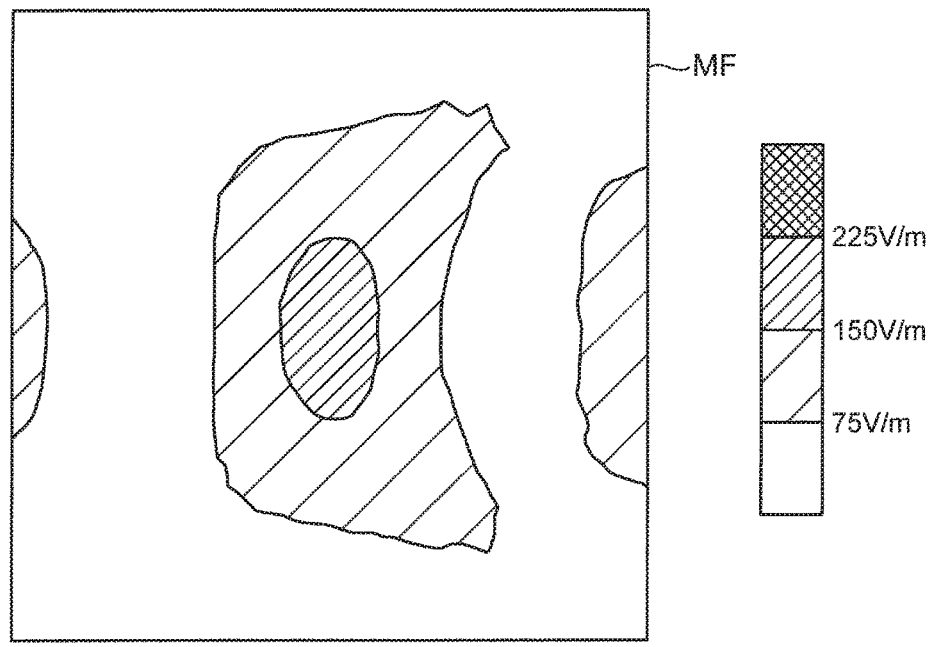
FIG. 26 is a contour graph showing a distribution of brain-surface-induced electric field intensities of a comparison model MF.
Figure 27:
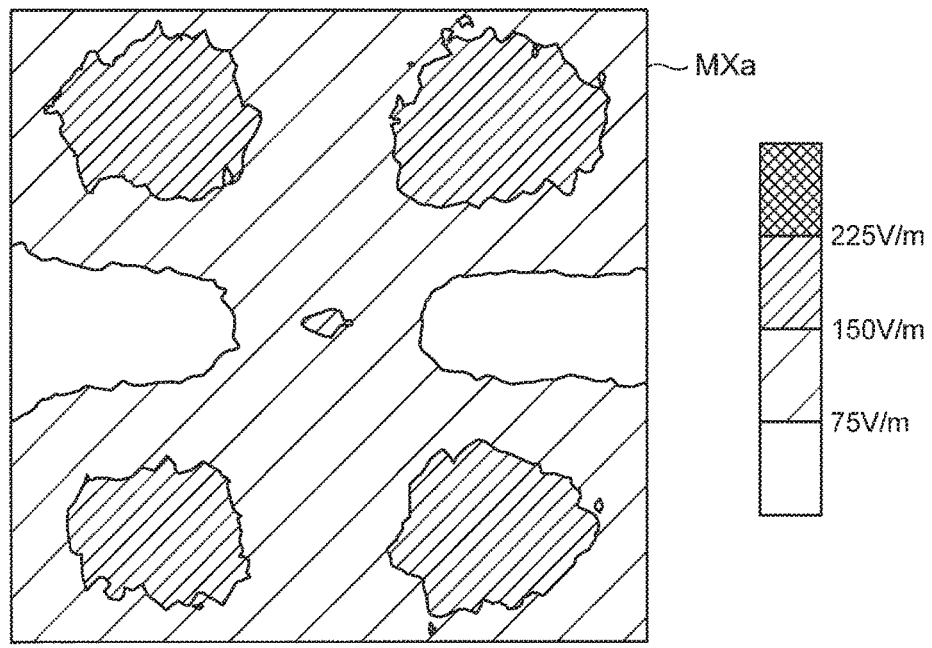
FIG. 27 is a contour graph showing a distribution of brain-surface-induced electric field intensities of a modification model MXa.
Figure 28:
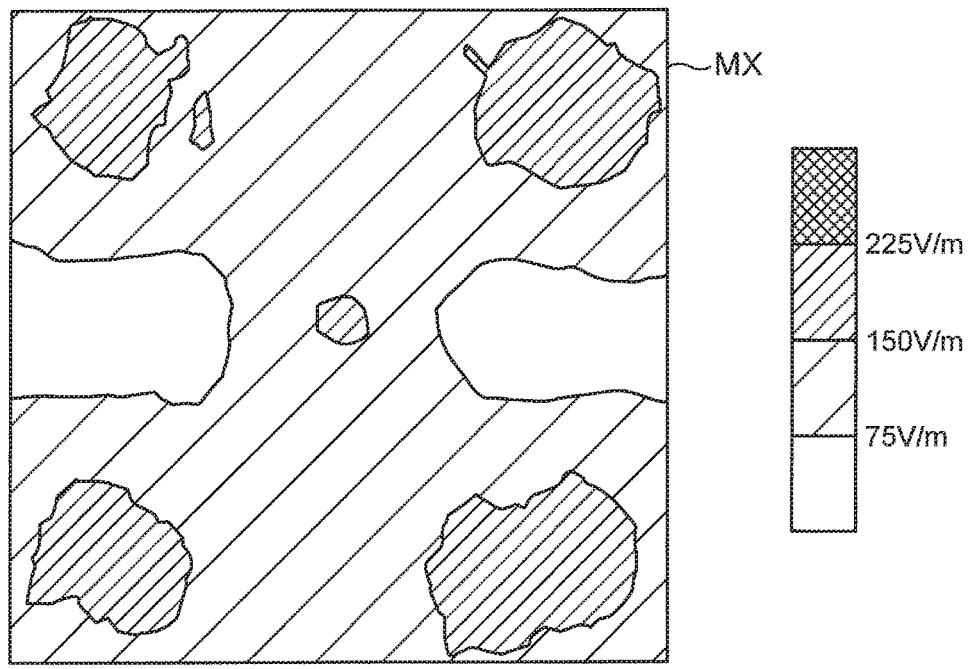
FIG. 28 is a contour graph showing a distribution of brain-surface-induced electric field intensities of a modification model MX.
Figure 29:
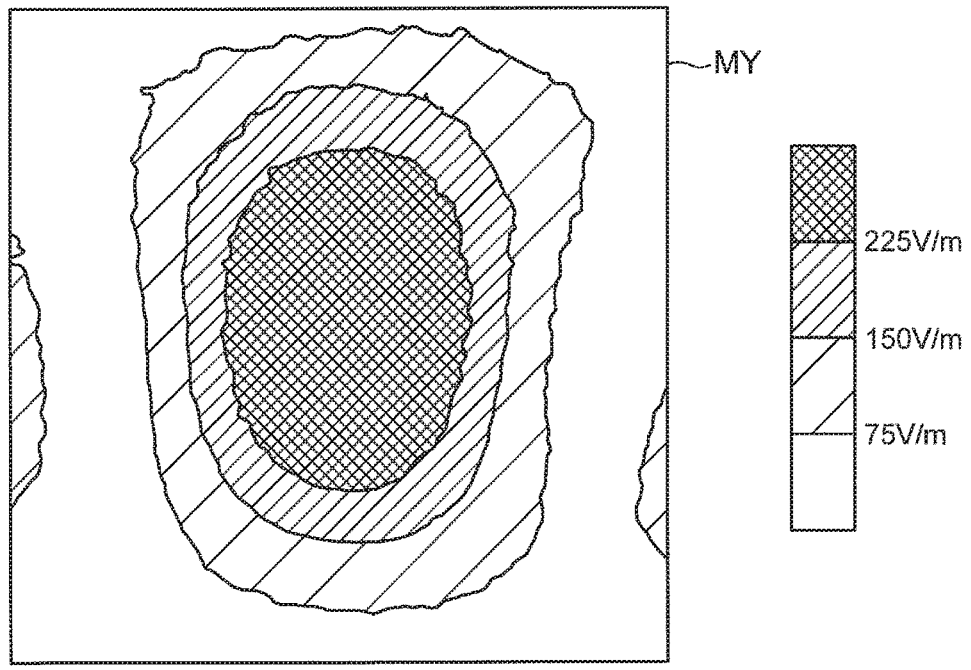
FIG. 29 is a contour graph showing a distribution of brain-surface-induced electric field intensities of a modification model MY.
Figure 30:
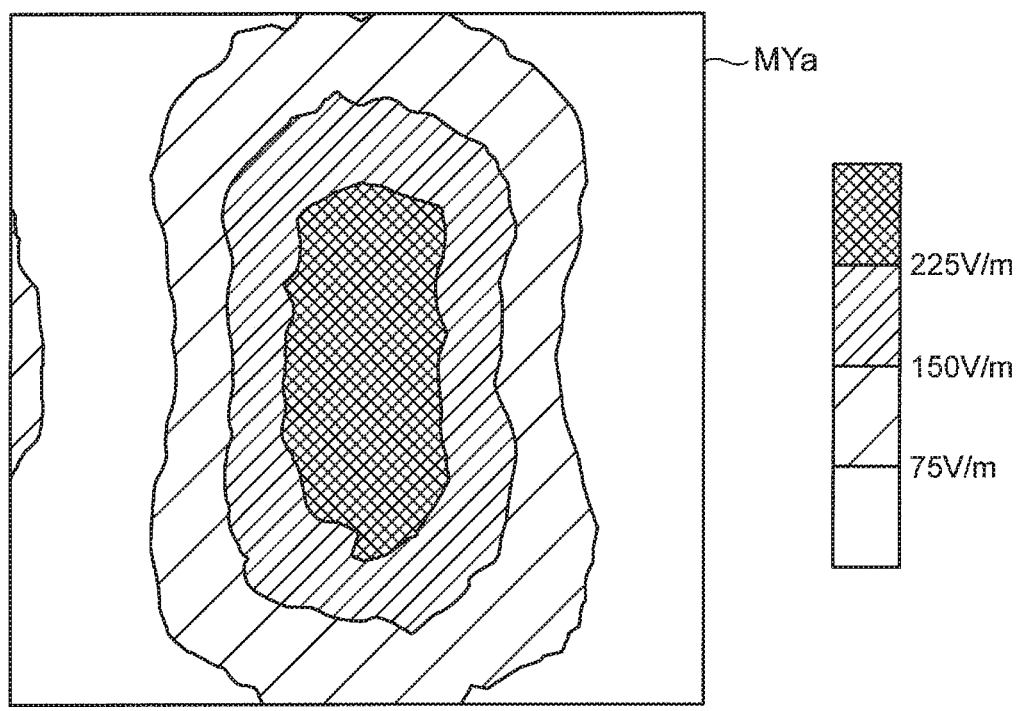
FIG. 30 is a contour graph showing a distribution of brain-surface-induced electric field intensities of a modification model MYa.

FIG. 26 shows a distribution of brain-surface-induced electric field intensities of the comparison model MF (FIG. 18), and FIG. 27 to FIG. 30 show distributions of brain-surface-induced electric field intensities of the modification models MY, MYa, MX, and MXa (See FIGS. 19 and 21 to 24).

(b) Effective-Stimulation Brain-Surface-Induced Electric Field Intensity at Target Point Table 1 shows effective-stimulation brain-surface-induced electric field intensities at the target point.

TABLE 1

| | Comparison Model MF | Modification Model MX | Modification Model MXa | Modification Model MY | Modification Model MYa |
|---|---|---|---|---|---|
| Effective Induced Electric field Intensities (V/m) of Stimulated Brain Surface | 118 | 120 | 129 | 297 | 207 |

As shown in Table 1, the effective brain-surface-induced electric field intensity of the comparison model with no magnetic body was 118 (V/m). On the other hand, the effective brain-surface-induced electric field intensities of four types of modification models MX, MXa, MY, and MYa were 120 (V/m), 129 (V/m), 297 (V/m), and 207 (V/m), respectively. All of the modification models obtained larger effective brain-surface-induced electric field intensities than that of the comparison model. In particular, in the modification model MY (the model having the cuboidal magnetic body obtained by laminating the magnetic steel sheets in the Y direction), the effective brain-surface-induced electric field intensity which is about 2.5 times that of the comparison model was obtained. According to these results, it could be understood that, also in all of the modification models MX, MXa, MY, and MYa, in which the magnetic body 22 was disposed above the eccentric figure-eight-shaped spiral coil 8, more induced electric fields could be generated on the surface of and in the internal portion of the brain model 90, than that of the comparison model MF. In addition, it could be understood that the cases of the modification models MY and MYa in which the magnetic steel sheets were laminated in the direction (Y direction) orthogonal to the central axis 8L (X direction) of the eccentric figure-eight-shaped spiral coil 8 were capable of generating much larger induced electric fields on the surface of and in the internal portion of the brain model 90, than those of the models MX and MXa in which the magnetic steel sheets were laminated in the direction (X direction) parallel to the central axis of the eccentric figure-eight-shaped spiral coil.

(c) Induced Electric Field in Magnetic Body

Figure 31:
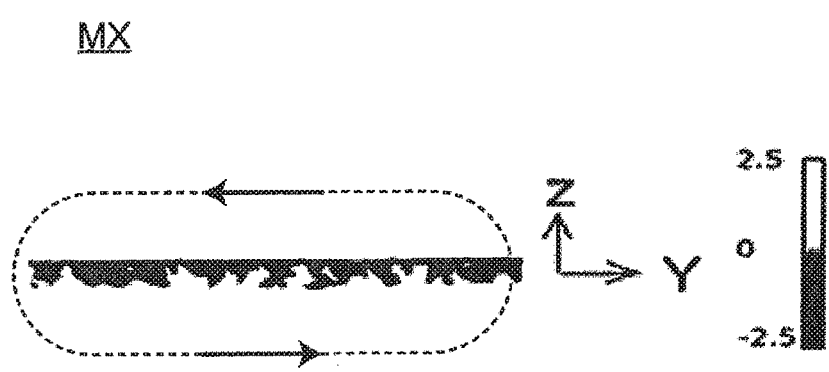
FIG. 31 is a view showing the intensity distribution of an induced electric field generated in the magnetic body of the modification model MX.
Figure 32:
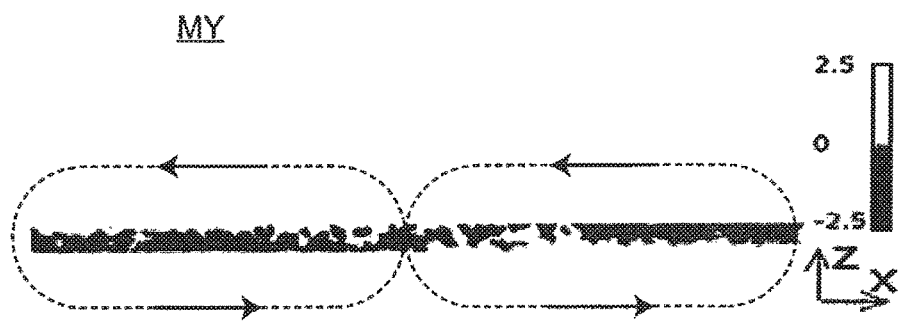
FIG. 32 is a view showing the intensity distribution of induced electric fields generated in the magnetic body of the modification model MY.

Regarding the modification models MX and MY each having the cuboidal magnetic body 22 obtained by laminating the magnetic steel sheets in the X direction or the Y direction, the intensity distributions of induced electric fields generated in a Y direction cross section and an X direction cross section of a central part of the magnetic body were analyzed. FIGS. 31 and 32 show analysis results thereof. Referring to FIGS. 31 and 32, in the case of the modification model MX, such results were obtained that, (a) a high-intensity induced electric field appeared at the bottom-surface side of the magnetic body 22; and (b) a low-intensity induced electric field appeared at the top-surface side of the magnetic body 22.

In the case of the modification model MY, such results were obtained that, (a) in a left-side region, a high-intensity induced electric field appeared at the top-surface side of the magnetic body 22; and a low-intensity induced electric field appeared at the bottom-surface side of the magnetic body 22; and however, (b) in a right-side region, a high-intensity induced electric field appeared at the bottom-surface side of the magnetic body 22; and a low-intensity induced electric field appeared at the top-surface side of the magnetic body 22.

Figure 33:
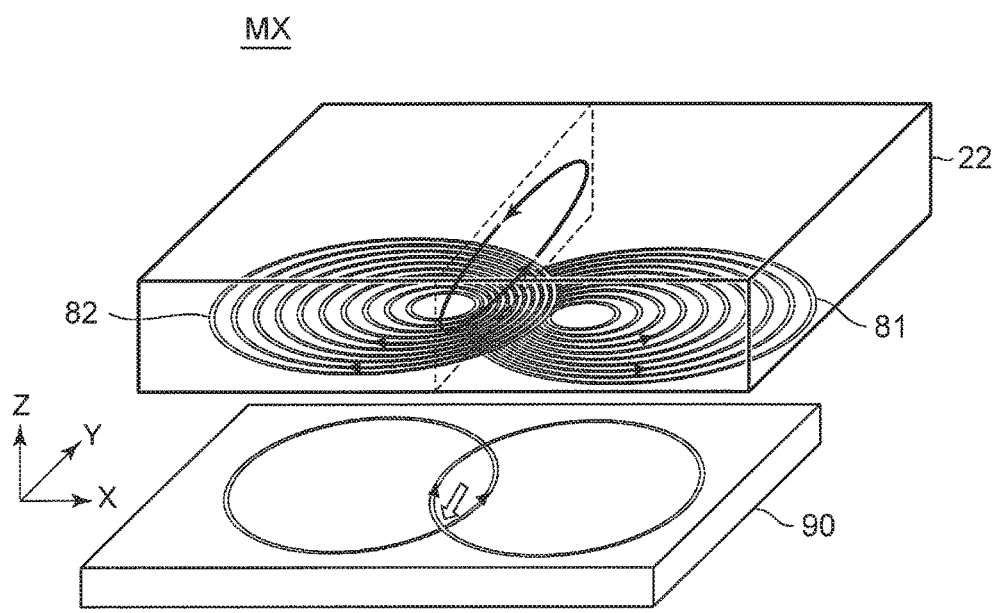
FIG. 33 is a perspective view showing an induced current flowing in a magnetic body of a model A.

According to these results, as shown by arrows in FIGS. 31 to 34, it was conceived (a) that an induced current flowed in a form of ring along the Y direction cross section in the modification model MX; and (b) that induced currents flowed in a form of ring along the X direction cross section in the opposite directions in the left/right respective regions in the modification model MY. Therefore, it was conceived that, in any of the modification models, because of the high magnetic permeability of the magnetic body, the magnetic resistance around the coil reduces, the magnetic field on the brain surface was reinforced, and the electric field in the brain was enhanced. It was conceived that an induced current as shown in FIG. 33 flowed in the cuboidal magnetic body 22 of the modification model MX, in which the magnetic steel sheets were laminated in the X direction, and the induced current causes a current to flow at the target point of the brain surface in the direction that weakens the induced currents generated on the brain surface. In addition, it was conceived that, in the case of the rectangular-frame-shaped magnetic body of the modification model MXa, in which the magnetic steel sheets were laminated in the X direction, the induced currents of the brain did not decrease since induced currents do not flow in the central part.

Figure 34:
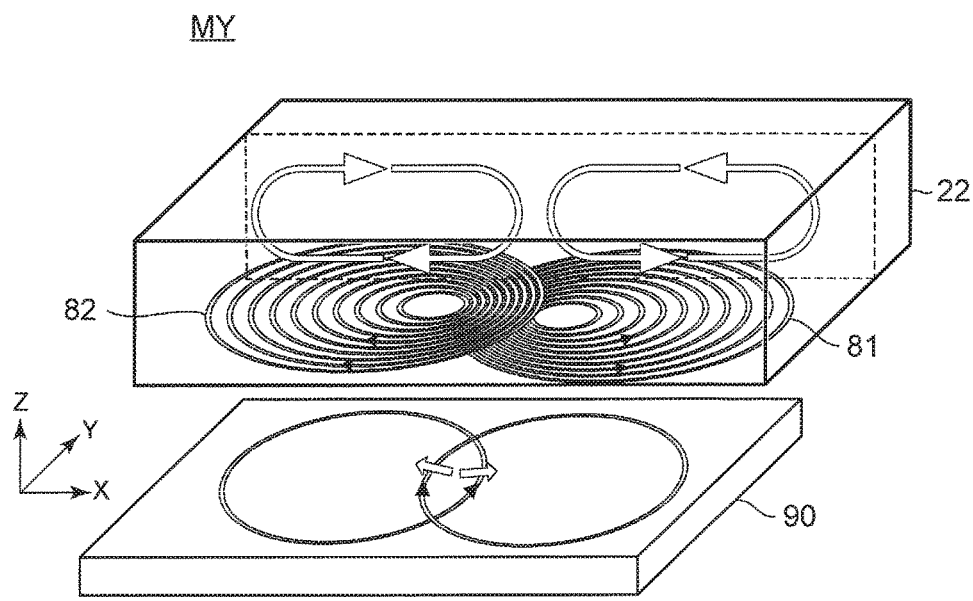
FIG. 34 is a perspective view showing induced currents flowing in a magnetic body of a model C.

It was conceived that, since induced currents shown in those of FIG. 34 flowed in the cuboidal magnetic body 22 of the modification model MY, in which the magnetic steel sheets were laminated in the Y direction, the currents flowing in the coil parts 81 and 82 generated the currents having the directions orthogonal to the induced currents generated on the brain surface, at the target point. It was conceived that, in the case of the rectangular-frame-shaped cuboidal magnetic body of the modification model MYa, in which the magnetic steel sheets were laminated in the Y direction, the magnetic permeability decreased, however, the currents flowing in the coil parts 81 and 82 did not weaken the induced electric field generated on the brain surface. Therefore, as shown in Table 1, it was conceived that, the modification model MY of the cuboidal magnetic body 22, in which the magnetic steel sheets were laminated in the Y direction, was capable of obtaining stimulation of highest efficiency.

(d) Magnetic Field Leakage

Regarding the comparison model and the four types of modification models, the results of calculating the intensities of magnetic field leakage at the position (referred to as "an evaluation point") 60 cm above (Z-axis direction) a central point on the top surface of the eccentric figure-eight-shaped spiral coil 8 were obtained. The intensities of the magnetic field leakage at the evaluation point were 8 (A/m) in the comparison model and were 9 (A/m), 24 (A/m), 9 (A/m), and 20 (A/m) in the four types of modification models, respectively. In addition, all of the modification models MY, MYa, and MX excluding the modification model MXa (the model having the X direction-laminated rectangular-frame-shaped magnetic body) obtained the results which satisfied the safety standards defined by the International Commission on Non-Ionizing Radiation Protection (ICNIRP).

Regarding the presence/absence and shape of the magnetic body 22, it was found out that, the magnetic field leakage of the comparison model with no magnetic body 22 was the smallest, and the magnetic field leakage increased in the order of the non-rectangular-frame-shaped cuboidal magnetic body and the rectangular-frame-shaped cuboidal magnetic body. This was conceivably for the following reasons:

(A) the rectangular-frame-shaped magnetic body allowed the magnetic field to drop out toward the Z direction upper side through the central opening part thereof; and, (B) on the other hand, the non-rectangular-frame-shaped cuboidal magnetic body blocked such a dropped-out magnetic field by the induced current in the magnetic body, which leads to decrease of the magnetic field leakage.

(e) Stimulation Robustness

The X direction and Y direction widths of the range having the induced electric field intensity equal to or more than 70% of a peak (maximum) value of the induced electric field were calculated. Half the values of the widths, i.e., the maximum permissible misalignment range (the range in which misalignment of the coil center was permitted) were obtained for the comparison model and the four types of modification models. Table 2 shows the maximum permissible ranges.

TABLE 2

| Maximum Permissible Misalignment Range (mm) | Comparison Model MF | Modification Model MX | Modification Model MXa | Modification Mode MY | Modification Model MYa |
|---|---|---|---|---|---|
| X direction | 16 | 12 | 13 | 21 | 17 |
| Y direction | 28 | 35 | 31 | 28 | 31 |

As was apparent from Table 2, in the cases of the modification models MX and MXa, in which the magnetic steel sheets were laminated in the X direction, the difference between the maximum permissible misalignment range in the Y direction and the maximum permissible misalignment range in the X direction (23 mm in the modification model MX, and 18 mm in the modification model MXa) was large. On the other hand, in the cases of the modification models MY and MYa, in which the magnetic steel sheets were laminated in the Y direction, the difference between the maximum permissible misalignment range in the X direction and the maximum permissible misalignment range in the Y direction (7 mm in the modification model MX, and 14 mm in the modification model MXa) was smaller than that of the modification models MX and MXa. Therefore, it was confirmed that the modification models MY and MYa, in which the magnetic steel sheets were laminated in the Y direction, had higher robustness than that of the modification models MX and MXa, in which the magnetic steel sheets were laminated in the X direction. In each of the modification models MX and MXa, it was confirmed that the high magnetic permeability provided by the magnetic body 22 attracted the magnetic flus lines at the upper side or lateral side of the coil 8 to the magnetic body 22, and the effect of decreasing the magnetic flux leakage at the upper side and the lateral side was exerted. Therefore, in particular, in a magnetic stimulation apparatus for home treatment, since decrease of the magnetic flux leakage was required for avoiding interference with peripheral equipment, it was conceived that use of the magnetic body 22 was effective. In addition, it was confirmed that the distribution of the induced currents of the brain was adjustable by changing the laminating method of the magnetic steel sheets in the magnetic body 22. Further, it was confirmed that, when the distribution range of the induced currents was expanded, the stimulation effects at the target point was not affected even if the coil was misaligned, in other words, robustness against misalignment was increased. This point was also useful for a home-treatment magnetic stimulation apparatus since a positioning mechanism could be simplified.

2.2 Numerical Analysis 2

2.2.1 Analysis Model

In order to obtain a shape model of the magnetic body having optimum stimulation efficiency by simulations, finite-element-analysis models close to an actual treatment environment were created. Although there were somewhat differences depending on analysis conditions in terms of the shape of the magnetic body, the setting of the air region, etc., analysis was carried out for basic analysis models having the configuration shown in schematic FIG. 35. In each of the analysis models, the distance between the coil 8 and the surface of the brain model 90 was set to 13 mm since the average distance from the skin of the actual human head to the gray matter of the brain was about 13 mm [Reference Document 23]. In addition, an air region was set to be larger than the brain or the magnetic body 22. This was for such a conceivable reason that, when the air region was too smaller than that of the brain or the magnetic body 22, an analysis magnetic field in an end region of the air region may deform and become different from an actually generated magnetic field. Further, the magnetic body 22 was disposed at the upper side of the coil 8. This was for excluding an invasive model which embeds the magnetic body 22 in the brain.

The analysis model was created by using "Femap with NX Nastran v 10.3.1" commercially sold by SIEMENS Kabushiki Kaisha. In creation of elements of the analysis model, the resolution was set to 1 to 5 mm.

2.2.2 Stimulation Coil

Figure 37A:
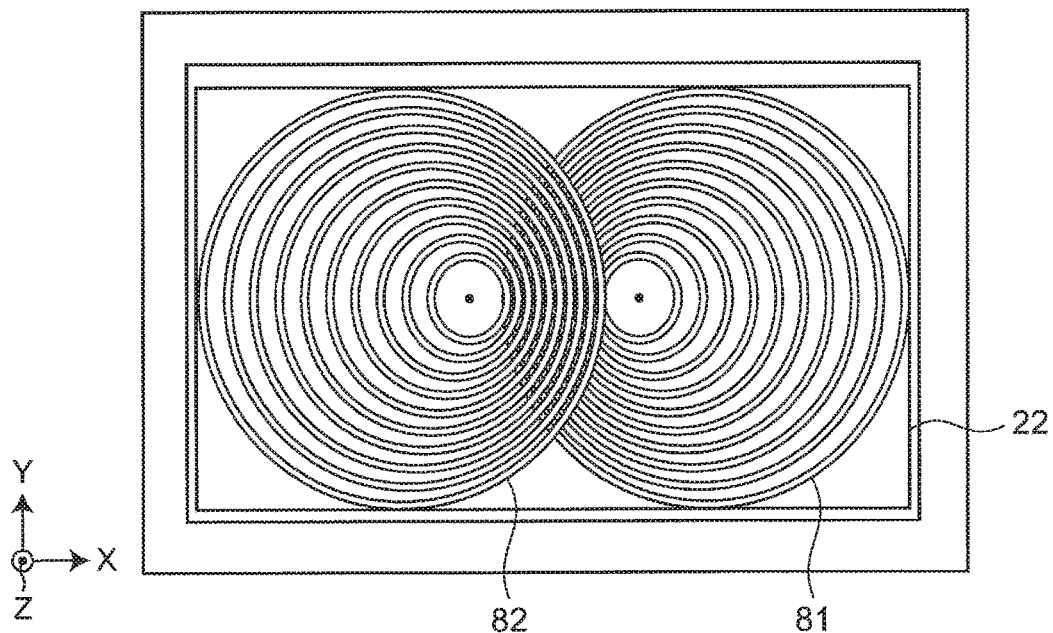
FIG. 37A is a plan view showing a model having a cuboidal magnetic body.
Figure 37B:
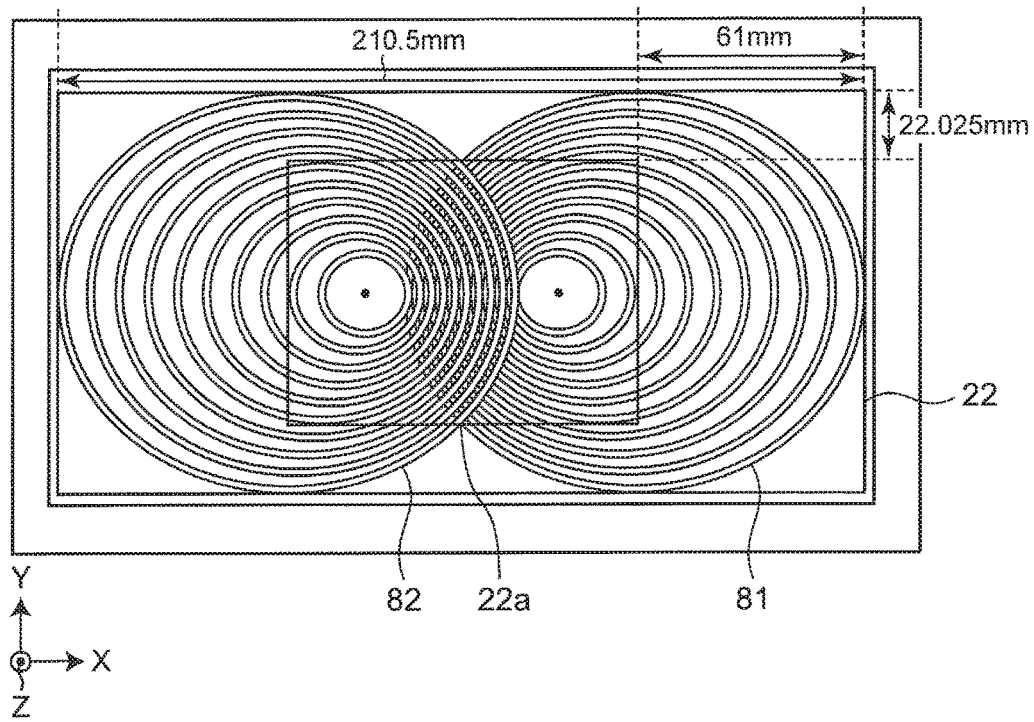
FIG. 37B is a plan view showing a model having a tetragonal-skeleton-shaped magnetic body.

In analysis, an eccentric figure-eight-shaped coil shown in FIGS. 37A and 37B was used. This coil was a coil developed by Sekino in 2012 and has such an advantageous effect that higher stimulation efficiency could be obtained, than that of a non-eccentric figure-eight-shaped coil. A pulse current of 3 kA with 3.15 kHz was applied in a counterclockwise direction to a left-side coil of FIGS. 37A and 37B. A pulse current of 3 kA with 3.15 kHz was applied in a clockwise direction to a right-side coil of FIGS. 37A and 37B.

2.2.3 Characteristics of Magnetic Body

A magnetic body (iron core) used in the analysis was made of iron of easily available ferromagnetic body. The relative magnetic permeability of the iron was set to 5,000, and the electric conductivity of the iron was set to 10,000,000 (S/m). The shape of the iron was cuboidal in consideration of processing readiness. In the case of the model expecting a magnetic body including a lamination of thin iron plates, the electric conductivity in the direction orthogonal to the laminating direction was set to zero (S/m) when electromagnetic fields were analyzed in order to allow the electric conductivity of the magnetic body to have directionality.

2.2.4 Infinite Element Method

The analysis of the finite element method was carried out by software of electric conductivity, Photo Series [Reference Document 28], which was commercially available from PHOTON Co., Ltd. In this case, eddy-current analysis was carried out by using frequency response analysis software of dynamic magnetic fields, PHOTO-EDDYjw [Reference Document 27]. This program calculated magnetic field distributions by the finite element method based on shape data, physical property values, boundary conditions, and input conditions of coil currents [Reference Documents 24 to 26].

2.2.5 Calculation of Induced Magnetic Field

The calculation equations of an induced electric field were described in "2.1.2 Analysis Method (a) Calculation Equations of Induced Electric Field". When the resolution was set to about 1 mm, the calculations of the analysis using the finite element method required about 20 hours. Femap was used for displaying the analysis results.

2.2.6 Designing of Magnetic Bodies Having High Stimulation Efficiency and Induced Electric Field Analysis 2.2.6.1 Changes in Stimulation Efficiency and Robustness Depending on Shapes of Magnetic Bodies The analysis was carried out to confirm that providing an eccentric figure-eight-shaped coil with an iron member serving as a ferromagnetic body concentrates a magnetic field, which spread in the upward direction from the coil, on the magnetic body and generated a strong magnetic field toward a brain model surface; and, in addition, analysis was carried out to confirm that newly creating an induced electric field on the brain surface by an induced current in the magnetic body improves stimulation efficiency. In addition, the robustness of coils equipped with various embodiments of magnetic bodies was evaluated.

(a) Analysis Method and Evaluation Standards

The analysis method was described above. The stimulation efficiency was evaluated by the average value of the induced electric field intensities in the central part of the brain model surface. Specifically, the average value of the induced electric field intensities of the elements within a sphere having a radius of 10 mm from the surface central part of the brain model shown in FIGS. 37A and 37B was used as an average induced electric field intensity.

Regarding the robustness, the region having a 70% intensity of the maximum value of the induced electric field in the central part of the brain model surface was used as an effective stimulation intensity, and half the values of the maximum lengths in the X-axis direction and the Y-axis direction of the region were used as effective stimulation distances of robustness evaluation indexes. Regarding the effective stimulation distance, the distance between the coordinates, which were on an X-axis-direction straight line and a Y-axis-direction straight line passing through the top-surface central part of the brain model, and had a 70% intensity of the induced electric field intensity at the top-surface central part of the brain model, and the top-surface central part of the brain model was set to "an effective stimulation distance".

(b) Analysis Model

A model with no magnetic body 22 (model 1), a model having a cuboidal magnetic body (model 2), and a model having a tetragonal-skeleton-shaped magnetic body including a tetragonal opening at a central part of a cuboidal magnetic body (model 3) were created. The coil and the disposition 22 of the magnetic body are described above. It was noted that, in each analysis, the model numbers were given from one. The dimensions of the model 2 and the model 3 are shown in FIGS. 37A and 37B. In the case of the tetragonal-skeleton-shaped magnetic body of FIG. 37B, it was conceived that the range of the opening was preferably a part in which induced currents flowed the most. Therefore, the size of an opening 22a was determined so that the centers of outermost-periphery conductive-wire parts of left/right circular coil parts 81 and 82 matched opening edges. The relative magnetic permeability of the magnetic body 22 was set to 5,000. The electric conductivity of the magnetic body was isotropic and set to 10,000,000 S/m. The distance between the bottom surface of the coil 8 and the top surface of the brain model 90 was set to 30 mm.

In the case of the cuboidal magnetic body of FIG. 37A, it was conceived that the induced current flowing in the magnetic body 22 became the largest in the central part of the magnetic body 22. This was for such a reason that, as was apparent from the Faraday's law of electromagnetic induction, since a change rate of magnetic flux density was the largest in the central part of the magnetic body 22, the induced electric field in the central part became large. In addition, since the electric conductivity was isotropic, the induced current also became large. In the case of the model 3 (FIG. 37B) from which the central part of the magnetic body 22 was removed, it was conceived that magnetic flux extended in the Y-axis direction passing through an upper part and a lower part of the tetragonal-skeleton-shaped magnetic body having a low magnetic resistance. Therefore, it was conceived that magnetic field leakage was small in the tetragonal-skeleton-shaped magnetic body. On the other hand, in the case of the cuboidal magnetic body, the induced current of the central part of the magnetic body 22 induced an electric field on the surface central part of the brain model 90. On the other hand, such an electric field was not induced in the case of the tetragonal-skeleton-shaped magnetic body. Therefore, it was conceived that the model 3 having the tetragonal-skeleton-shaped magnetic body obtained the highest stimulation efficiency.

(c) Analysis Results

Figure 38A:
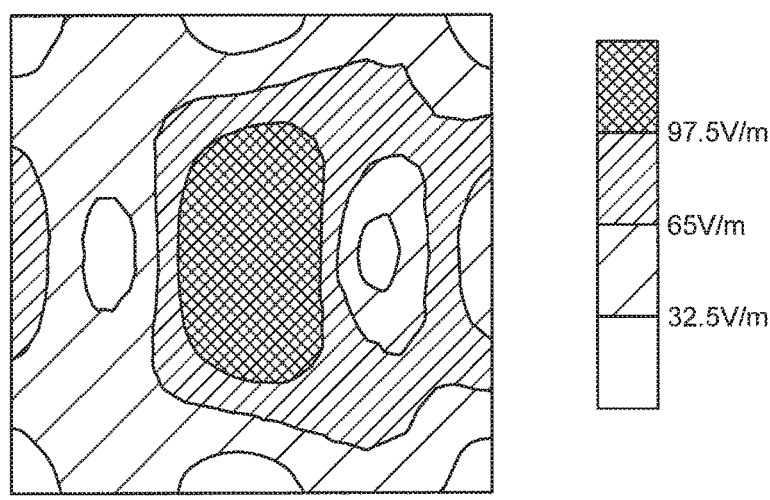
FIG. 38A is a contour graph showing induced electric field intensities at a brain model surface.
Figure 38B:
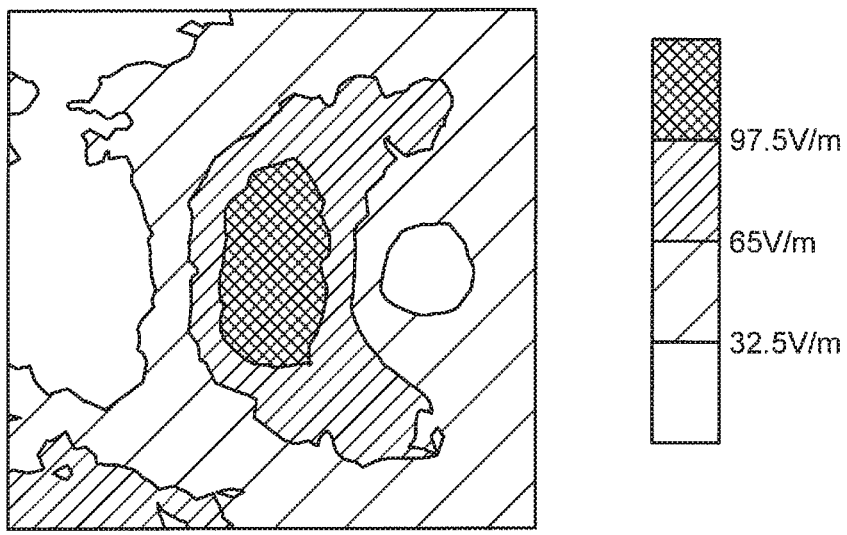
FIG. 38B is a contour graph showing induced electric field intensities at a brain model surface.
Figure 38C:
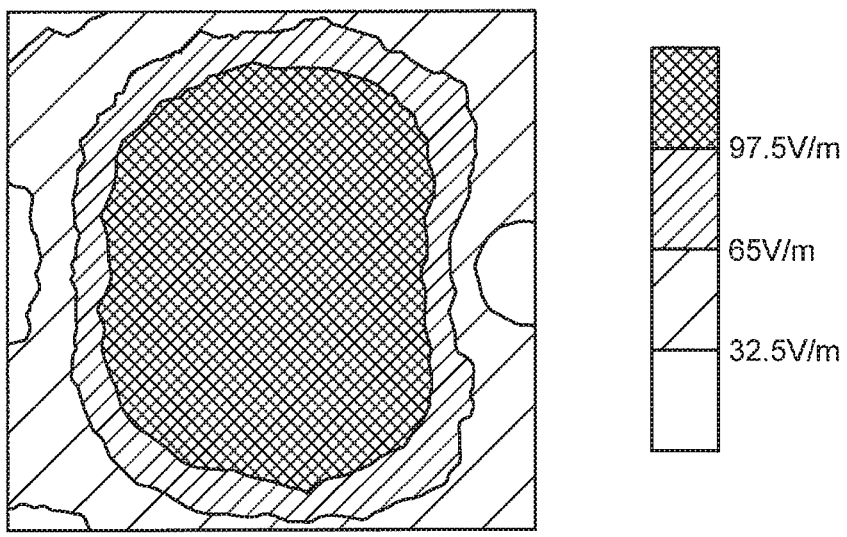
FIG. 38C is a contour graph showing induced electric field intensities at a brain model surface.

FIG. 38A to FIG. 38C show the analysis results of the induced electric field intensities on the surfaces of the brain models 90 of above described models 1 to 3. According to the analysis results, the brain-surface average induced-electric field intensity of the model 1 (FIG. 38A) with no magnetic body 22 was 69.3 V/m, the surface average induced-electric field intensity of the model 2 (FIG. 38B) having the cuboidal magnetic body 22 was 49.5 V/m, and the surface average induced-electric field intensity of the model 3 (FIG. 38C) having the skeleton-shaped magnetic body 22 was 120 V/m.

Figure 39:
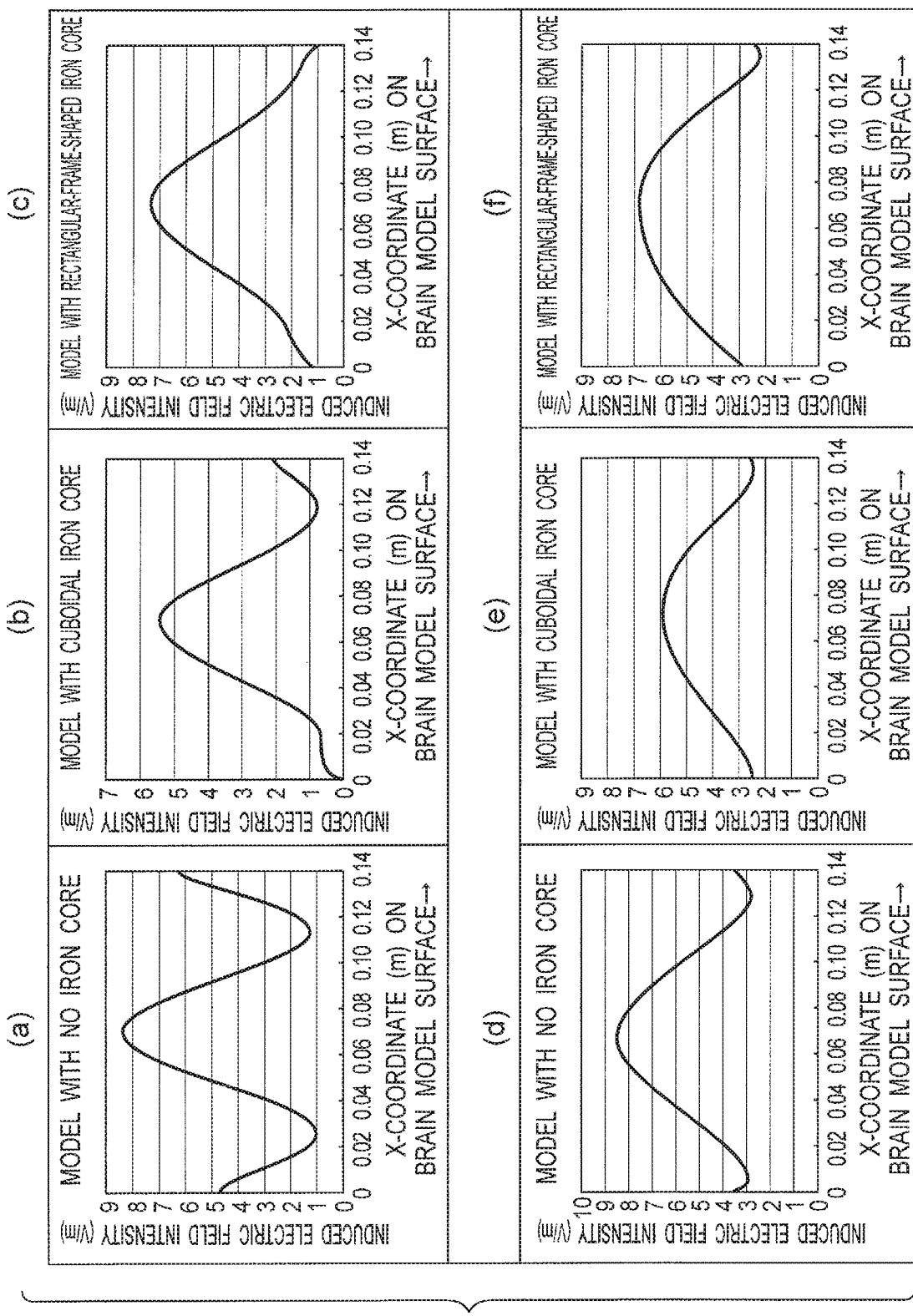
FIG. 39 is a graph showing induced electric field intensity distributions in an X-axis direction and a Y-axis direction passing through a brain-surface central part.

FIG. 39 shows evaluation results of stimulation robustness of each of the models 1 to 3. Referring to FIGS. 39(a) and 39(d), in the case of the model 1 with no magnetic body 22, the X-axis-direction effective stimulation distance was 0.041 m, and the Y-axis-direction effective stimulation distance was 0.0678 m. Referring to FIGS. 39(b) and 39(e), in the case of the model 2 having the cuboidal magnetic body 22, the X-axis-direction effective stimulation distance was 0.0304 m, and the Y-axis-direction effective stimulation distance was 0.0735 m. Referring to FIGS. 39(c) and 39(f) in the case of the model 3 having the tetragonal-skeleton-shaped magnetic body 22, the X-axis-direction effective stimulation distance was 0.303 m, and the Y-axis-direction effective stimulation distance was 0.0689 m.

Regarding the stimulation efficiency, the stimulation efficiency of the model 3 was significantly improved. Specifically, the stimulation efficiency of the model 3 was 173% of the stimulation efficiency of the model 1. However, the stimulation efficiency of the model 2 was about 71% of the stimulation efficiency of the model 1. Regarding the robustness of stimulation, there were no notable differences among the models.

The reason why the model 3 having the tetragonal-skeleton-shaped magnetic body 22 obtained the higher stimulation efficiency than the model 1 with no magnetic body 22 was conceivably because the magnetic field of the coil 8 was concentrated on the magnetic body 22 by the presence of the ferromagnetic body (iron). In addition, the reason why the model 3 having the tetragonal-skeleton-shaped magnetic body 22 obtained the higher stimulation efficiency than that of the model 2 having the cuboidal magnetic body 22 was conceivably for the following reasons:

the induced current flowing through the central part of the magnetic body 22 generated an electric field, which was in the opposite direction of the electric field of the coil 8, on the surface of the brain model 90 in the case of the cuboidal magnetic body 22; and on the other hand, such an electric field in the opposite direction was not generated in the case of the tetragonal-skeleton-shaped magnetic body 22.

More electromagnetic description will be added about the high stimulation efficiency of the model 3 as follows: since the part in which the magnetic body was present significantly decreases magnetic resistance, the magnetic flux approximately passed through the magnetic body, and could more efficiently send a magnetic field to the brain surface.

Figure 40A:
FIG. 40A is a contour graph showing an induced current density (X direction components) on the surface of the cuboidal magnetic body.
Figure 40B:
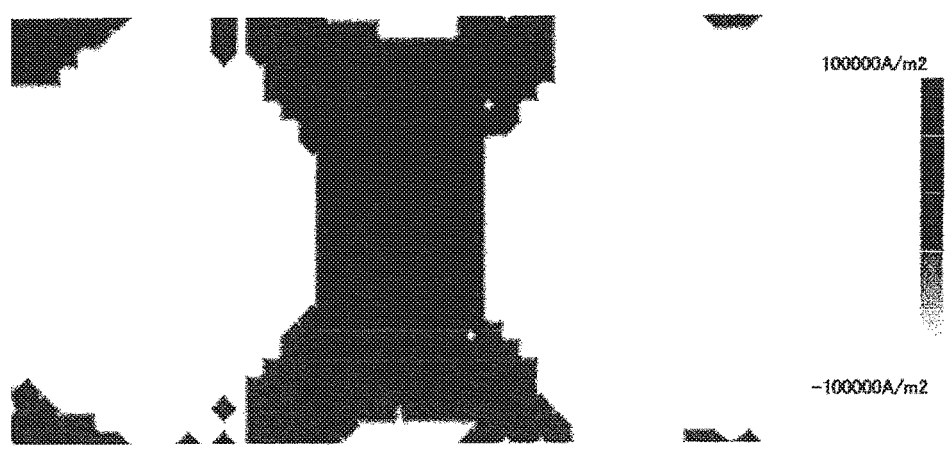
FIG. 40B is a contour graph showing an induced current density (Y direction components) on the surface of the cuboidal magnetic body.

FIG. 40A is a contour graph showing induced current densities (X direction components) on the surface of the cuboidal magnetic body, and FIG. 40B is a contour graph showing induced current densities (Y direction components) on the surface of the cuboidal magnetic body. As is understood from FIG. 40A, the Y-axis-direction component of the current density had a strong intensity in a Y+ direction in the central part of the magnetic body 22, and this induces an induced electric field in the opposite direction (in other words, Y direction) of the induced electric field created by the coil 8 on the surface of the brain model 90. On the other hand, as shown in FIG. 40B, in the case of the tetragonal-skeleton-shaped magnetic body, since an induced current in the Y+ direction is not induced in the removed central part, the induced electric field induced in the central part of the brain model 90 by the coil 8 was not attenuated.

Figure 41:
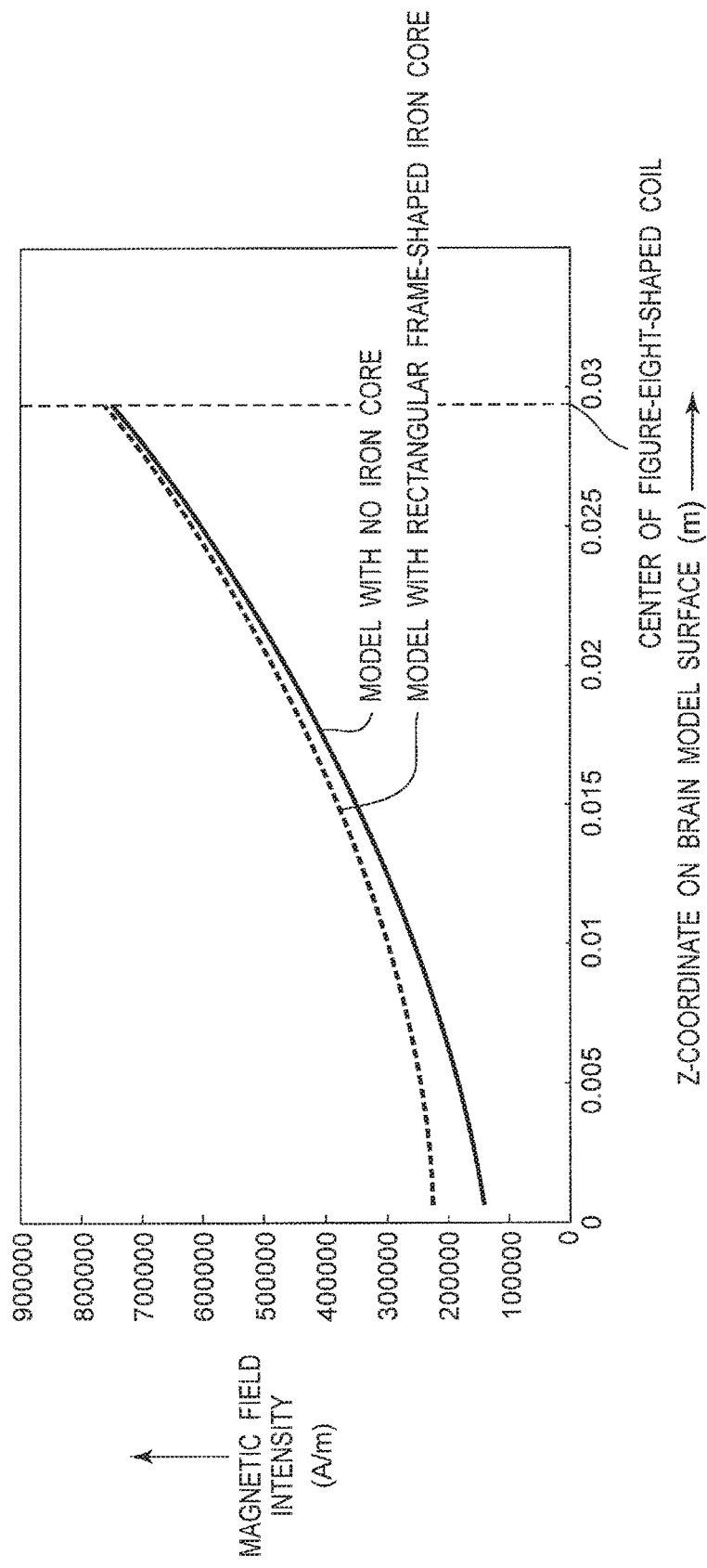
FIG. 41 is a graph showing magnetic-field intensities in a Z-axis direction.

FIG. 41 shows an approximate graph of magnetic intensity parts on a line extending in the Z direction from the magnetic body toward the brain model through the coil central part of the coil having the tetragonal-skeleton-shaped magnetic body. In FIG. 41, "0" of the Z coordinate notes the brain surface, and FIG. 41 shows a magnetic-field density on the Z direction line penetrating through the coil center. According to FIG. 41, it can be understood that, as compared with the model with no magnetic body 22, a strong magnetic field is generated in the Z-direction in the model having the tetragonal-skeleton-shaped magnetic body 22.

2.2.6.2 Changes in Stimulation Efficiency and Robustness Depending on Electric Characteristics of Magnetic Body Influence exerted on stimulation efficiency by the electric characteristics of the magnetic bodies, in other words, the directions of induced currents was studied.

The magnetic body 22 was configured by laminating a plurality of magnetic plates, and the flowing directions of the induced currents were limited by changing the laminating direction thereof. As is apparent from the above described analysis results, when the magnetic plates were laminated in the Y-axis direction, the induced currents do not flow in the same direction. Therefore, it was conceived that, in the model having the tetragonal-skeleton-shaped magnetic body 22, the induced electric field generated in the brain-surface central part by the coil is not affected. In addition, it was conceived that, when both of the end parts of a magnetic body in the X-axis direction were laminated in the X-axis direction, the induced current flowing in the direction of the induced eddy current on the brain model surface by the coil could be caused to flow in the magnetic body.

The study was carried out only for cuboidal magnetic bodies. This was for the following reasons: the induced current flowing in the central part of the magnetic body could be approximately controlled by adjusting the laminating direction of the magnetic plates, and, in addition, when an entire model was viewed as a magnetic circuit, the magnetic resistance of the cuboidal magnetic body was smaller than that of the tetragonal-skeleton-shaped magnetic body.

(a) Analysis Models

Four analysis models having cuboidal magnetic bodies were prepared as follows, more specifically:

an X-lamination model 1 in which magnetic plates were laminated in the X-axis direction (model in which induced currents flow along YZ-surfaces);

a Y-lamination model 2 in which magnetic plates were laminated in the Y-axis direction (model in which induced currents flow along XZ-planes);

an XY-lamination model 3 in which magnetic plates were laminated in the X-axis direction and the Y-axis direction; and a no-magnetic-body model 4 without magnetic bodies.

Figure 42:
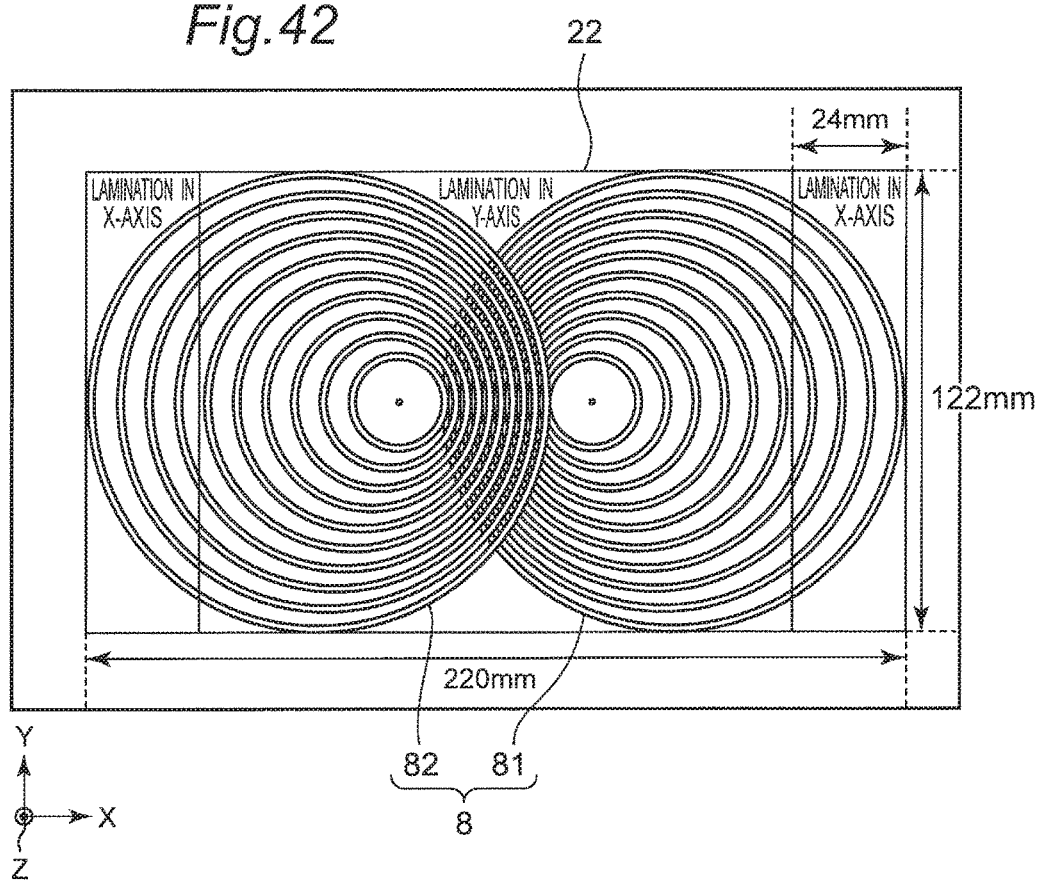
FIG. 42 is a plan view showing a model combining X-axis laminates and a Y-axis laminate.
Figure 43A:
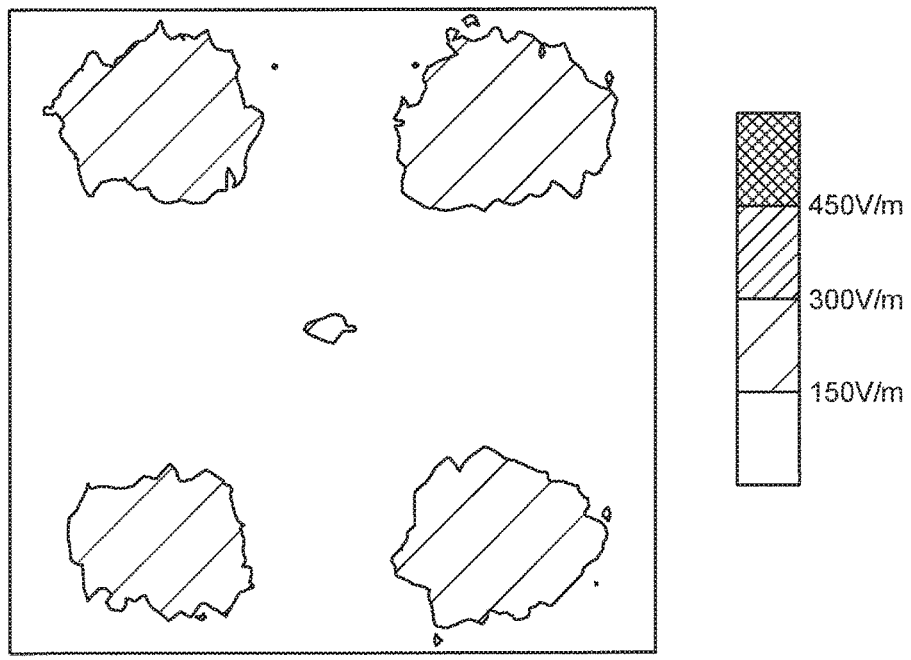
FIG. 43A is a contour graph showing induced electric field intensities of a brain model surface.
Figure 43D:
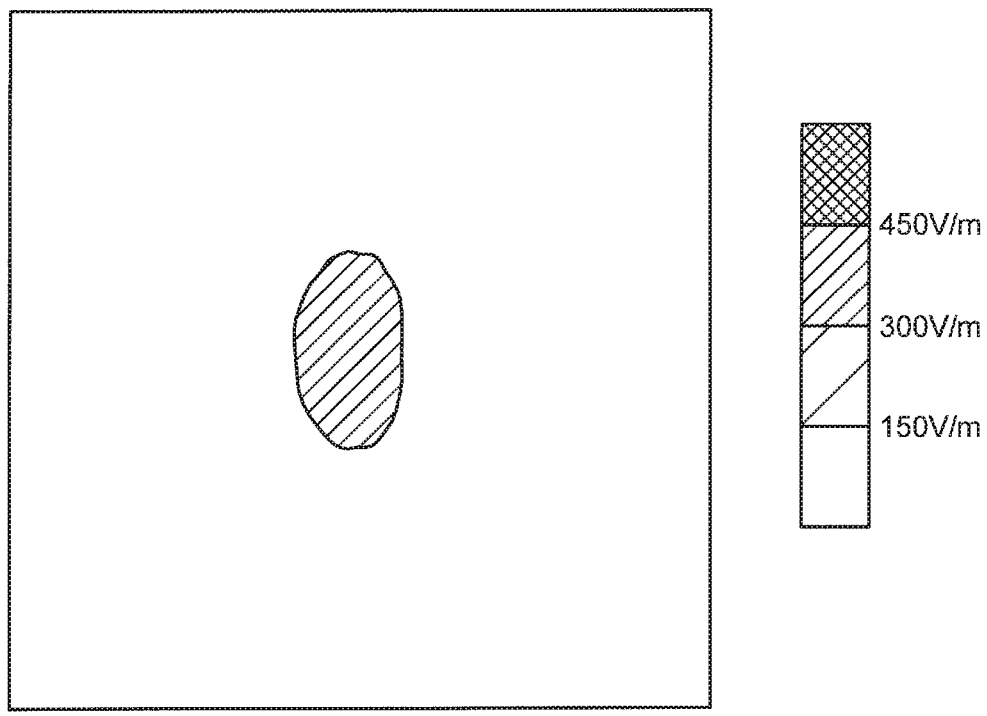
FIG. 43D is a contour graph showing induced electric field intensities of a brain model surface.

In the XY-lamination model 3, as shown in FIG. 42, the magnetic plates were laminated in the X-axis direction in X-axis-direction both-end regions, and the magnetic plates were laminated in the Y-axis direction in an intermediate region between both the end regions. In this XY lamination model 3, it was conceived that the induced currents in the opposite directions of the induced currents, which were generated in the brain by the single eccentric figure-eight-shaped coil 8, flowed in the magnetic body; and, as a result, the induced currents generated an electric field in the central part of the brain surface in the same direction as the direction in which the induced electric field generated by the eccentric figure-eight-shaped coil 8, and stimulation efficiency was improved. In each model, the distance between the surface of the brain model 90 and the bottom surface of the coil 8 was set to 13 mm, which was approximately the same as that in an actual stimulation environment.

(b) Analysis Results

FIG. 43A to FIG. 43D show analysis results of average induced electric field intensities at target parts of the surfaces of the brain models 90 for the four analysis models 1 to 4, respectively. According to the analysis results, the average induced electric field intensity of the X-lamination model 1 was 120 V/m, the average induced electric field intensity of the Y-lamination model 2 was 415 V/m, the average induced electric field intensity of the XY-lamination model 3 was 502 V/m, and the average induced electric field intensity of the no-magnetic-body model 4 was 139 V/m.

Figure 44:
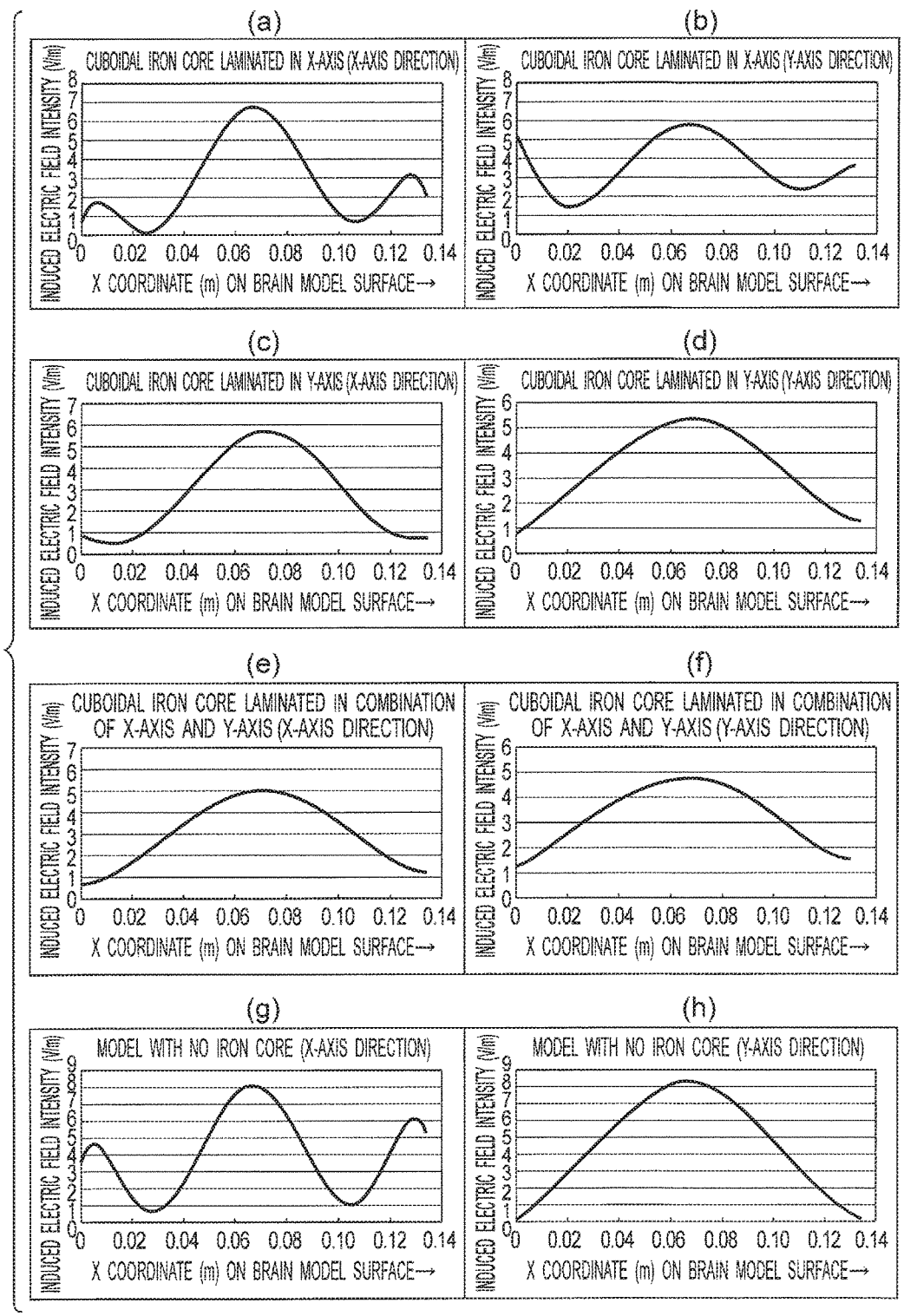
FIG. 44 is a graph showing induced electric field intensity distributions in the X-axis direction and the Y-axis direction passing through a brain-surface central part.

FIG. 44 show evaluation results of robustness. Referring to FIGS. 44(*a*) and 44(*b*), the X-axis-direction effective stimulation distance and the Y-axis-direction effective stimulation distance of the X-axis lamination model 1 were 0.0242 m and 0.0644 m, respectively. Referring to FIGS. 44(*c*) and 44(*d*), the X-axis-direction effective stimulation distance and the Y-axis-direction effective stimulation distance of the Y-axis lamination model 2 were 0.0346 m and 0.0649 m, respectively. Referring to FIGS. 44(*e*) and 44(*f*), the X-axis-direction effective stimulation distance and the Y-axis-direction effective stimulation distance of the XY-axis lamination model 3 were 0.0607 m and 0.0697 m, respectively. Referring to FIGS. 44(*g*) and 44(*h*), the X-axis-direction effective stimulation distance and the Y-axis-direction effective stimulation distance of the no-magnetic-body model 4 were 0.0327 m and 0.0598 m, respectively.

In consideration of the fact that twitching of fingers was observed when an induced current density of about 18 A/m$^2$ was applied to a vicinity of the primary motor cortex of the brain in past clinical test results, when a stimulation part is the gray matter (the electric conductivity of the gray matter was assumed to be 0.11 S/m), it was conceived that the induced electric field intensity with which stimulation effects were obtained is about 164 V/m according to the relation of j=σE. Therefore, it was confirmed that the lamination model 3 had the stimulation intensity necessary for treatment.

Figure 45:
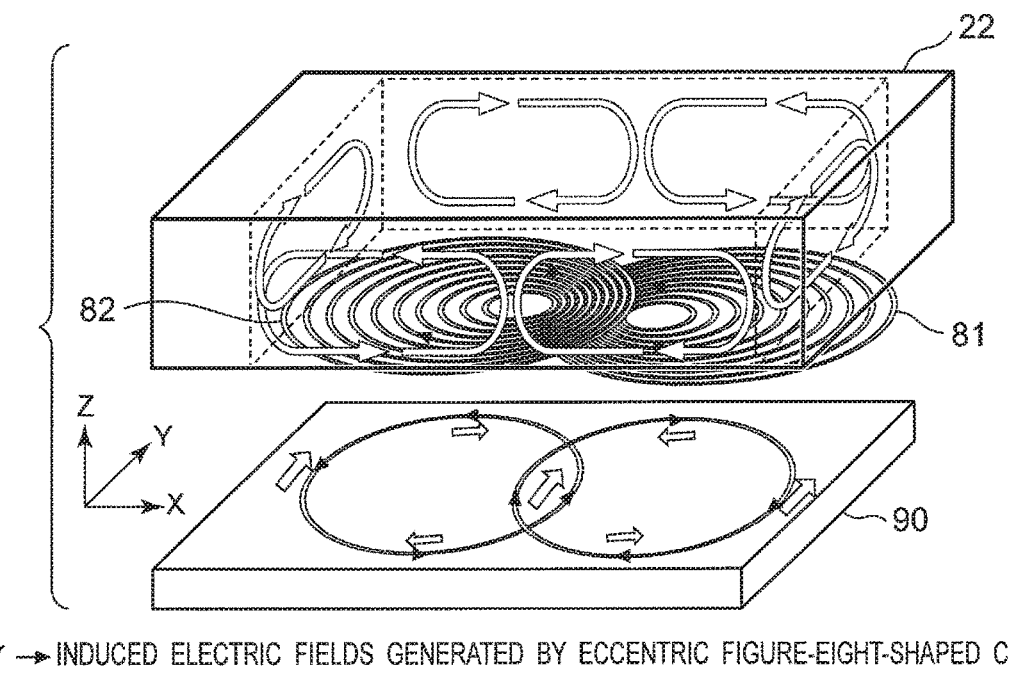
FIG. 45 is a perspective view showing an induced electric field distribution in a magnetic body of an XY-lamination model and induced electric fields on the brain surface.

According to the analysis results of the brain-surface-induced electric fields shown in FIG. 44, it can be understood that the XY-lamination model 3 shows the highest stimulation efficiency. Although the Y-lamination model 2 showed the high stimulation efficiency which was about two to three times the stimulation efficiency of the no-magnetic-body model 4, downward induced electric fields acted in both the end regions of the brain model. In the XY-lamination model 3, the induced currents shown in FIG. 45 flowed in the magnetic body, and, as a result, in the brain-surface central part, induced electric fields were generated in the same directions as the directions of the induced electric fields generated by the eccentric figure-eight-shaped coil. It was conceived that high induced electric field intensities were obtained in the central part serving as the target part for such reasons.

Since the current flowing in the magnetic body of the X-lamination model 1 was the largest, it was conceived that such a phenomenon occurred that the induced electric field intensity in the central part of the brain-model top surface decreased.

Since the largest magnetic field penetrating through the central part of the magnetic body was generated according to the Faraday's law in all of the models, it was conceived that the largest electric field was induced thereto. However, since the induced electric field had the Y-axis-direction component which was considerably larger than the X-axis-direction component, the induced current in the Y-axis direction did not flow in the magnetic body of the Y-lamination model 2. Therefore, the induced current generated in the magnetic body of the X-lamination model 1 in which the second largest change rate of magnetic field was generated became the largest.

Figure 46:
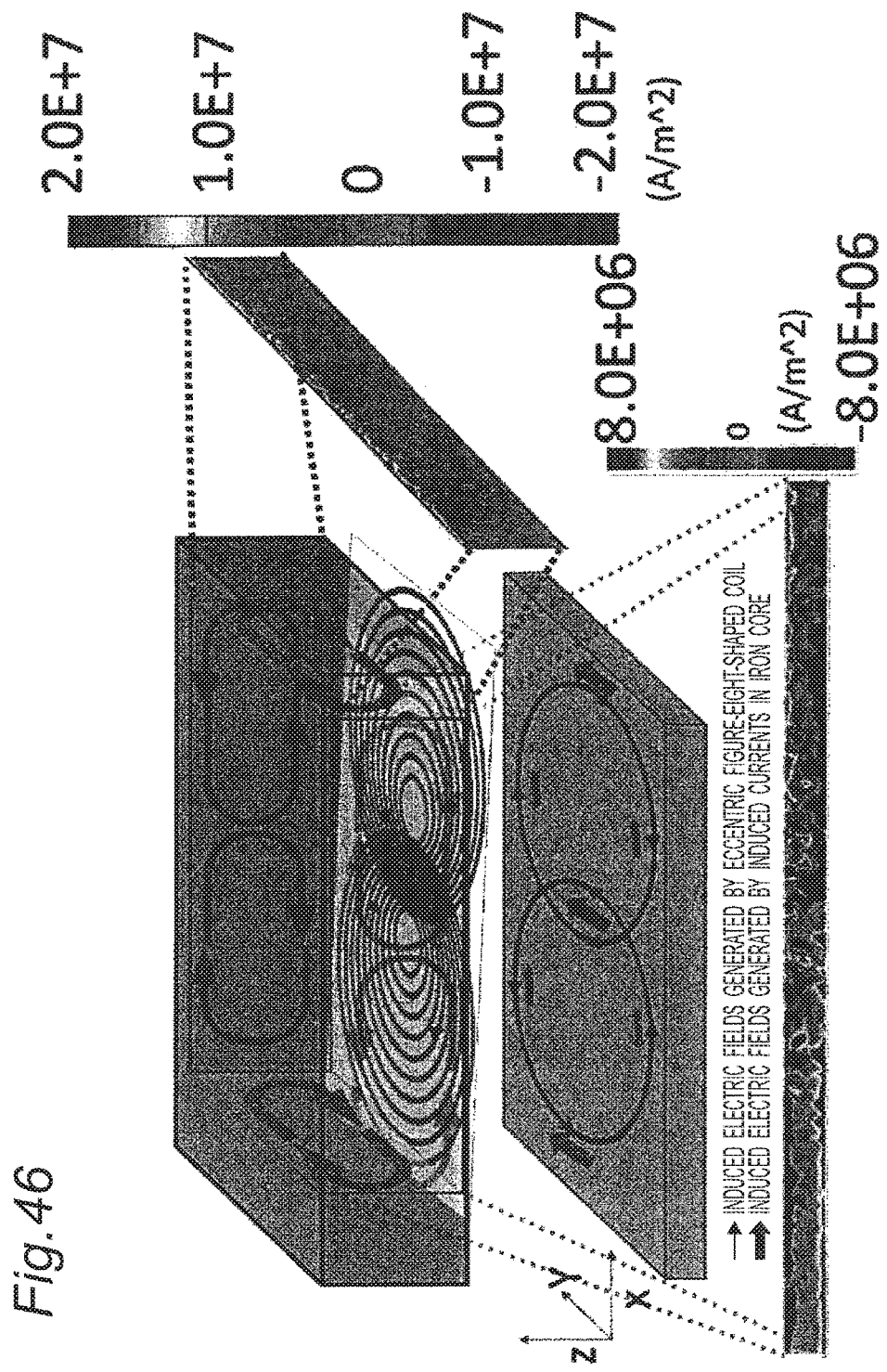
FIG. 46 is a photographic image of a perspective view showing analysis results of the induced current distribution in the magnetic body of the XY-lamination model.

FIG. 46 shows a photographic image of the analysis results of the induced current densities in the magnetic body. As was apparent from FIG. 46, it could be confirmed that the induced currents shown in FIG. 45 flowed in the magnetic body.

Regarding the robustness, the robustness of the Y-lamination model 2 and the XY-lamination model 3 improved by about 10% from that of the no-magnetic-body model 4. In addition, in the case of the XY-lamination model 3, the effective stimulation distance increased by about two times in the X-axis direction. It was conceived that the induced electric field generated by the eccentric figure-eight-shaped coil had extremely high locality, the induced electric field in the X-axis direction was induced on the brain surface by providing the Y-axis-direction laminated magnetic body; and, as a result, the induced electric field expanded as a whole in the X-axis direction. In the case of the XY-lamination model 3, due to the combination effect thereof, it was conceived that the strong induced electric fields generated in both the end parts of the brain surface caused the induced electric field as a whole to expand in the X-axis direction.

2.2.6.3 Changes in Stimulation Efficiency Depending on Combinations of the Shapes of Magnetic Bodies and Electric Characteristics Based on the above described studies of the changes in the stimulation efficiency depending on the shapes of the magnetic bodies and the changes in stimulation efficiency depending on the electric characteristics of the magnetic bodies, the configuration of the magnetic body having optimum stimulation efficiency was studied. As described above, it was confirmed that the magnetic bodies collected the magnetic fields of the Z+ direction to generate a larger magnetic field toward the brain surface, depending on the shapes of the magnetic bodies. However, in the vicinity of the outermost-periphery conductive-wire part of the eccentric figure-eight-shaped coil, the induced currents induced by the coil were small, and the magnetic fields generated by the coil were also weak. Therefore, it was conceived that, even if the Y-axis-direction length of the magnetic body was shorter than the length of the coil in the same direction, the stimulation efficiency was not affected.

(a) Analysis Models

Figure 47A:
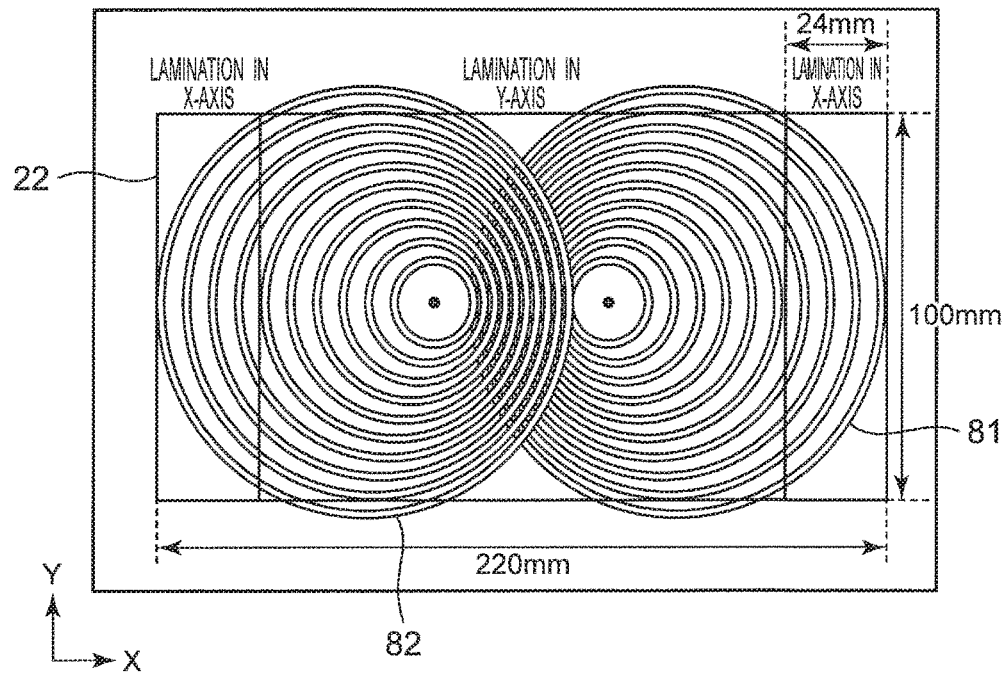
FIG. 47A is a plan view showing an analysis model.
Figure 47B:
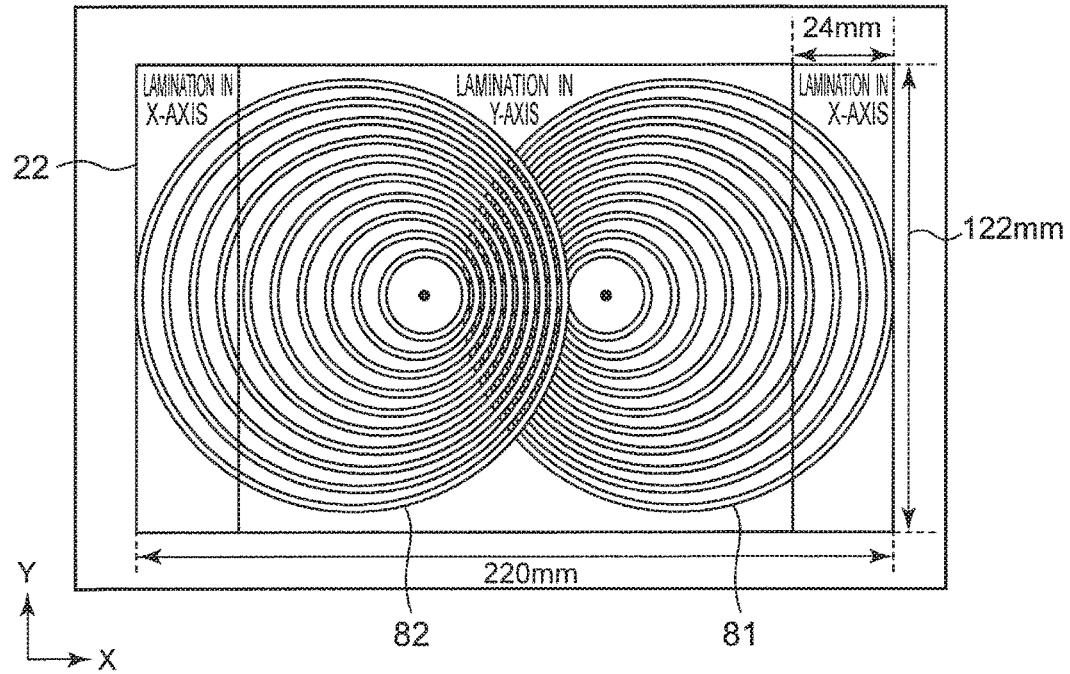
FIG. 47B is a plan view showing an analysis model.

For analysis, three XY-lamination models were created, in which the sizes of the magnetic bodies were different from each other as follows:

220×122×10 mm (model 1 (FIG. 47B));
220×100×10 mm (model 2 (FIG. 47A)); and
220×140×10 mm (model 3).

Such models were prepared for the following reasons:

it was conceived that the cuboidal magnetic body 22 having the size covering the entirety of the eccentric figure-eight-shaped coil 8 had the best stimulation efficiency since the magnetic body concentrates almost all magnetic fields generated by the coil 8; in addition, it was conceived that the XY-lamination model had the best stimulation efficiency as described above; and, further, it was conceived that an optimum magnetic shape could be obtained by comparing with such magnetic bodies.

(b) Analysis Results

According to the results of analyzing average induced electric field intensities in the target parts of the brain model surfaces about the three analysis models 1, 2, and 3, the average induced electric field intensity of the model 1 was 502 V/m, the average induced electric field intensity of the model 2 was 507 V/m, and the average induced electric field intensity of the model 3 was 506 V/m. Therefore, it was confirmed that the model 2 having the shortest X direction length (100 mm) was the optimum.

Figure 48:
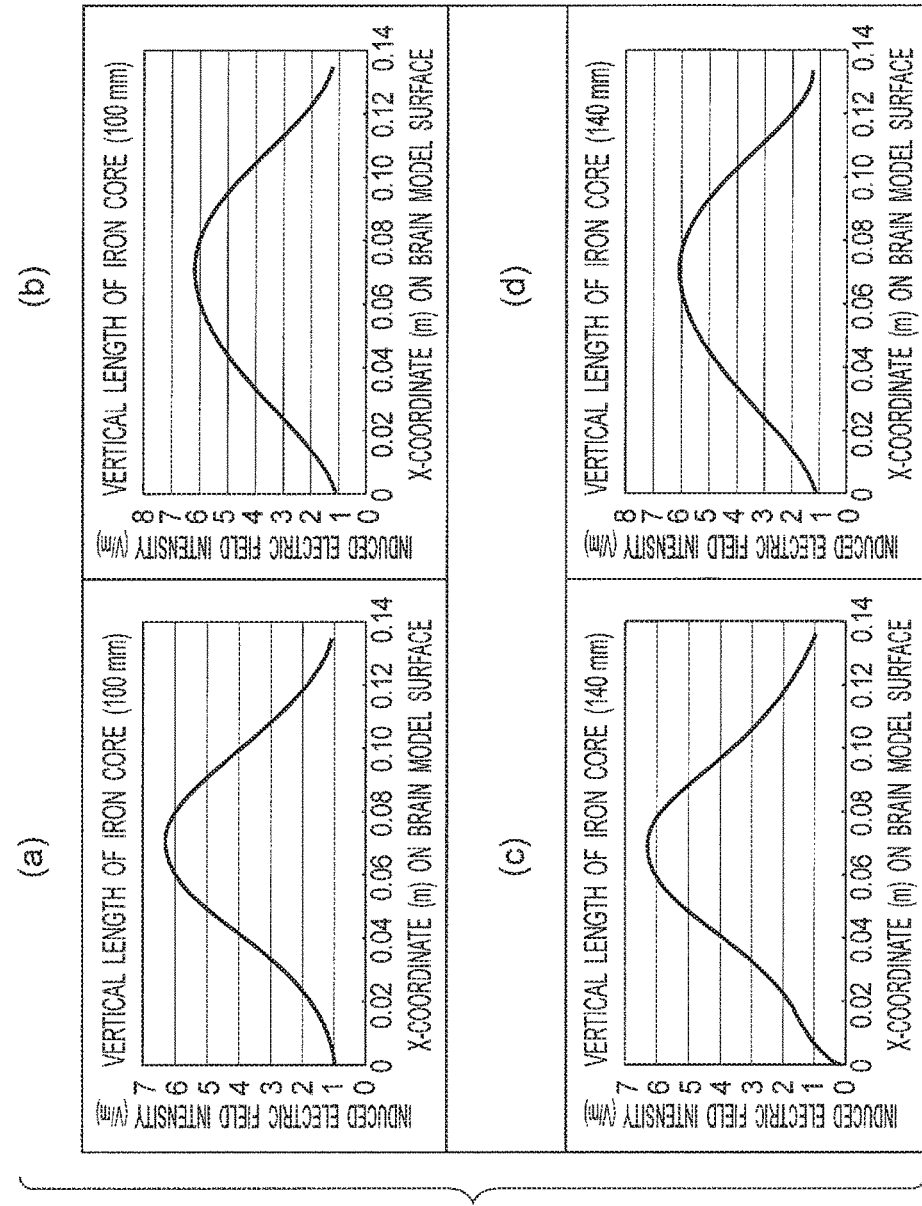
FIG. 48 is a graph showing induced electric field intensity distributions in the X-axis direction and the Y-axis direction passing through the brain-surface central part.

FIG. 48 show results of evaluating the robustness of the models 1 to 3. The X-axis-direction effective stimulation distance and the Y-axis-direction effective stimulation distance of the model 1 of FIG. 47B were 0.0607 m and 0.0697 m, respectively. The X-axis-direction effective stimulation distance and the Y-axis-direction effective stimulation distance of the model 2 of FIG. 47A were 0.0529 m and 0.0666 m, respectively. The X-axis-direction effective stimulation distance and the Y-axis-direction effective stimulation distance of the model 3 were 0.0526 m and 0.0669 m, respectively.

As described above, the models 1, 2, and 3 exhibited equivalent values about the stimulation efficiency. This means that even the model 2 having the Y-axis-direction length of 100 mm could obtain the equivalent stimulation efficiency as those of the models 1 and 3 having the longer Y-axis-direction lengths. There were no significant differences among the models 1, 2, and 3 about the stimulation robustness in the Y-axis direction. About the stimulation robustness in the X-axis direction, the model 1 had the largest stimulation range, and the stimulation ranges of other models 1 and 3 were smaller by about 13% than that. However, in consideration of the permissible error in the X-axis direction (about 25 mm), misalignment errors of a positioning helmet model, etc., it could be said that the magnetic body of the model 2 having the shortest Y-axis-direction length of 100 mm had the optimum stimulation efficiency.

2.2.6.4 Optimum Thickness of Laminated Magnetic Body for Use in Home Coil

From a viewpoint of obtaining the stimulation coil 8 having a weight appropriate for home treatment, the thickness of the magnetic body capable of sufficiently concentrating the magnetic flux generated by the coil and obtaining necessary stimulation efficiency was studied.

Figure 49:
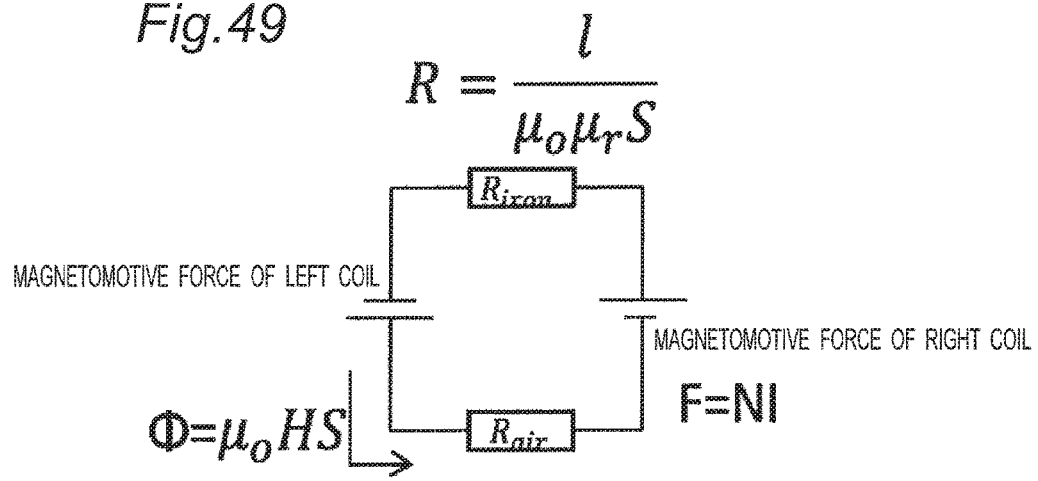
FIG. 49 is a circuit diagram showing a magnetic equivalent circuit of an analysis model.

(a) Thickness of Magnetic Body Capable of Concentrating Magnetic Flux Generated by Coil In terms of handling of the coil 8, the lighter the magnetic body, the more it was preferred. However, when the magnetic body was too thin, the magnetic force lines generated by the coil 8 could not be concentrated in the magnetic body 22. Therefore, the thickness of the magnetic body capable of concentrating almost all the magnetic flux lines generated by the coil 8 was approximately calculated about three Y-axis lamination models (the models 1, 2, and 3, in which the thicknesses of the magnetic bodies were 2 mm, 5 mm, and 10 mm). In the calculations, each model was replaced by an equivalent magnetic circuit of FIG. 49. In FIG. 49, "S" represents the area of a YZ cross section of the magnetic body 22.

Magnetic flux Φ obtained by the equivalent circuit of FIG. 49 is given by Equation (10). In Equation (10), "$r_1, \ldots, r_{10}$" (in the case of a coil with 10 turns) are average radii of respective conductive-wire loops of the eccentric figure-eight-shaped coil. In this case, a magnetic field H is expressed by the following equation.

$$\overline{H} = \left(\frac{I}{2r_1} + \frac{I}{2r_2} + \ldots + \frac{I}{2r_{10}}\right) \times \frac{1}{\sqrt{2}} = 4 \times 10^5 \quad (10)$$

Next, the equation of the equivalent circuit can be expressed as the following Equation (11).

$$NI + NI = \left\{\left(\frac{I}{2r_1} + \frac{I}{2r_2} + \ldots + \frac{I}{2r_{10}}\right) \times \frac{1}{\sqrt{2}}\right\} \times \left\{\frac{I}{\mu_0 \mu_r S} + \frac{I}{\mu_0 \mu_r S_{air}}\right\} \quad (11)$$

In this case, "N" is the number of turns of the coil 8, and "NI" is the electromotive force. The current flowing in the circuit is 3 kA, and N=10. When the cross-sectional area of air is 100 cm×100 cm=1 m², the obtained cross-sectional area is S=2.937. In this case, since the Y-axis-direction length of the magnetic body 22 in the YZ cross section is 120 mm, the thickness of the magnetic body 22 capable of concentrating all the magnetic force lines, which are generated by the coil, into the magnetic body 22 is about 1.5 mm (=2.937/120).

(b) Analysis Models and Evaluation Method

Three Y-lamination models (models 1, 2, and 3 in which the thicknesses of the magnetic bodies were 2 mm, 5 mm, and 10 mm, respectively) were created, and brain-surface-induced electric field intensities of the models were calculated for comparison.

(c) Analysis Results

According to the analysis results thereof, the average induced electric field intensities in the brain-surface central parts of the models 1, 2, and 3 were 390 V/m, 380 V/m, and 415 V/m, respectively. As shown by these analysis results, it was found out that the thicknesses of the magnetic bodies did not largely affect the average values of the brain-surface-induced electric fields, and all the magnetic flux generated by the coil 8 was concentrated even in the case in which the thickness of the magnetic body 22 was 2 mm. The weight of the magnetic body 22 having a thickness of 2 mm is 40 grams, and it was conceived that the weight is not problematic in actual use.

When the thickness of the magnetic body 22 was 10 mm, slightly high stimulation efficiency was obtained. The reason thereof was as follows: the induced currents flowing in the top surface of the magnetic body had the act of weakening the induced electric field generated on the brain surface by the coil, however, the intensity of the induced electric field was inversely proportional to the square of the distance according to the Biot-Savart law.

Since this effect was the weakest in the model 3 (the model in which the thickness of the magnetic body was 10 mm) in which the distance between the top surface of the magnetic body 22 and the surface of the brain model 90 was the longest, the stimulation efficiency thereof was conceived to be the highest.

The X-axis-direction effective stimulation distance and the Y-axis-direction effective stimulation distance of the model 1 were 0.0490 m and 0.0606 m, respectively. The X-axis-direction effective stimulation distance and the Y-axis-direction effective stimulation distance of the model 2 were 0.0485 m and 0.0590 m, respectively. The X-axis-direction effective stimulation distance in the X direction and the Y-axis-direction effective stimulation distance of the model 3 were 0.0461 m and 0.0613 m, respectively.

2.2.6.5 Characteristic Evaluation of Dome-Shaped Coils (a) Optimum Stimulation Robustness for Home Transcranial Magnetic Stimulation Apparatus A helmet-type positioning system which enables adjustment of the coil position by a patient himself/herself has been studied. Such a self-adjustment-type system is desired to have the robustness capable of permitting a misalignment error of about 20 to 30 mm. In addition, it is important to find out the relations between magnetic body characteristics and robustness in advance. Therefore, various magnetic body models were prepared, and stimulation robustness was evaluated for each of them.

(b) Stimulation Robustness of Dome-Shaped Coils Having Magnetic Bodies

The robustness of a model (FIGS. 51A and 51B) in which a dome-shaped coil (See FIGS. 50A and 50B) proposed in Patent Document 3 was provided with a magnetic body was evaluated.

(c) Analysis Models

Figure 50A:
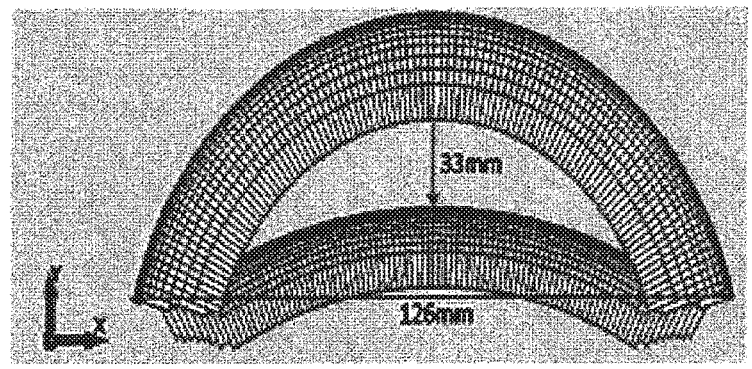
FIG. 50A is a perspective view showing a dome-shaped coil used in analysis.
Figure 50B:
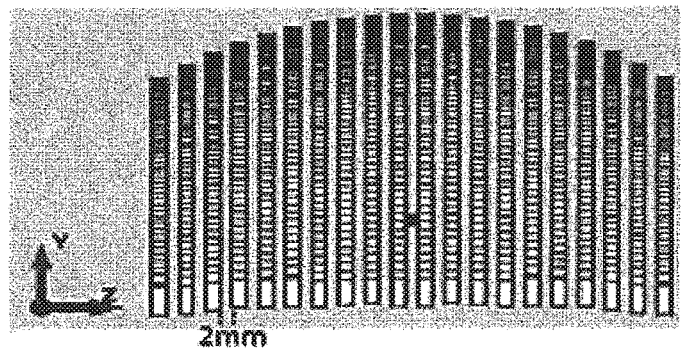
FIG. 50B is a lateral view showing the dome-shaped coil used in the analysis.

About the model (FIG. 51A and FIG. 51B) in which an X-axis-direction laminated magnetic body was disposed in a hollow part of the dome-shaped coil shown in FIGS. 50A and 50B, brain-surface-induced electric fields and stimulation robustness in the X-axis direction and the Y-axis direction were evaluated. In this case, the following models were prepared:

a dome-shaped coil model with no magnetic body (model 1);

a dome-shaped coil model having a magnetic body having a thickness of 4 mm (model 2); and a dome-shaped coil model having a magnetic body having a thickness of 12 mm (model 3).

Figure 51A:
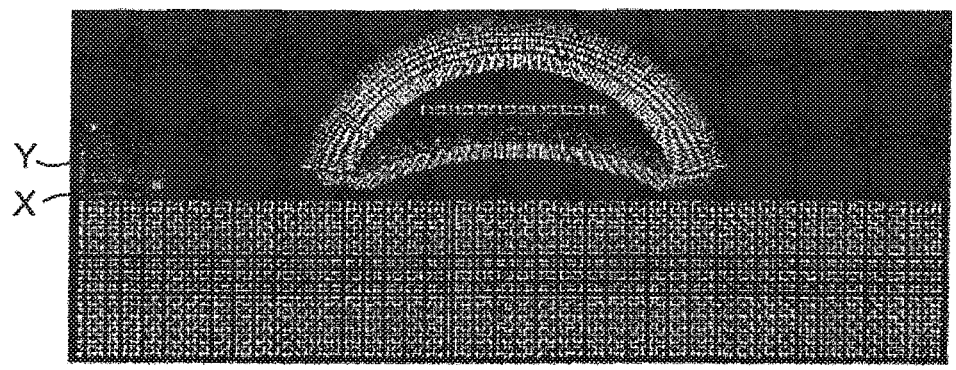
FIG. 51A is a perspective view showing the dome-shaped coil used in the analysis.
Figure 51B:
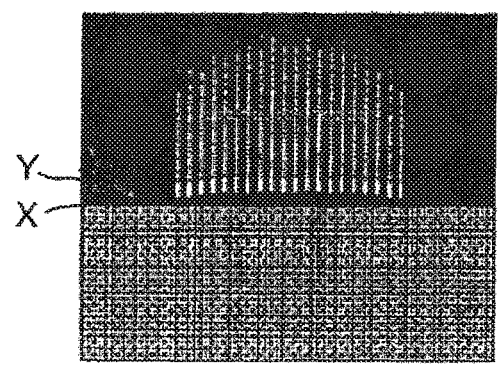
FIG. 51B is a lateral view showing the dome-shaped coil used in the analysis.

Referring to FIGS. 51A and 51B, the part appears below the coil model was the brain model 90.

The magnetic body 22 in which the magnetic plates were laminated in the X direction was employed so that the dome-shaped coil did not disturb the distribution of the induced electric field generated in the brain model. It was conceived that this model could increase the stimulation efficiency without excessively changing the stimulation robustness.

(d) Analysis Results

Figure 52A:
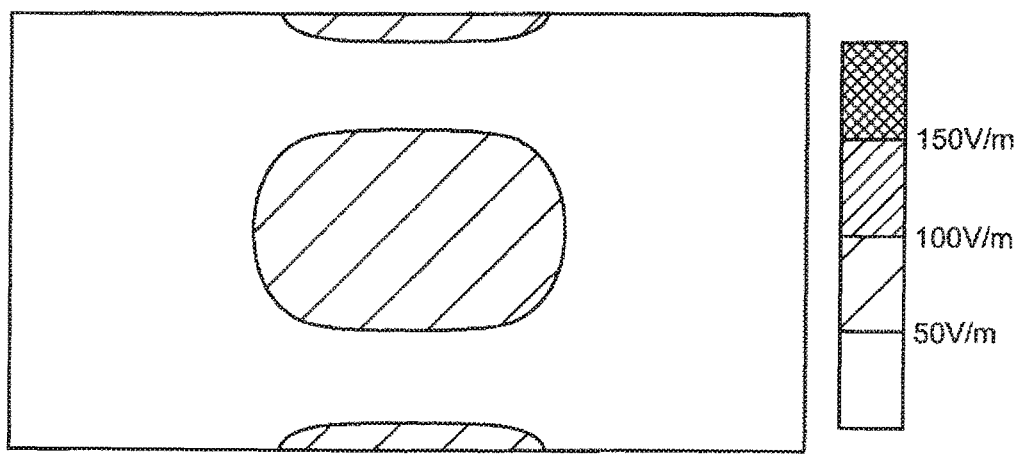
FIG. 52A is a contour graph showing analysis results of brain-surface-induced electric fields.
Figure 52B:
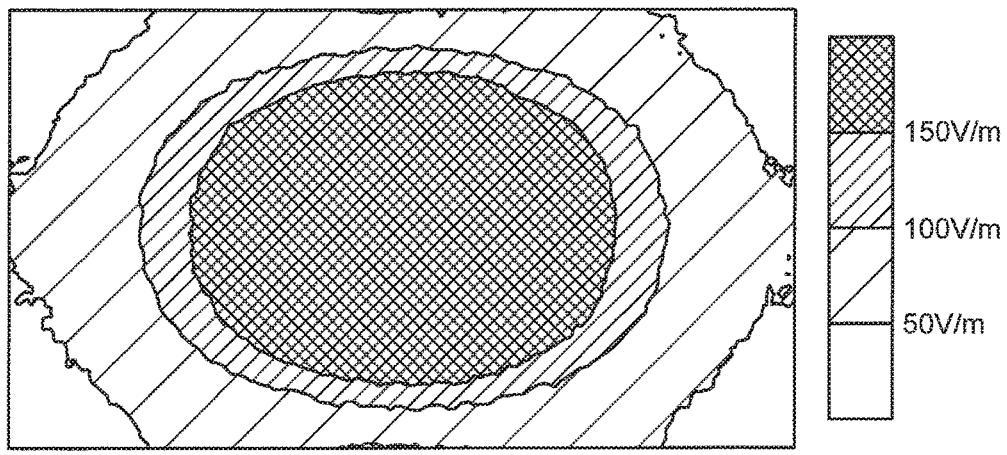
FIG. 52B is a contour graph showing analysis results of brain-surface-induced electric fields.
Figure 52C:
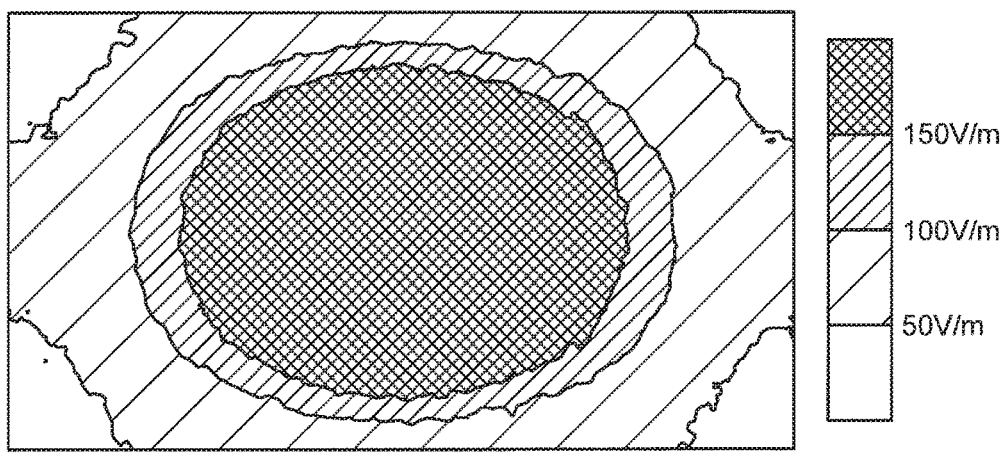
FIG. 52C is a contour graph showing analysis results of brain-surface-induced electric fields.

FIGS. 52A to 52C show analysis results of brain-surface-induced electric fields for the coil models 1 to 3, respectively. According to the analysis results, the average induced electric field intensity of the coil model 1 (no magnetic body, FIG. 52A) was 71.8 V/m, the average induced electric field intensity of the coil model 2 (the thickness of the magnetic body was 4 mm, FIG. 52B) was 453 V/m, and the average induced electric field intensity of the coil model 3 (the thickness of the magnetic body was 12 mm, FIG. 52C) was 501 V/m. As shown by the results, it could be understood that providing the X-axis-direction magnetic body collected the magnetic fields generated by the dome-shaped coil, on the magnetic body, and then, significantly improved the stimulation efficiency of the brain. In addition, when the thickness of the magnetic body 22 increased, the distance between the bottom surface and the top surface of the magnetic body 22 increased, and, as a result, the act of weakening the brain-surface-induced electric field by the induced current on the top surface became small. Conceivably for this reason, the brain-surface-induced electric field further increased in the coil model 3 in which the thickness of the magnetic body 22 was 12 mm.

Figure 53A:
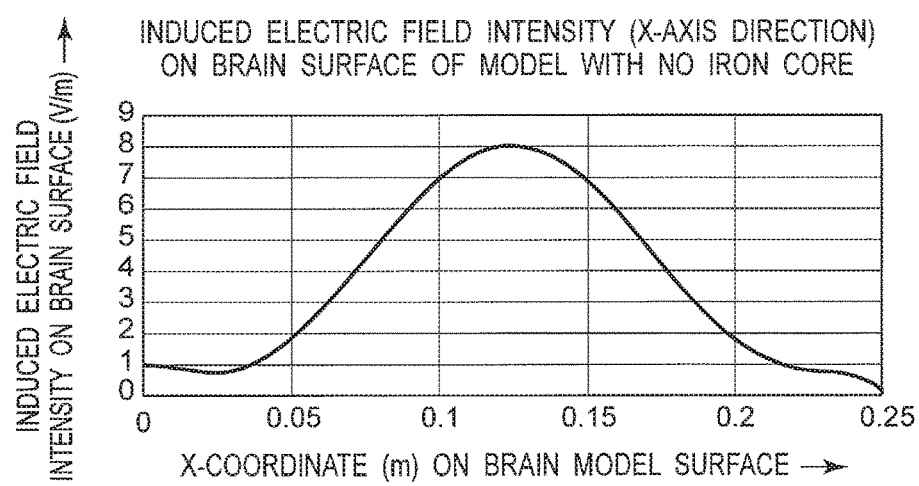
FIG. 53A is a graph showing robustness of a coil model without a magnetic body and is a graph showing induced electric field intensities on the brain surface with respect to X coordinates of the brain model surface.
Figure 53B:
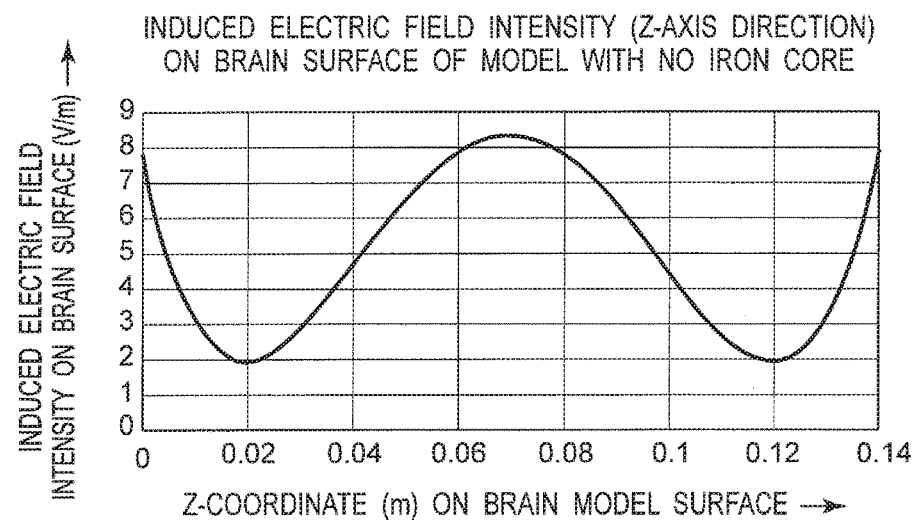
FIG. 53B is a graph showing robustness of a coil model without a magnetic body and is a graph showing induced electric field intensities on the brain surface with respect to Z-coordinates of the brain model surface.

FIG. 53A and FIG. 53B show the robustness in the X-axis direction and the Z-axis direction in the coil model 1 with no magnetic body 22. The X-axis-direction and Y-axis-direction effective simulation distances of the coil model 1 with no magnetic body 22 were 0.0821 m and 0.0450 m, respectively. The X-axis-direction and Y-axis-direction effective simulation distances, of the coil model 2 having the magnetic body 22 having a thickness of 4 mm, were 0.0755 m and 0.0555 m, respectively. The X-axis-direction and Y-axis-direction effective simulation distances, of the coil model 3 having the magnetic body 22 having a thickness of 12 mm, were 0.0745 m and 0.0560 m, respectively.

According to these results, it could be understood that providing the X-axis-direction laminated magnetic body 22 decreased the X-axis-direction effective stimulation distance. In addition, it was confirmed that disposing the magnetic body 22 caused the shape of the stimulation range to be closer to a circular shape. The inductance of the coil model 2 having the magnetic body 22 having a thickness of 4 mm was 85.9 µH. It was conceived that the inductance increased for the reasons that the winding density and cross-sectional area of the coil 8 were larger and that the magnetic body was disposed in the internal portion of the coil 8 as compared with the eccentric figure-eight-shaped coil.

(d) Comparison of Stimulation Robustness

Figure 54:
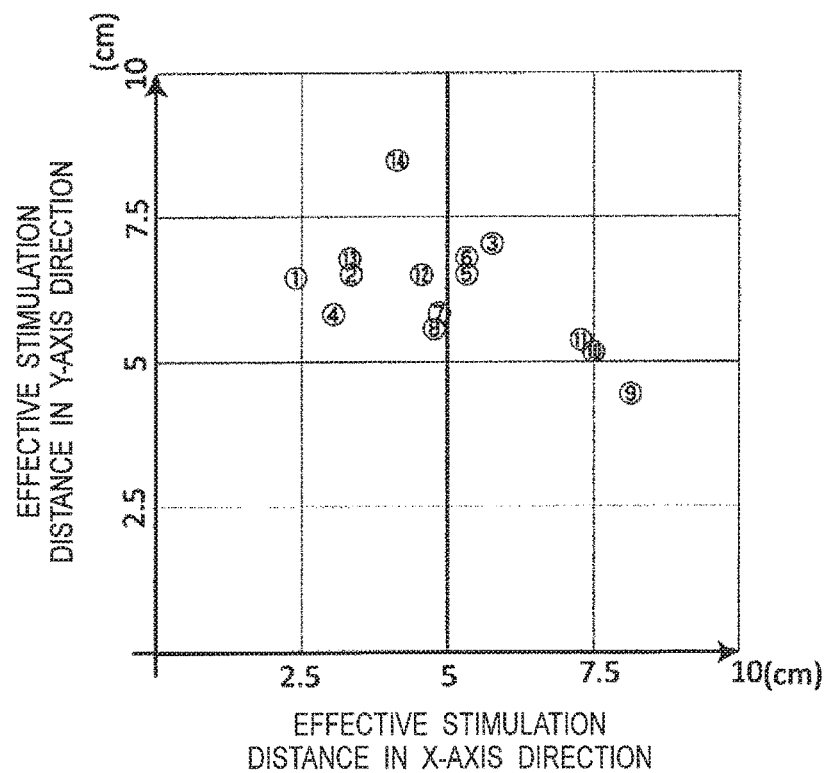
FIG. 54 is a graph showing stimulation robustness of a plurality of coil models and is a graph showing the models on the graph of Y-axis-direction effective stimulation distances with respect to X-axis direction effective stimulation distances.

FIG. 54 summarizes the stimulation robustness (effective stimulation distance) evaluated about the above described plurality of analysis models. The coil models with the numbers of FIG. 54 (hereinafter, referred to as CM1 to CM14) are described below.

CM1: a coil model having an X-laminated cuboidal magnetic body (220×122×10 mm);

CM2: a coil model having a Y-laminated cuboidal magnetic body (220×122×10 mm);

CM3: a coil model having an XY-laminated cuboidal magnetic body (220×122×10 mm);

CM4: a no-magnetic-body coil model;

CM5: a coil model having XY-laminated cuboidal magnetic body (220×100×10 mm);

CM6: a coil model having an XY-laminated cuboidal magnetic body (220×140×10 mm);

CM7: a coil model having a Y-laminated cuboidal magnetic body (220×122×2 mm);

CM8: a coil model having a Y-laminated cuboidal magnetic body (220×122×5 mm);

CM9: no-magnetic-body dome-shaped coil model;

CM10: a dome-shaped coil model having an X-laminated cuboidal magnetic body (thickness: 4 mm);

CM11: a dome-shaped coil model having an X-laminated cuboidal magnetic body (thickness: 12 mm);

CM12: a coil model in which ferrite (bending is 15 mm) is inserted at the position having a distance of 10 mm from a magnetic body;

CM13: a coil model having an X-laminated tetragonal-skeleton-shaped magnetic body; and CM14: a coil model having a Y-laminated tetragonal-skeleton-shaped magnetic body.

The following could be understood from FIG. 54. The only model having the shorter X-axis-direction effective stimulation distance than that of the no-magnetic-body model CM4 was the coil model CM1 having the X-laminated cuboidal magnetic body (220×122×10 mm). This was for such a reason that the induced current in the X direction laminated magnetic body acted to reduce the brain-surface-induced electric field generated by the coil.

Even when the eccentric figure-eight-shaped coil was provided with the magnetic body 22, the Y-axis-direction effective stimulation distance did not largely change. This was conceivably for such a reason that, since the Y-axis-direction component of the induced electric field generated in the brain-surface central part by the eccentric figure-eight-shaped coil was sufficiently strong, the large values thereof are still maintained even under influence of the induced electric field generated by the magnetic body 22.

The coil models CM3, CM5, and CM6 of the XY-laminated magnetic bodies had the stimulation directions different from that of the dome-shaped coil having high robustness, but these coil models had equivalent stimulation ranges. This was for such a reason that the induced current at the part of the X direction laminated magnetic body in the XY-laminated magnetic body acted in the direction to enhance the induced electric fields generated in both-end regions of the brain model by the eccentric figure-eight-shaped coil, but the induced current of the part of the Y direction laminated magnetic body generated an electric field in the direction orthogonal to the induced electric field generated at the center of the brain model by the eccentric figure-eight-shaped coil. In other words, this was for such a reason that the induced currents in the magnetic body acted to stretch the induced electric fields in the brain, which were generated by the figure-eight-shaped coil, in the X-axis direction.

Figure 55A:
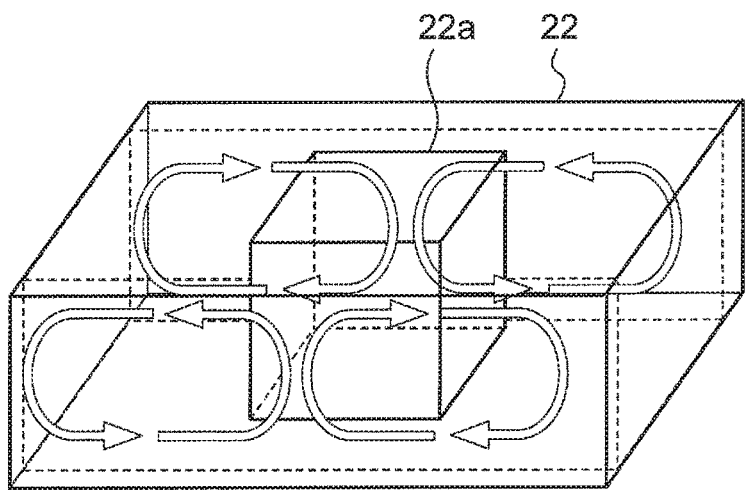
FIG. 55A is a perspective view showing currents in a Y direction laminated tetragonal-skeleton-shaped magnetic body and showing induced electric fields generated by them at a brain surface.
Figure 55B:
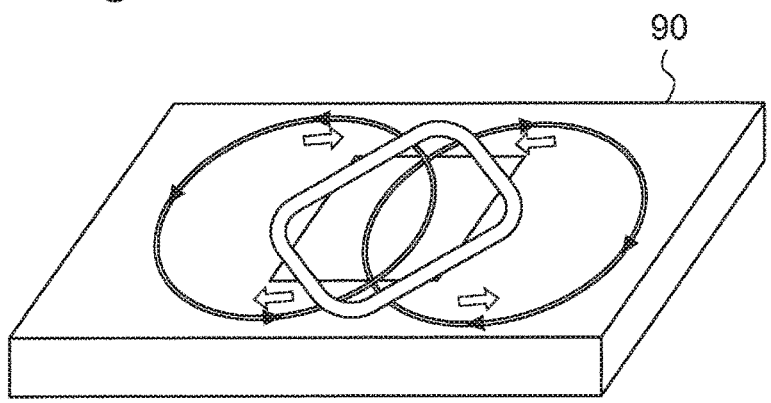
FIG. 55B is a perspective view showing currents in a Y direction laminated tetragonal-skeleton-shaped magnetic body and showing induced electric fields generated by them on the brain surface.

In the coil model CM14 having the tetragonal-skeleton-shaped Y-laminated magnetic body, the induced electric field generated on the brain surface by the coil could be cancelled out by adjusting the laminating direction. In addition, in the coil models CM13 and CM14 from which the magnetic-body part in the central part was removed, the induced electric field generated in the part immediately below this central part was not affected, and it was conceived that the effective stimulation distances in the X-axis direction and the Y-axis direction extended as shown in FIGS. 55A and 55B for this reason.

2.2.7 Designing of Magnetic Body which Suppresses Magnetic Field Leakage and Analysis of Magnetic Field Leakage (a) Magnetic Field Leakage A home system using radiation had to satisfy safety standards of electromagnetic-wave levels (See Table 3), which were determined by the International Commission on Non-Ionizing Radiation Protection (ICNIRP) and supposed to be safe even if humans were exposed thereto. In a transcranial magnetic stimulation apparatus, since the stimulation condition expected therein was about 3 kHz, the permissible magnetic-field level was 21 A/m.

TABLE 3

| Frequency Range | Electric field Intensity E (kV/m) | Magnetic-Field Intensity H (A/m) | Magnetic-Field Density B (T) |
| --- | --- | --- | --- |
| 1 Hz to 8 Hz | 5 | $3.2 \times 10^4/f^2$ | $4 \times 10^{-2}/f^2$ |
| 8 Hz to 25 Hz | 5 | $4 \times 10^3/f$ | $5 \times 10^{-3}/f$ |
| 25 Hz to 50 Hz | 5 | $1.6 \times 10^2$ | $2 \times 10^{-4}$ |
| 50 Hz to 400 Hz | $2.5 \times 10^2/f$ | $1.6 \times 10^2$ | $2 \times 10^{-4}$ |
| 400 Hz to 3 kHz | $2.5 \times 10^2/f$ | $6.4 \times 10^4/f$ | $8 \times 10^{-2}/f$ |
| 3 kHz to 10 MHz | $8.3 \times 10^{-2}$ | 21 | $2.7 \times 10^{-5}$ |

When a non-healthcare worker other than a patient operated the system, it was conceived that the non-healthcare worker got closer to 60 to 100 cm from the stimulation coil 8. Therefore, in order to ensure safety for the non-healthcare worker, it was desired that the magnetic-field levels at the locations distant from the stimulation coil 8 by 60 to 100 cm were set to equal to or smaller than the safety values.

Figure 56:
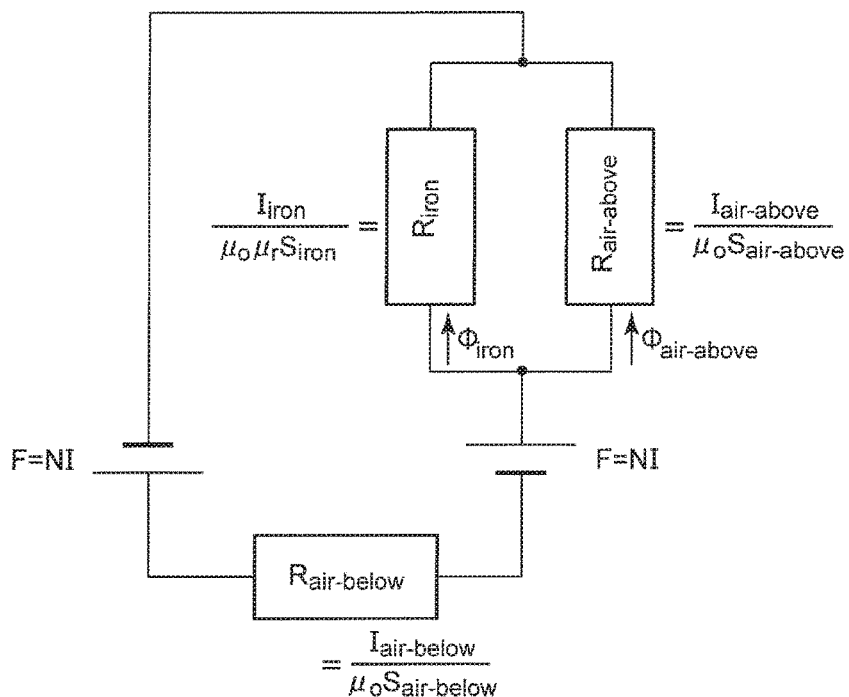
FIG. 56 is a circuit diagram showing an equivalent magnetic circuit of a coil model having a Y direction laminated cuboidal magnetic body.

On the other hand, in the coil model having the Y direction laminated cuboidal magnetic body, it was conceived that not all the magnetic fields generated by the coil 8 passed through the interior of the laminated magnetic body 22, and part thereof leaked to the space outside the magnetic body 22. Therefore, about a coil model having the Y direction laminated cuboidal magnetic body 22, the magnetic flux which leaked to outside the magnetic body 22 was analyzed. FIG. 56 shows an equivalent magnetic model used in the analysis. Equation (12) shows a magnetic circuit equation of the equivalent circuit of FIG. 56.

$$NI+NI=(\Phi_{iron}+\Phi_{air\text{-}above})R_{air\text{-}below}+\Phi_{iron}R_{iron} \tag{12}$$

In Equation (12), $(\Phi_{iron}+\Phi_{air\text{-}above})$ is equivalent to the value obtained by multiplying the density of the magnetic flux generating by the coil 8 with a magnetic permeability of air. The magnetic field generated by the coil 8 is approximated by Equation (11), and the parameter values of the following equations are substituted to Equation (11).

N=10.1,
I=3.03,
$\mu_0 = 4\pi \times 10^{-7}$,
$l_{air\text{-}below}=0.04\pi$,
$l_{iron}=0.22$,
$\mu_r=5000$, and
$S_{iron}=0.122 \times 0.01$.

In this case, the magnetic flux passing through the magnetic body 22 is calculated in the manner of Equation (13).

$$\Phi_{iron}=0.328 \tag{13}$$

Since it can be assumed that the magnetic flux flowing in the magnetic circuit does not decrease, Equation (14) is obtained.

$$\mu_0 N S_{air\text{-}below}=\Phi_{iron}+B_{air\text{-}above}S_{air\text{-}above} \tag{14}$$

Since it can be assumed thon the surface area of the magnetic circuit does not decrease as well, Equation (15) is obtained.

$$S_{air\text{-}below}=S_{air\text{-}above}++S_{iron} \tag{15}$$

When the simultaneous equations of Equations (14) and (15) are solved, the magnitude of the magnetic flux, which does not enter the magnetic body, but leaks to the air region is given by Equation (16).

$$|\Phi_{air\text{-}above}|=0.323 \tag{16}$$

In this manner, the magnetic flux which leaks from the magnetic body 22 is large. Therefore, it is expected that a strong leak magnetic field generates around the coil 8. The magnetic flux which leaks in the Z-axis direction is conceivably the strongest. However, leak magnetic flux in the X-axis direction and the Y-axis direction is also expected. Therefore, reduction of the leak magnetic field will be considered on the assumption of a magnetic shield having a shape which covers the magnetic body 22 and the coil 8.

A medium of the magnetic shield will be studied. When a coil current is 3 kA, a current I flowing on the surface of the magnetic body 22 is conceivably about 1 kA at most. Therefore, the intensity of the magnetic field generated at a location distant from the coil central part by about 1 m in the Z-axis direction by the induced current in the magnetic body 22 is obtained in the manner of Equation (17) based on the equation of Biot-Savart.

$$|H| = \frac{1.0 \times 10^3 \times 0.122 \times 1}{4\pi 1^3} = 9.7 (A/m) \tag{17}$$

It is conceived that the current actually flowing in the magnetic shield is somewhat small. However, when the fact that the safety standard of the magnetic field is 21 A/m is taken into consideration, the magnetic-field intensity generated by the induced current in the magnetic body 22 has an unignorable magnitude. The magnetic shield is preferably made of a material such as ferrite, which not only prevents the leak magnetic field, but also does not allow induced currents to flow therein as much as possible.

(b) Analysis Models and Evaluation Standards

Figure 35:
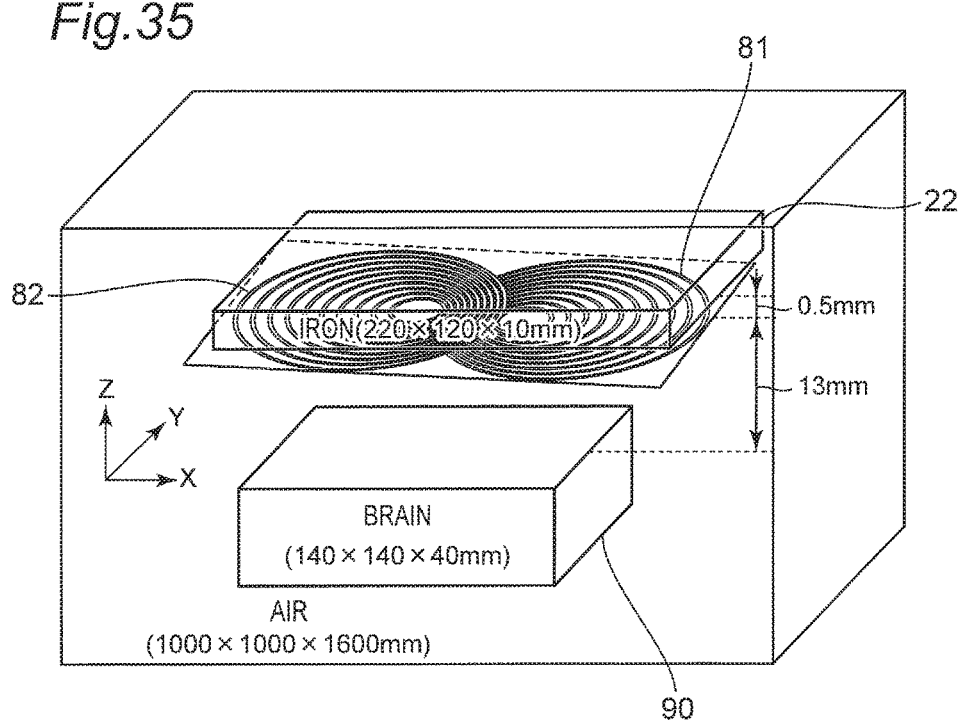
FIG. 35 is a perspective view showing a basic analysis model.
Figure 57:
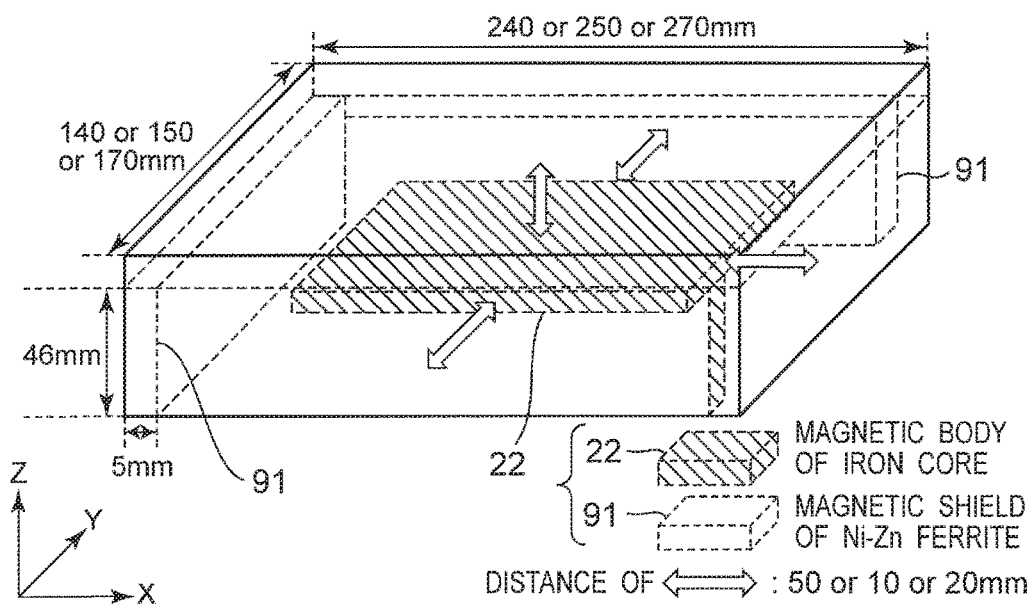
FIG. 57 is a perspective view showing outlines of an analysis model.

An analysis model of FIG. 57 was similar to the analysis model shown in FIG. 35, but is different in the points of the size of the air region and the presence of the magnetic shield. The size of the air region was set to 2 m×2 m×2 m in order to study the influence of the leak magnetic field across a large range. Referring to FIG. 57, the magnetic body 22 was a cuboidal magnetic body of 220 mm×120 mm×10 mm in which magnetic plates were laminated in the Y-axis direction. The electric conductivity of the magnetic body 22 was $10^7$ S/m, and the relative magnetic permeability was 1,500. A magnetic shield 91 surrounding the upper side and four lateral sides of the magnetic body 22 was made of Ni—Zn ferrite, the electric conductivity thereof was $10^{-5}$ S/m, and the relative magnetic permeability thereof was 1,500. The Z direction interval between the magnetic body 22 and the magnetic shield 91 was set to 20 mm, and the distance between the bottom surface of the magnetic body 22 and a ceiling surface (inner surface) of the magnetic shield 91 was set to 46 mm. Three models having intervals in the different X and Y directions between the magnetic body 22 and the magnetic shield 91 were created which include the models with an interval of 5 mm (model 1), an interval of 10 mm (model 2), and an interval of 20 mm (model 3), and a model without the magnetic shield (model 4), and then, the leak-magnetic-field intensity of each of them was calculated.

The safety standard 21 A/m of the leak magnetic field was a comparatively small value. Therefore, it was conceivably important to consider the influence of comparatively small induced currents generated in the ferromagnetic body. Therefore, it was preferred to surround the laminated magnetic body 22 with a substance having a low electric conductivity such as ferrite so as not to leak the magnetic field generated by the magnetic body 22 to the outside in addition to the magnetic field generated by the coil 8. In terms of downsizing of the coil apparatus, the distance between the ferrite and the laminated magnetic body 22 was preferred to be short as much as possible. However, when both of them were too close to each other, not the laminated magnetic body 22, but the ferrite became a small magnetic passage of magnetic resistance and reduced the efficiency of stimulation to the brain.

The distance from the coil center to the position at which the magnetic-field intensity became 21 A/m was measured in five directions including the X+ direction, X direction, Y+ and Y direction, and Z+ direction, and the distances thereof were compared with each other. The size of the air element in the analysis model was large. Therefore, exponential function approximation was carried out for a graph including the magnetic-field intensity of each air element as a vertical axis and including the distance from the top-surface central part of the magnetic body 22 as a horizontal graph, and then, magnetic-field intensities were measured. As an approximation method, exponential approximation was carried out by using non-linear regression analysis by using statistical analysis free software "R" so as to get close to a form of $y=Cx^{-2}$. This was for such a reason that attenuation of electromagnetic waves was inversely proportional to the square of the distance.

(c) Analysis Results

Table 4 shows leak-magnetic-field intensities calculated for the models 1 to 4. In the analysis in which the magnetic-field intensity did not converge to 21 A/m (in the table, the analysis in which numerical values were surrounded by ( )), the magnetic-field intensity at the position which was positioned at an end of the air region and was 1 m from the central part of the coil 8 was described.

TABLE 4

| Distance (m) at which Leak Magnetic-Field Intensity was 21 A/m (Magnetic-Field Intensity (A/m)) | Model without Ferrite | Model in which Ferrite was placed at a distance of 5 mm from Iron Core | Model in which Ferrite was placed at a distance of 10 mm from Iron Core | Model in which Ferrite was placed at a distance of 20 mm from Iron Core |
| --- | --- | --- | --- | --- |
| Positive X direction | (119) | (75.0) | (59.9) | (56.6) |
| Negative X direction | (117) | (58.3) | (49.4) | (47.8) |
| Positive Y direction | (66) | (26.5) | (23.4) | 0.84 |
| Negative Y direction | (60) | (24.4) | (23.4) | 0.90 |
| Positive Z direction | 0.674 | 0.324 | 0.358 | 0.428 |

As was apparent from Table 4, the Z+ direction leak magnetic fields of the models having the magnetic shields (models 1 to 3) decreased than that of the model without the magnetic shield 91 (model 4). In addition, the shorter the distance between the magnetic shield 91 and the magnetic body 22, the more the leak magnetic fields decreased.

Regarding the X-axis direction and the Y-axis direction, it was confirmed that providing the magnetic shield 91 decreased the leak magnetic fields; however, it was found out that the shorter the distance between the magnetic body 22 and the magnetic shield 91, the larger the leak magnetic fields. This was conceivably for such a reason that, as the distance between the magnetic body 22 and the magnetic shield 91 increased, the curvature radius of the magnetic force line became wider. For example, when the distance between the magnetic shield 91 and the magnetic body 22 was 5 mm, the incident angle of the magnetic force line with respect to the magnetic shield 91 became small. As a result, the magnetic force line was more easily absorbed by the magnetic shield 91, and the leak magnetic field in the Z-axis direction conceivably became small.

Figure 58:
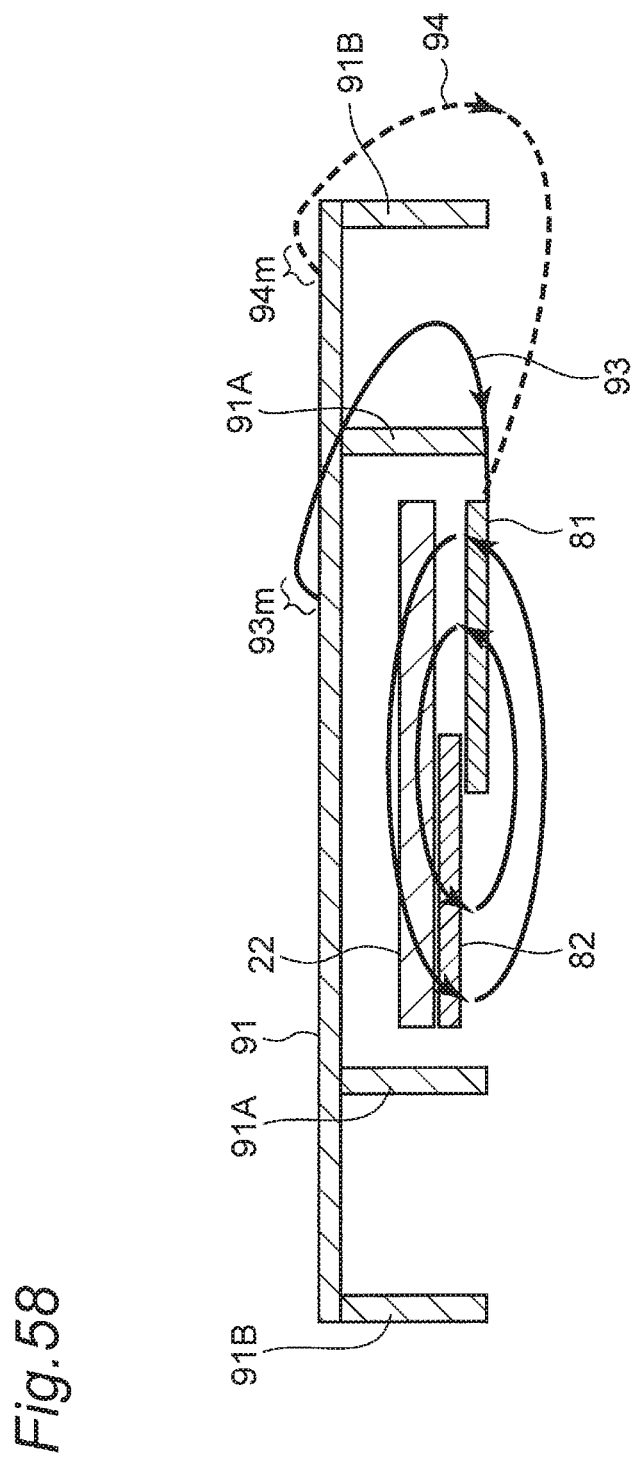
FIG. 58 is a cross-sectional view showing a distribution of magnetic force lines in an XZ cross section passing through the central part of the magnetic body.

Actually, as shown in FIG. 58 showing a magnetic-field distribution of an XZ cross section passing through the center of the magnetic body 22, the incident angle of the magnetic force line with respect to the magnetic shield 91 when the horizontal-direction distance between the magnetic shield 91 and the magnetic body 22 was 5 mm (magnetic shield 91A) was larger than the incident angle of the case in which the horizontal-direction distance between the magnetic shield 91 and the magnetic body 22 was 20 mm (magnetic shield 91B). Therefore, the magnetic force line thereof reaches further in the Z+ direction. It was noted that either one of the magnetic shields 91A and 91B was selected. In FIG. 58, a solid line 93 was a magnetic force line when the distance between the magnetic body and the ferrite was 5 mm, and a dotted line 94 was a magnetic force line when the distance between the magnetic body and the ferrite was 20 mm.

In addition, regarding the X-axis direction and the Y-axis direction, the magnetic-field intensities along the top surface of the magnetic shield 91 in the X-axis direction were evaluated. When the distance between the ferrite magnetic shield 91 and the magnetic body 22 was 5 mm, a peak of the magnetic-field intensities was shown at a part close to a part 93 *m*. In the case of 20 mm, a peak of the magnetic-field intensities was shown at a part slightly distant from a part 94 *m* in the Z-axis negative direction. In the model with a distance of 20 mm between the magnetic body and the ferrite, the magnetic-field intensity decreased.

The inductance of the model 4 without the magnetic shield 91 was 16.7 μH. The inductances of the models 1 to 3 with a distance of 5 mm between the magnetic shield 91 and the magnetic body 22 were 17.0 μH, 16.8 μH, and 16.7 μH, respectively. It was conceived that the inductance increased since the shorter the distance between the magnetic shield 91 and the magnetic body 22, the more magnetic flux from the coil 8 passed through the magnetic shield 91.

The average values of the induced electric field intensities in the brain-surface central parts of the models 1 to 4 were 287 V/m, 307 V/m, 304 V/m, and 300 V/m, respectively. According to these results, it was conceived that, when the distance between the magnetic body 22 and the magnetic shield 91 became 10 mm or smaller, the magnetic resistance of the magnetic shield 91 became smaller than the magnetic resistance of the magnetic body 22, and, as a result, the brain-surface-induced electric field became weak. Therefore, setting the distance between the magnetic body 22 and the magnetic shield 91 to about 10 mm was conceivably appropriate.

2.2.8 Optimization of Magnetic Shield Minimally Suppressing Leak Magnetic Field

As was understood from Table 4, there was no model that satisfied the safety standard 21 A/m determined by the International Commission on Non-Ionizing Radiation Protection (ICNIRP) in all the directions. Therefore, the model with a distance of 10 mm between the magnetic body 22 and the magnetic shield 91 was improved to create an analysis model in which the bottom end opening of the box-shaped magnetic shield 91 opposing the coil was created with a ring-shaped flange (bending) 91F projecting from the bottom end toward the inner side in the horizontal direction as shown in FIG. 59.

(a) Analysis Model

Figure 59:
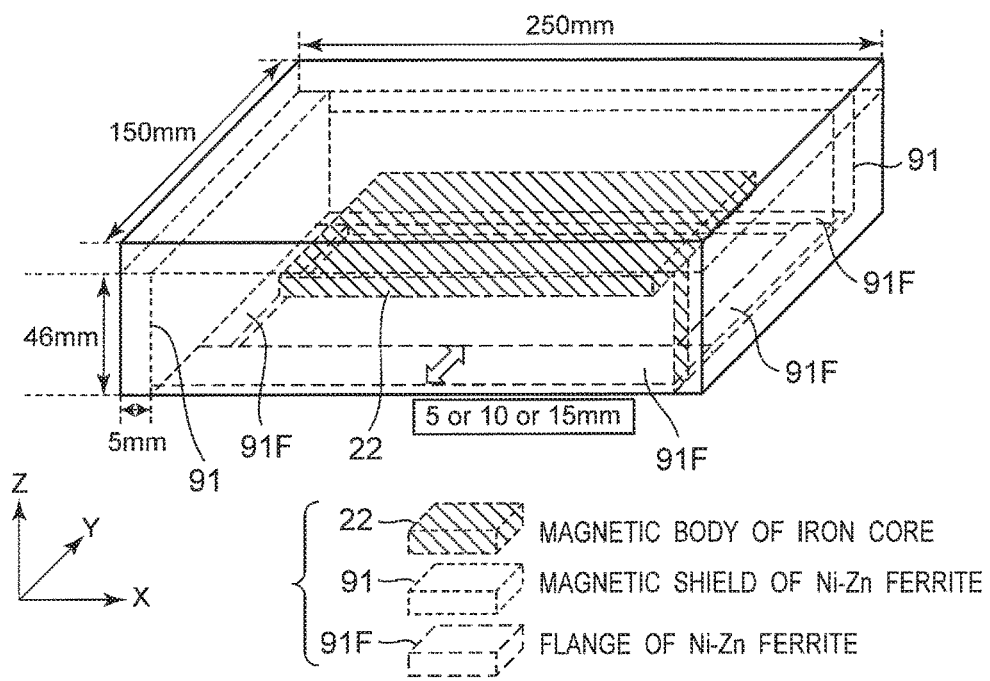
FIG. 59 is a perspective view showing an improved analysis model.

Referring to FIG. 59, three analysis models (models M1 to M3) respectively having widths of the flanges 91F of 5 mm, 10 mm, and 15 mm were created. The material of the flange 91F was Ni—Zn ferrite.

(b) Analysis Results

Table 5 shows leaked magnetic fields analyzed for the analysis models of FIG. 59. In the analysis in which the magnetic-field intensity did not converge to 21 A/m (in the table the analysis in which numerical values were surrounded by ( )), the magnetic-field intensity at the position which was 1 m in the horizontal direction from the coil center serving as an end of the air region was described.

TABLE 5

| Distance (m) at which Leak Magnetic-Field Intensity was 21 A/m (Magnetic-Field Intensity (A/m)) | Model without Ferrite | Model in which Ferrite Bending was 5 mm | Model in which Ferrite Bending was 10 mm | Model in which Ferrite Bending was 15 mm |
|---|---|---|---|---|
| Positive X direction | (59.9) | (58.9) | (58.9) | (51.4) |
| Negative X direction | (49.4) | (51) | (48.5) | (42.1) |
| Positive Y direction | (22.4) | (26.8) | (22.6) | (21.8) |
| Negative Y direction | (22.4) | (25.8) | 0.91 | 0.965 |
| Positive Z direction | 0.358 | 0.34 | 0.334 | 0.329 |

Figure 60:
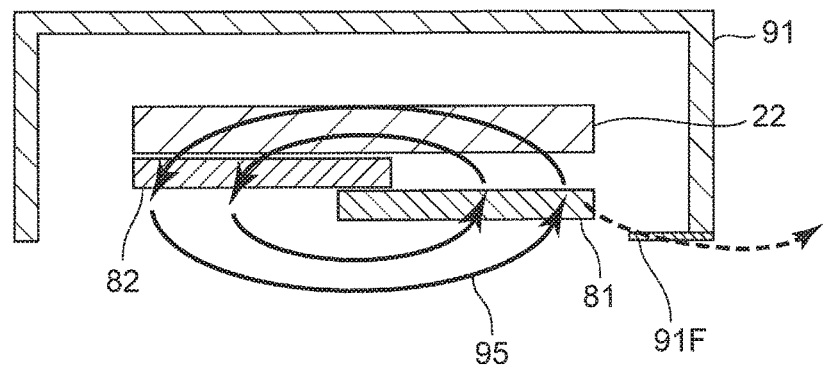
FIG. 60 is a cross-sectional view showing a situation in which leakage of magnetic flux is blocked by a flange.

In this case, the bending of ferrite was the above described flange 91F. The average values of the brain-surface-induced electric fields at the target points of the models M1 to M3 were 309, 309, and 309 V/m, respectively. Therefore, 15 mm was the optimum as the length of the flange 91F. The reason why the longest flange 91F was effective was that, the flange 91F traps a part of the magnetic flux which tries to leak from the bottom opening of the magnetic shield 91 as shown in FIG. 60.

As the results of the analysis, the leak magnetic fields of the model with a distance of 10 mm between the magnetic body 22 and the magnetic shield 91 and with the flange 91F having a length of 15 mm were improved by 56.8% in the X+ direction, by 51.2% in the X direction, by 67.0% in the Y+ direction, by 70.0% in the Y direction, and by 51.2% in the Z direction as compared with those of the model with no magnetic shield 91 and no flange 91F.

When it was assumed that a healthcare worker was in the rear of the coil 8 (at a location distant in the Y direction from the coil), the leak magnetic fields in the X direction were not problematic. In addition, when such a state that the healthcare worker holds the stimulation coil by his/her hands was expected, the distance margins could be made in the Y direction and the Z direction by the distance of the length of his/her arm.

The coil inductance of the model having the flange 91F of 5 mm was 16.9 µH, the coil inductance of the model having the flange 91F of 10 mm was 17.1 µH, and the coil inductance of the model having the flange 91F of 15 mm was 17.4 µH. It was conceived that the longer the length of the flange 91F, the more the magnetic flux passed through the magnetic shield 91, and the inductance increased.

The X-axis-direction effective stimulation distance and the Y-axis-direction effective stimulation distance of the model with no magnetic shield 91 were 0.0455 m and 0.0604 m, respectively. The X-axis-direction effective stimulation distance and the Y-axis-direction effective stimulation distance of the model having the magnetic shield 91 equipped with the flange 91F (the distance between the magnetic body 22 and the magnetic shield 91 in the horizontal direction was 10 mm, and the length of the flange 91F was 5 mm) were 0.0459 m and 0.0605 m, respectively. The X-axis-direction effective stimulation distance and the Y-axis-direction effective stimulation distance of the model having the magnetic shield equipped with the flange 91F (the distance between the magnetic body 22 and the magnetic shield 91 was 10 mm, and the length of the flange 91F was 10 mm) were 0.0461 m and 0.0608 m, respectively. The X-axis-direction effective stimulation distance and the Y-axis-direction effective stimulation distance of the model having the magnetic shield 91 equipped with the flange 91F (the distance between the magnetic body 22 and the magnetic shield 91 in the horizontal direction was 10 mm, and the length of the flange 91F was 15 mm) were 0.0464 m and 0.0629 m, respectively.

3 CONSIDERATIONS

3.1 Reasons why Magnetic Body was Disposed Above Figure-Eight-Shaped Coil

In order to induce magnetic flux, for example, in a solenoid, a magnetic body was disposed inside the coil 8. However, since each of the circular coil parts 81 and 82 of the eccentric figure-eight-shaped coil for use in the transcranial magnetic stimulation apparatus was made by a conductive wire, for example, wound in a helical shape (spirally) about ten times, effectively disposing the magnetic body 22 such as an iron core in the small space formed in the center of the circular coil part 81 or 82 was difficult and took cost. Therefore, this was not suitable for the home coil 8. Instead of this, a method of embedding a magnetic body in the head of a patient to concentrate the magnetic flux therein was also proposed. However, this method requires a craniotomy, and the characteristics of the transcranial magnetic stimulation treatment having such an advantageous effect in non-invasiveness could not be utilized. On the other hand, the configuration in which the magnetic body 22 was disposed above the coil 8 solves all the above described problems, and has such an advantageous effect that the magnetic flux generated by the coil could be concentrated by a degree necessary for treatment.

3.2 Reasons why Ni—Zn Ferrite Core was Used in Magnetic Shield

The magnetic body 22 disposed in the coil could also function as the magnetic shield 91. For example, when a frequency was about 3 kHz, the induced current in the magnetic body 22 was practically cancelled out, and was slightly present on the surface of the magnetic body 22. However, in a transcranial magnetic stimulation apparatus, even if the current was minute, the electromagnetic waves generated by that may decrease treatment effects. Therefore, it was hard to say that the magnetic body was sufficiently effective as the magnetic shield 91.

On the other hand, Ni—Zn ferrite has a relative magnetic permeability of 1,500 and an electric conductivity of about 0.00001 S/m, and can be practically considered as an insulator. In addition, the Ni—Zn ferrite has a relative temperature coefficient of about 1 to 3, and the magnetic permeability is not easily affected by temperatures. Further, the magnetic permeability of ferrite has a constant value up to a certain frequency. However, when the frequency exceeds this frequency, the magnetic flux density thereof cannot follow the changes in magnetic fields, and a phase lag of the magnetic flux density with respect to the magnetic field may occur. However, Ni—Zn ferrite (HF70) has certain magnetic-permeability/frequency characteristics, and does not adversely affect the transcranial magnetic stimulation treatment having a stimulation frequency of about 3 kHz. Therefore, it was conceived that Ni—Zn ferrite was appropriate for the material used in the magnetic shield 91.

3.3 Stimulation Coil Fixing Method in Home Treatment

When a situation in which a patient of neuropathic pains operates the home-treatment transcranial magnetic stimulation apparatus by himself/herself to carry out treatment is expected, it is preferred that the patient himself/herself could position the stimulation coil 8 to the same location every time. Therefore, the techniques of causing the patient to wear a helmet and fixing the stimulation coil 8 to the helmet are proposed. In such an embodiment, it is desired that the stimulation coil 8 can be easily attached to the helmet.

3.4 Weight of Stimulation Coil

The total weight of the magnetic body 22 and the magnetic shield 91, having the optimum shapes obtained from the above described analysis, was about 2.1 kg. The weight of the eccentric figure-eight-shaped coil itself was about 1 kg. Therefore, the entire coil apparatus including the magnetic body 22 and the magnetic shield 91 had a weight of about 3 kg, which could be stably supported even in a home system.

3.5 Inductance of Stimulation Coil Apparatus

The inductance of a magnetic-body ferrite model, which was conceivably the most appropriate, was about 17.4 µH. The analysis was carried out only in the air region, and the inductance of the coil was calculated based on Equation (18) by using the sum of the magnetic-field energy in the air region.

$$\frac{1}{2}LI^2 = \frac{1}{2\mu}\int B^2 dV \qquad (18)$$

A pulse width (T) conceivably effective for obtaining the effects of magnetic stimulation treatment was about 200 to 300 µs. Therefore, when the capacity of the coil was C=180 µF, the inductance of the coil 8 was 5.63 µH to 12.6 µH according to Equation (19).

$$T = 2\pi\sqrt{LC} \qquad (19)$$

3.6 Induced Currents in Iron Core

The induced current flowing in the magnetic body 22 was determined by the change rate of the magnetic flux based on the Faraday's law. In this case, the induced current was conceivably affected by the speed of magnetizing the magnetic body by the magnetic field and the speed by which the magnetic field generated by the coil changes. Since the former one was sufficiently higher than the latter one, the induced current actually flowing in the magnetic body was conceivably approximately equal to the induced current obtained by analysis.

3.7 about Magnetic Saturation of Iron

Iron has magnetic characteristics of hysteresis. On the other hand, the magnetic flux passing through the magnetic body 22 was calculated as 0.328 τ (See Equation (13)). However, when the hysteresis was taken into consideration, in a high magnetic field, the relative magnetic permeability became low. In consideration of this point, the induced electric field density of the magnetic body was conceivably about 10 to 50τ. Since the saturation magnetic-flux density of iron was 2.15τ, improvement such as increasing the magnetic flux by increasing the thickness of iron may be required in order to obtain desired characteristics with iron.

3.8 Insulator for Use in Laminated Magnetic Body

The laminated magnetic body 22 was formed by sandwiching insulators between a plurality of magnetic plates. In this case, Mn—Zn-based ferrite was conceivably suitably used as the insulator. Mn—Zn-based ferrite has a relative magnetic permeability of 5,000 which was the same as iron, a volume resistivity of 0.3 Ωm, and an adaptive frequency of up to 1 MHz.

3.9 Downsizing of Stimulation Apparatus by Improving Stimulation Efficiency (Cost Reduction)

A magnetic-body coil model capable of obtaining stimulation efficiency 3.93 times that of a no-magnetic-body coil model was created. The induced current intensity for the primary motor cortex required to obtain effective treatment effects was to be constant. However, the magnitude of the induced current in the brain was proportional to the coil current. In the above described analysis, the coil current was set to 3 kA. In this case, the electric field induced into the brain by the coil model including the XY-laminated magnetic body was 507 V/m. The past clinical test results have reported that the induced current density required for the primary motor cortex to obtain effective treatment effects was 180 A/m². When the electric conductivity of the stimulation part was assumed to be 0.11 S/m, which was the same as that of the gray matter, the induced electric field intensity in the brain necessary for obtaining effective treatment effects was 200 V/m. Therefore, in the case of a laminated-magnetic-body coil model, the effective treatment effects could be conceivably exerted when a pulse current having a peak value at 1.18 kA was applied to the coil. In this case, when the peak current can be lowered, the capacitor and voltage booster circuit of a magnetic-field generating apparatus can be significantly downsized, and the cost of the system can be also significantly reduced along with that.

4 CONCLUSIONS

The present embodiment relates to development of stimulation coils for home treatment of patients of neuropathic pains by transcranial magnetic stimulation. For this purpose, a coil model having the best stimulation efficiency was obtained by numerical analysis. Then, with maintaining good stimulation efficiency, a light-weight coil model was obtained by numerical analysis. In addition, a coil model equipped with a magnetic shield for decreasing the influence on human bodies was obtained by numerical analysis. According to the above numerical analysis, the following conclusion was obtained.

4.1 In a coil model with an eccentric figure-eight-shaped coil having an XY-laminated magnetic body of 220 mm×100 mm×2 mm (X-lamination in X direction both-end parts, and Y-lamination in a central part), the induced electric field intensity in the central part of the brain model surface distant from the coil by 13 mm could be set to 507 V/m, and the stimulation efficiency could be improved by 265% as compared with the coil model with no magnetic body.

4.2 Regarding the stimulation robustness, the X-axis-direction effective stimulation distance was expanded by the shape of the magnetic body and by using ferrite in the magnetic shield. Specifically, when a Y-axis laminated magnetic body was inserted, the X-axis-direction effective stimulation distance could be increased by about two times. In addition, according to a coil model having a combination of an XY-laminated magnetic body and a magnetic shield, a home-treatment coil having stimulation robustness could be obtained which had a high misalignment permissible error with an X-axis-direction effective stimulation distance of 0.0464 m and a Y-axis-direction effective stimulation distance of 0.0629 m.

4.3 In the case of a coil model in which a box-shaped magnetic shield including a cuboid of Ni—Zn ferrite having a size of 250×150×5 mm (ceiling plate), two cuboids each having a size of 240×5×46 mm (front/rear plates), and two cuboids each having a size of 5×150×46 mm (lateral plates) covers a magnetic body (the distance to the magnetic body was 10 mm), and a flange having a width of 15 mm was attached along a lower opening edge of the box-shaped magnetic shield, then the magnetic-field intensity at a location distant by 1 m in the X+ direction was 51.4 A/m, the magnetic-field intensity at a location distant by 1 m in the X direction was 42.1 A/m, the magnetic-field intensity at a location distant by 1 m in the Y+ direction was 21.84 A/m, the magnetic-field intensity at a location distant by 0.965 m in the Y direction was 21 A/m, and the magnetic-field intensity at a location distant by 0.329 m in the Z+ direction was 21 A/m. Therefore, the coil model provided with the magnetic shield did not affect human bodies even when the human body approached to the position of 33 cm in the Z+ direction from the center of the coil and 97 cm therefrom in the Y direction.

4.4 Dimensions of Coil and Laminated Iron and Steel Plates

Figure 61:
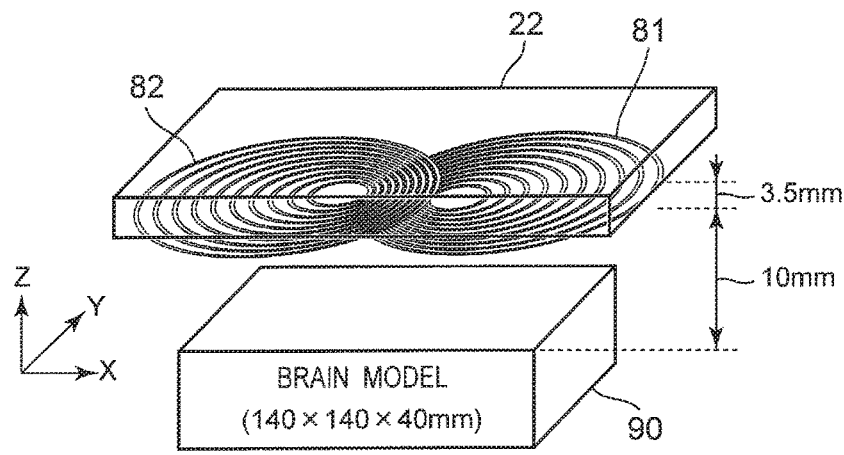
FIG. 61 is a perspective view showing a simulation model of TMS by the finite element method.

In the present embodiment, simulations were carried out on the assumption that the dimensions of the coil were as follows. An outermost diameter was 100 mm, an inner diameter was 20 mm, and the number of turns was 10. The conductive wire had a cross section of 6 mm (vertical)×2 mm (horizontal). The gap of the part at which the conductive wires became the closest to each other was 0.5 mm. The current applied to the coil was 3 kA, and a frequency was 3.15 kHz. In addition, as described below, the dimensions of the iron and steel plate were a width of 220 mm, a height of 122 mm, and a thickness of 10 mm. When the specific weight of iron was 7.85 t/m$^3$, the weight of the iron and steel plate was about 2.1 kg. The relative magnetic permeability was 5000, and electric conductivity was $1.0×10^7$ S/m and, in addition, was $1.0×10^{-7}$ S/m in the direction perpendicular to the lamination. The iron and steel plate was positioned at a location of 3.5 mm above the top surface of the central eccentric figure-eight-shaped coil. An electric conductor for simulating the brain had an electric conductivity of 0.11 S/m, and had sizes of 140 mm in vertical, 140 mm in horizontal and 40 mm in height. This electric conductor was set to be positioned at a location of 10 mm below the coil bottom surface. An entire experiment model was shown in FIG. 61. The stimulation intensity was evaluated by averaging the magnitudes of the electric field vectors of the elements which were within a radius of 10 mm from a stimulation center.

4.5 Combinations of Laminated Iron and Steel Plates in Different Directions

Figure 62:
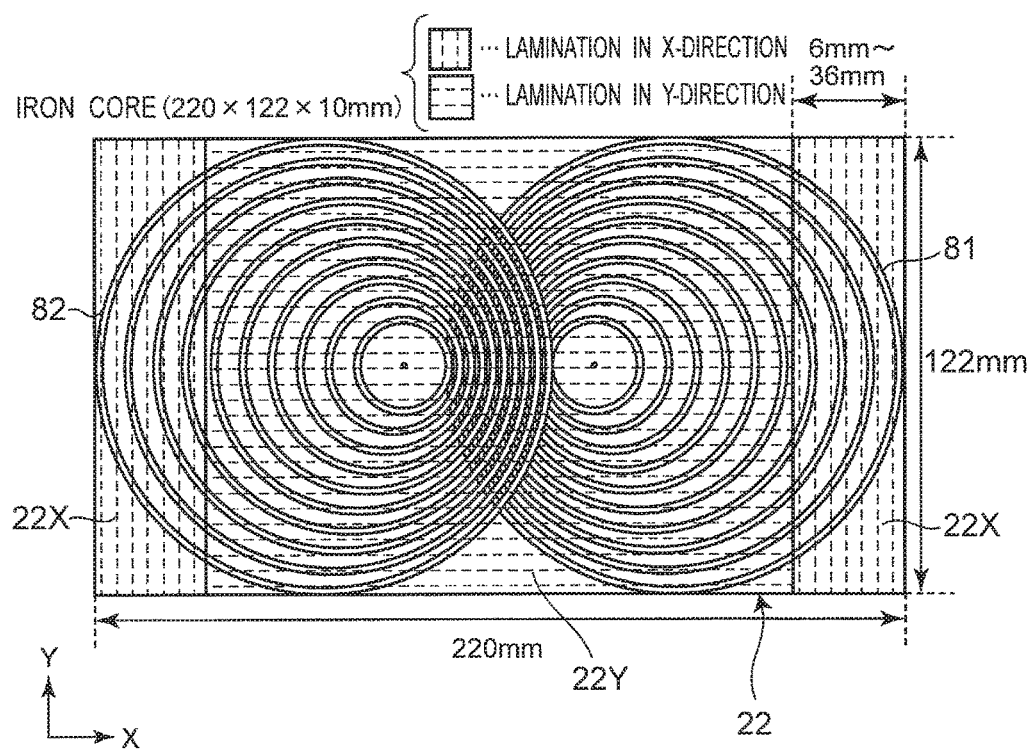
FIG. 62 is a schematic view when a laminated iron and steel plate combining vertical laminations and a horizontal lamination is positioned above a central eccentric figure-eight-shaped coil.

In order to study the optimum laminating directions of the iron and steel plates, the models were prepared in which the types of the iron and steel plates were changed without changing the appearance of the entire experiment. First of all, three types of iron and steel plates were modeled that included an iron and steel plate with no lamination, an iron and steel plate of vertical-direction lamination, and an iron and steel plate of horizontal-direction lamination. These three models were compared with the stimulation intensities of the models with no iron and steel plate. Thereafter, a model of an iron and steel plate with combining laminations in different directions was prepared in which a central part had a horizontal lamination and lateral parts had vertical lamination. The appearance of this model was shown in FIG. 62. The width of the vertically laminated part of the lateral part was changed within a range of 6 mm to 36 mm, and the relations between the width of the lateral part and the achieved average electric field intensities were plotted. In FIG. 62, 22X represents X direction laminated magnetic bodies, 22Y represents a Y direction laminated magnetic body, and the Y direction laminated magnetic body 22Y was sandwiched between a pair of X direction laminated magnetic bodies 22X in the X direction.

4.6 Influences on Stimulation Intensities by Lamination Iron and Steel Plate

Figure 63D:
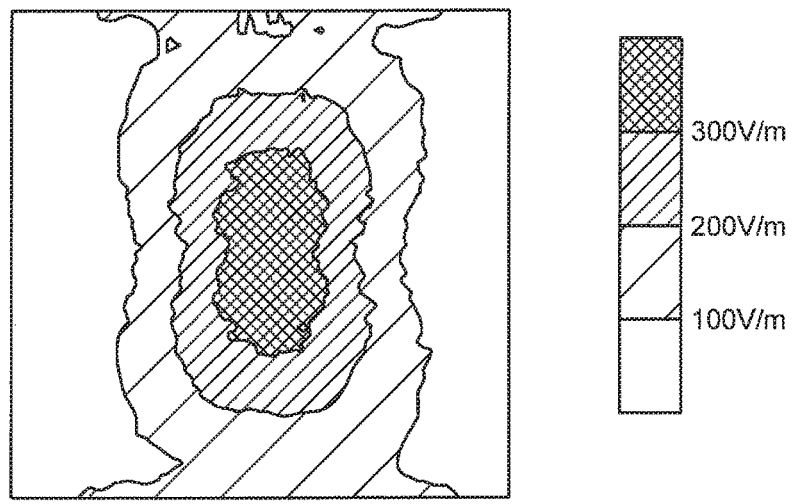
FIG. 63D is a contour graph showing an induced electric field generated at an electric conductor surface.

Referring to FIGS. 63A to 63E, the stimulation intensities (induced electric field intensities) were remarkably improved by the laminated iron and steel plates. Regarding the iron and steel plate with no lamination and the iron and steel plate with the horizontal laminate, the average electric field intensities at the centers were 218 V/m and 335 V/m, respectively (FIG. 63B and FIG. 63C). These were 1.5 times and 2.1 times of the electric field intensities of the case with no iron and steel plate (160 V/m, FIG. 63A). On the other hand, the stimulation intensity by the vertical lamination was 111 V/m (FIG. 63D), which decreased as compared with the case with no iron and steel plate.

This result indicates as a basic principle that there has been an intensity increase of the coil magnetic field because of the high magnetic permeability of the iron and steel plate. In addition, according to these results, it can be understood that there was a case in which the decreasing effect of the stimulation intensity due to the induced current loss generated in the iron and steel plate sometimes became higher than the increasing effect of the stimulation intensity by the high magnetic permeability. This bad case means the vertical lamination.

Figure 64:
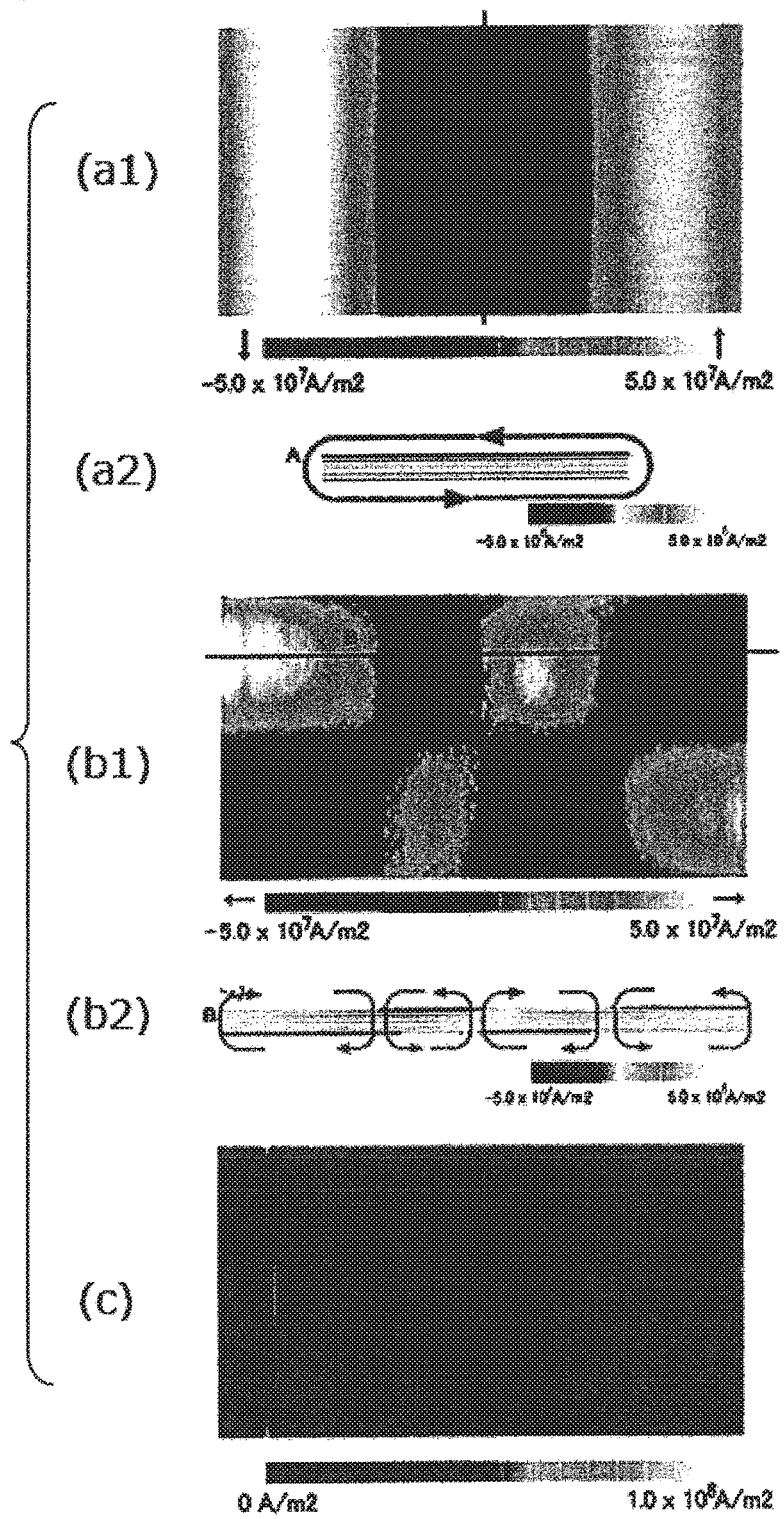
FIG. 64 shows photographic images showing induced current loss generated at iron and steel plate surfaces.

Referring to FIGS. 64 (a1) and 64 (a2), eddy currents were generated in the vertical laminated iron and steel plate by the figure-eight-shaped coil, and these induced currents have large suppressing effects against the stimulation intensities. In this case, regarding the magnetic flux generated by the coil, large current loss occurred since the cross-sectional area of the iron and steel plate became extremely large against an interlinkage magnetic flux group. In addition, also in the case of the horizontal lamination as shown in FIG. 64 (b1) and FIG. 64 (b2), it could be understood that the region where a current loss occurred was present in the iron and steel plate. Therefore, the stimulation intensity when the iron and steel plate of the horizontal lamination was used increased as compared the case with no iron and steel plate. However, a slight decrease in the stimulation intensity was expected.

Figure 63E:
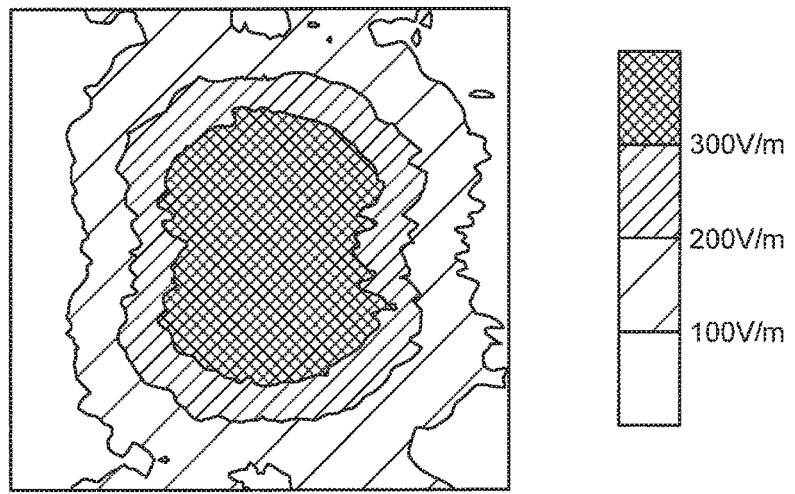
FIG. 63E is a contour graph showing an induced electric field generated at an electric conductor surface.
Figure 65:
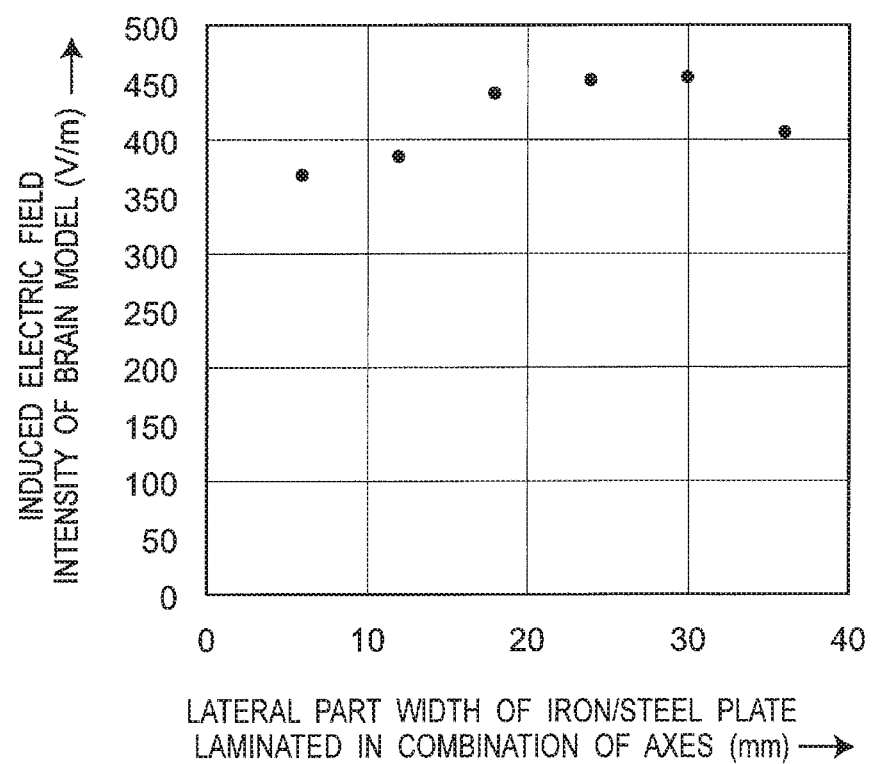
FIG. 65 is a graph showing a table showing the relations between the lateral part width of the combination-laminated iron and steel plate and the induced electric field intensities of the brain model.

4.7 about Ratio of Optimum Laminating Direction of Iron and Steel Plate in Central Eccentric Figure-Eight-Shaped Coil Referring to FIG. 63E, it was found out that the model in which the iron and steel laminates in different directions were combined was capable of achieving higher stimulation intensities than that of the iron and steel lamination in a single direction. FIG. 65 shows relations between the width of the lateral part, which was a vertical laminate, and stimulation intensities. When the lateral part width was optimized, the stimulation intensity became 456 V/m when the width was 30 mm. In addition, the inductance was 11.7

μH in the model with no iron core, and was 17.2 μH in the model with combination-laminated iron and steel plate having a width of 30 mm.

These results generally indicated that it was effective to use different lamination designs since the directions of coil magnetic fields change depending on space positions. As described above, since many lateral magnetic fields when seen from the top of the iron and steel plate were present in the central part of the iron and steel plate, it was appropriate for the direction of lamination to be also in the lateral direction. This lateral magnetic field was dominant. The region could be predicted from the fact that the highest stimulation intensity was achieved when the width of the vertical lamination was 30 mm. On the other hand, at an end of the iron and steel plate, much magnetic flux perpendicularly enters the iron and steel plate surface. Regarding such perpendicular magnetic fields, either a horizontal lamination or a vertical lamination may be used. Referring to FIG. 64C, the interruptions between the lateral lamination part and the vertical lamination parts well blocked the induced current loss generated in the iron and steel plate, and it could be understood that the combination iron and steel plate considerably suppresses induced currents as compared with the case in which the laminated iron core in a single direction was used laterally. Finally, the model in which the combination iron and steel plate was used in a combination with the central eccentric figure-eight-shaped coil achieved a stimulation intensity 2.8 times that of the case with no iron and steel plate and, in addition, achieved a stimulation intensity 3.4 times that of a normal figure-eight-shaped coil with no iron core.

On the other hand, when the iron and steel plate was used in combination, the value of inductance somewhat increased as compared with the case in which no iron and steel plate was used. Therefore, somewhat changes in the frequency of stimulation pulses of TMS were expected. However, the inductance of a TMS coil typically had a value of 10 μH to 35 μH, and it was conceived that these inductance changes could be handled by appropriately selecting a circuit having a capacitor of an appropriate value. In addition, in recent years, a circuit capable of generating pulses of free shapes regardless of inductance values was studied, and it was conceived that using such a circuit will eliminate the necessity of considering the inductance changes.

As a final conclusion, the iron and steel plate in which the horizontal lamination and the vertical lamination were combined was extremely effective for improving stimulation intensity, and it was found out that the intensity thereof became 2.8 times as compared with the case in which no iron and steel plate was used. Such a result indicates that it was important to determine the lamination direction of the iron and steel plate in consideration of the directions of magnetic fields generated by the TMS coil. By using the laminated iron and steel plate, the current applied to the coil 8 could be decreased, and, as a result, the heat of the coil 8 could be reduced without using a heat removing mechanism. By virtue of this, high-output and high-frequency rTMS treatment was possible, and TMS equipment itself could be created in a smaller size with a lower cost.

As described above, the coil in which the eccentric figure-eight-shaped coil 8 is combined with the magnetic body 22 and the magnetic shield 91 is sufficiently usable as a coil for a home magnetic stimulation apparatus.

INDUSTRIAL APPLICABILITY

As described above, according to the present invention, a coil apparatus and a transcranial magnetic stimulation apparatus having the coil apparatus can be provided, which are capable of (a) generating a higher induced electric field intensity in a magnetic stimulation-target region of the brain than that of the conventional techniques, (b) having more robustness than that of the conventional techniques, and (c) being used, for example, in a home magnetic stimulation apparatus.

According to one aspect of the present invention, there is provided a coil apparatus for use in a transcranial magnetic stimulation apparatus, where the coil apparatus includes a coil arranged to oppose a surface of a head of a human to generate a current by an induced electric field in a magnetic stimulation-target region in a brain by electromagnetic induction, and to stimulate neurons. The coil apparatus includes the coil configured by winding a conductive wire along a predetermined reference surface; and a magnetic body arranged between the head and the coil to oppose the coil, and arranged at a position at an opposite side of the head. The magnetic body is provided for flowing a current therein by an induced electric field when the coil is driven, and for increasing the current flowing by the induced electric field in a magnetic stimulation-target region of the brain as compared with that with no magnetic body. Therefore, according to the present invention, the present invention is capable of generating a higher induced electric field intensity with than that of the magnetic stimulation-target region of the brain than that of the conventional techniques, having more robustness than that of the conventional techniques, and being used, for example, in a home magnetic stimulation apparatus. Further, when the magnetic body is configured by laminating in the winding direction of the coil, the current caused by the induced electric field flowing in the magnetic stimulation-target region of the brain can further increase.

DESCRIPTION OF REFERENCE CHARACTERS

1: TRANSCRANIAL MAGNETIC STIMULATION APPARATUS
4: MAGNETIC STIMULATION APPARATUS
5: COIL APPARATUS
6: CONTROL UNIT
8: COIL
8L: CENTRAL AXIS
9: CASING
22, 22A TO 22H: MAGNETIC BODIES
25: COIL DRIVE CIRCUIT
26: CABLE
31: THYRISTOR
31D: DIODE
61: ALTERNATING-CURRENT POWER SUPPLY
62: POWER SUPPLY CIRCUIT
63: VOLTAGE BOOSTER CIRCUIT
64: CAPACITOR
65: RESISTOR
66: SEMICONDUCTOR SWITCH
67: CONTROL CIRCUIT
80: CONDUCTIVE WIRE
81, 82: COIL PARTS
83, 84: CENTERS OF COIL PARTS
85: CENTRAL PART OF COIL
90: BRAIN MODEL
91, 91A, 91B: MAGNETIC SHIELDS
91F: FLANGE
100A TO 100D: MAGNETIC BODIES

REFERENCE DOCUMENTS

[1] MOUCHAWAR G A, NYENHUIS J A, BOURLAND J D, GEDDES L A, "GUIDELINES OR ENERGY-EFFI-

CIENT COILS-COILS DESIGNED FOR MAGNETIC STIMULATION OF THE HEART", ELECTROENCEPHALOGRAPHY AND CLINICAL NEUROPHYSIOLOGY, pp. 255-267, Supplement: Suppl. 43, Published in 1991

[2] JALINOUS, R., "TECHNICAL AND PRACTICAL ASPECTS OF MAGNETIC NERVE-STIMULATION", JOURNAL OF CLINICAL NEUROPHYSIOLOGY, Vol. 8, Issue 1, pp. 10-25, Published in January 1991

[3] Taishi Fukushima, Atsushi Nishikawa, Fumio Miyazaki, Masaki Sekino, Yoshihiro Yasumuro, Taiga Matsuzaki, Koichi Hosomi, Youichi Saitoh "The Development of Magnetic Navigation System for Home Use of Repetitive Transcranial Magnetic Stimulation", Biomedical Engineering, Vol. 49, pp. 122 to 131, (2011)

[4] Xu G, Chen Y, Yang S, Wang M, Yan W, "The optimal design of magnetic coil in transcranial magnetic stimulation", Conference Proceeding of IEEE Engineering Medical Biology Society, June 2005: 6221-4.

[5] Roth Y, Zangen A, Hallett M, "A coil design for transcranial magnetic stimulation of deep brain regions", Journal of Clinical Neurophysiology, August 2002, 19(4), 361-70.

[6] Lin V W, Hsiao I N, Dhaka V, "Magnetic coil design considerations for functional magnetic stimulation", IEEE Transaction on Biomedical Engineering, May 2000, 47(5), 600-10.

[7] Zimmermann K P, Simpson R K, "Slinky coils for neuromagnetic stimulation", Electroencephalogram Clinical Neurophysiology, April 1996, 101(2), 145-52

[8] Ren C, Tarjan P P, Popovic D B, "A novel electric design for electromagnetic stimulation—the Slinky coil", IEEE Transaction on Biomedical Engineering, September 1995, 42(9), 918-25

[9] Lee C (Lee, Chany), Im C H (Im, Chang-Hwan), Jung H K (Jung, Hyun-Kyo), "Analysis and design of whole-head magnetic brain stimulators: A simulation study", INTERNATIONAL JOURNAL OF CONTROL AUTOMATION AND SYSTEMS, Vol. 5, Issue 3, pp. 337-342, Published in June 2007

[10] Chang-Hwan Im; Chany Lee; "Computer-Aided Performance Evaluation of a Multichannel Transcranial Magnetic Stimulation System Magnetics", IEEE Transactions on Magnetics, Vol. 42, Issue 12, December 2006, pp. 3803-3808

[11] Ruohonen J, Ravazzani P, Grandori F, "Functional magnetic stimulation: theory and coil optimization", BIOELECTROCHEMISTRY AND BIOENERGETICS, Vol. 47 Issue 2, pp. 213-219, Published in 1998

[12] Onuki, T; Wakao, S; Miyokawa, T, et al., "Design optimization of stimulation coil system for nerve stimulation", IEEE TRANSACTIONS ON MAGNETICS, Vol. 34, Issue 4, pp. 2159-2161, Published in 1998

[13] GRANDORI F, RAVAZZANI P, "MAGNETIC STIMULATION OF THE MOTOR CORTEX-THEORETICAL CONSIDERATIONS", IEEE TRANSACTIONS ON BIOMEDICAL ENGINEERING, Vol. 38, Issue 2, pp. 180-191, Published in February 1991

[14] COHEN L G, ROTH B J, NILSSON J, et al., "EFFECTS OF COIL DESIGN ON DELIVERY OF FOCAL MAGNETIC STIMULATION-TECHNICAL CONSIDERATIONS", ELECTROENCEPHALOGRAPHY AND CLINICAL NEUROPHYSIOLOGY, Vol. 75, Issue 4, pp. 350-357, Published in April 1990

[15] Masaki Sekino, Takuya Kato and Hiroyuki Ohsaki, "Eccentric Figure-Eight Magnetic Stimulator Coils", Complex Medical Engineering (CME), 2012 ICME, International Conference on, pp. 728-733, 1-4, July 2012

Figure 8:
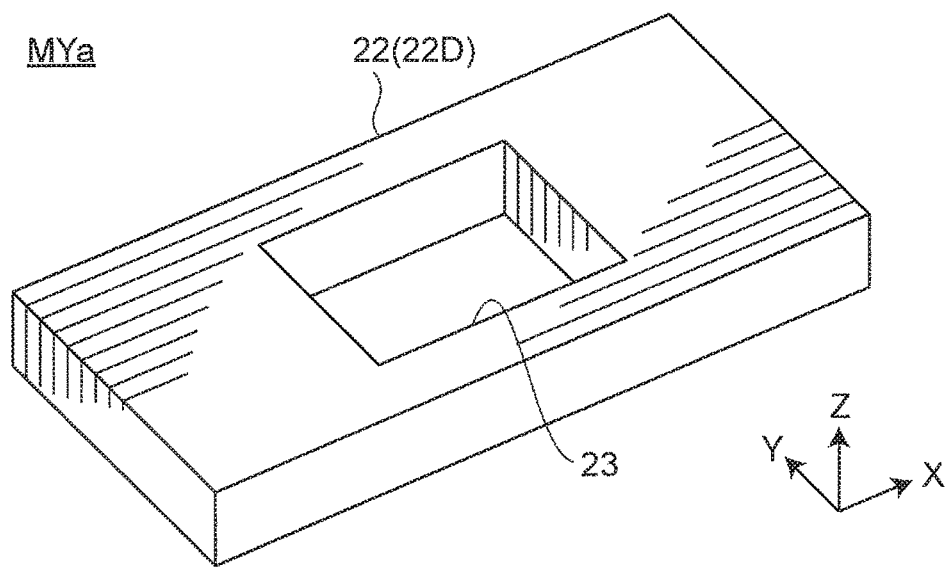
FIG. 8 is a perspective view of a rectangular-frame-shaped magnetic body which is obtained by laminating magnetic steel sheets in the Y direction and has a cubic shape.
Figure 9:
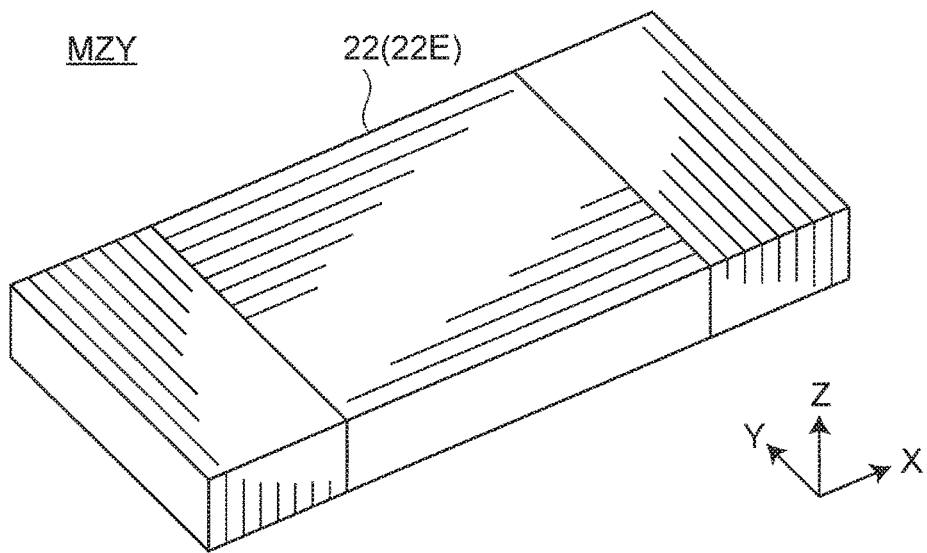
FIG. 9 is a perspective view of a non-rectangular-frame-shaped magnetic body which is obtained by laminating magnetic steel sheets in the X and Y directions and has a cubic shape.
Figure 10:
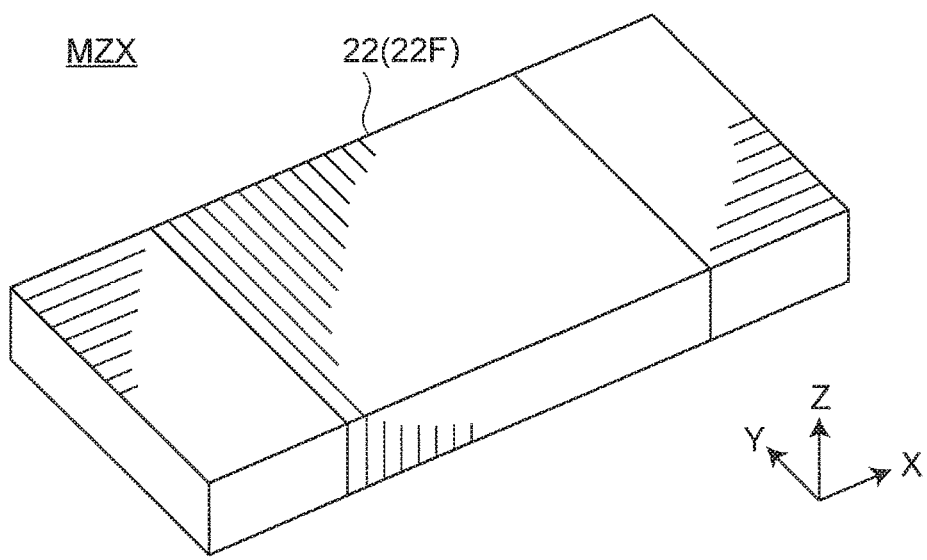
FIG. 10 is a perspective view of a non-rectangular-frame-shaped magnetic body which is obtained by laminating magnetic steel sheets in the X and Y directions and has a cubic shape.
Figure 11:
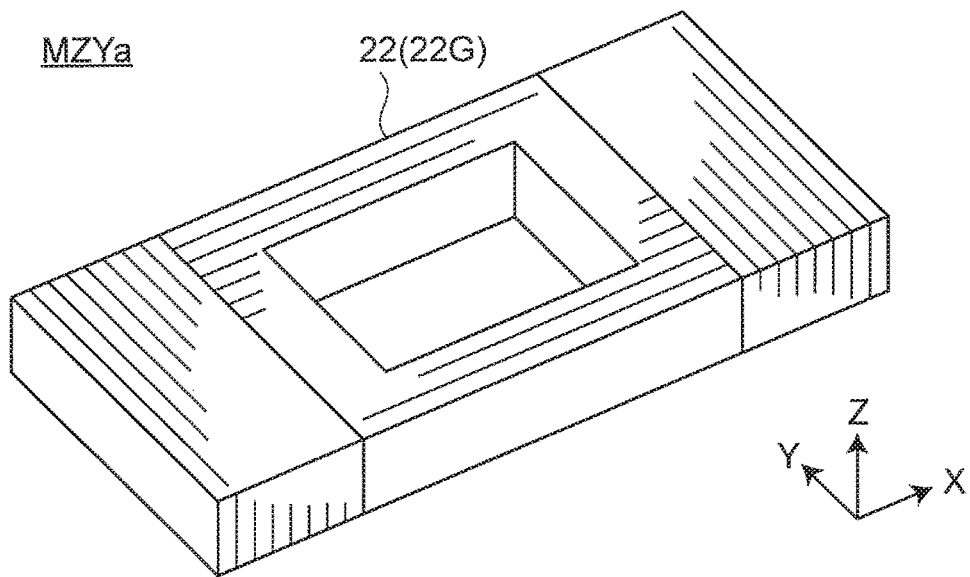
FIG. 11 is a perspective view of a rectangular-frame-shaped magnetic body which is obtained by laminating magnetic steel sheets in the X and Y directions and has a cubic shape.
Figure 12:
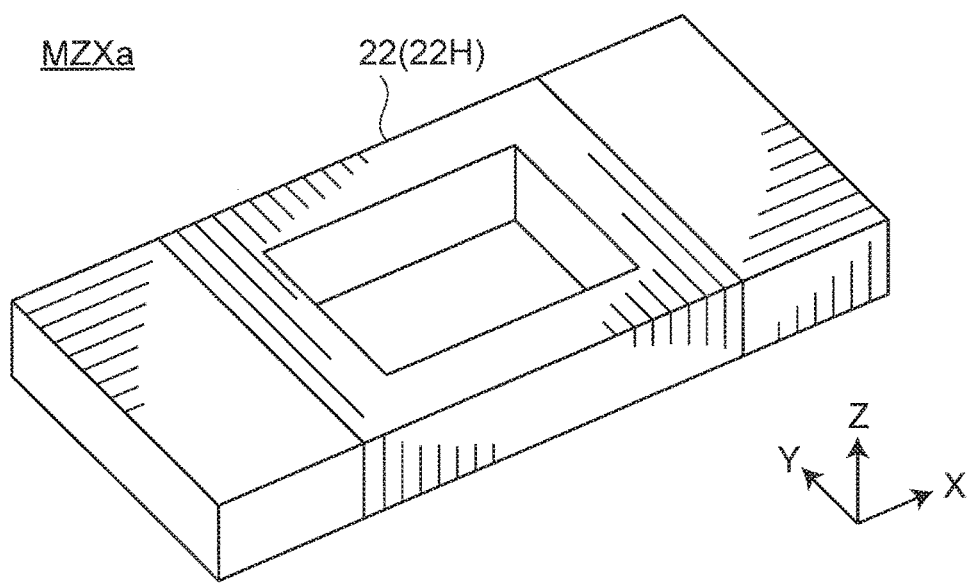
FIG. 12 is a perspective view of a rectangular-frame-shaped magnetic body which is obtained by laminating magnetic steel sheets in the X and Y directions and has a cubic shape.
Figure 13:
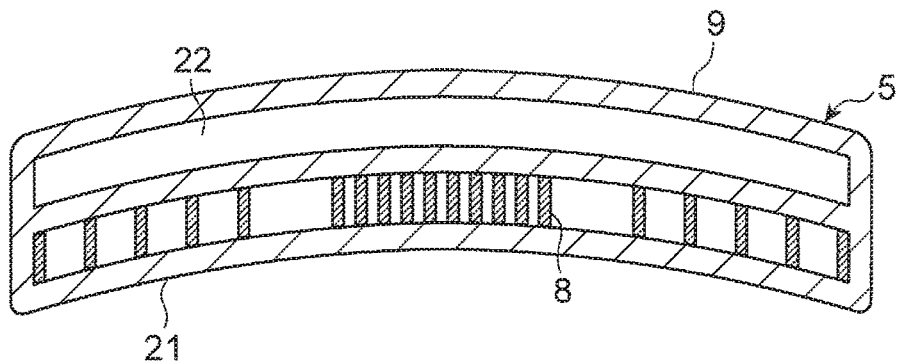
FIG. 13 is a cross-sectional view of a coil apparatus incorporating a curved-surface-type coil (of non-overlapping type) and a magnetic body in a casing having a curved surface as a bottom surface.
Figure 14:
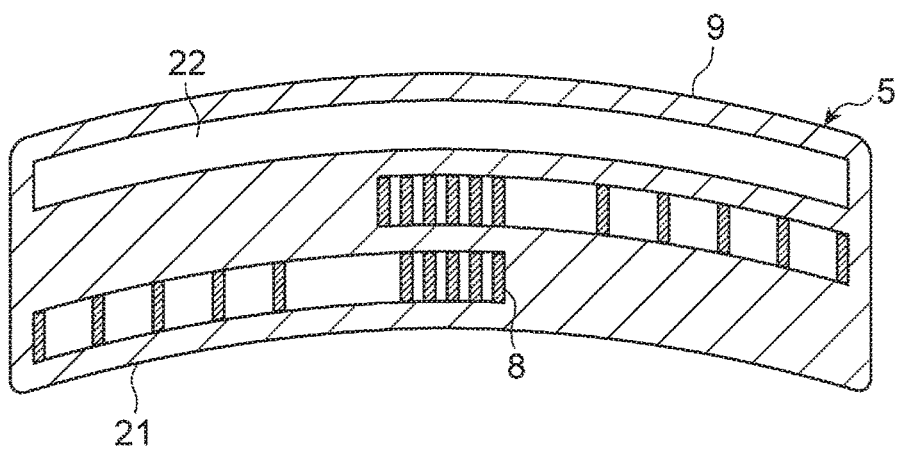
FIG. 14 is a cross-sectional view of a coil apparatus incorporating a curved-surface-type coil (of overlapping type) and a magnetic body in a casing having a curved surface as a bottom surface.
Figure 15:
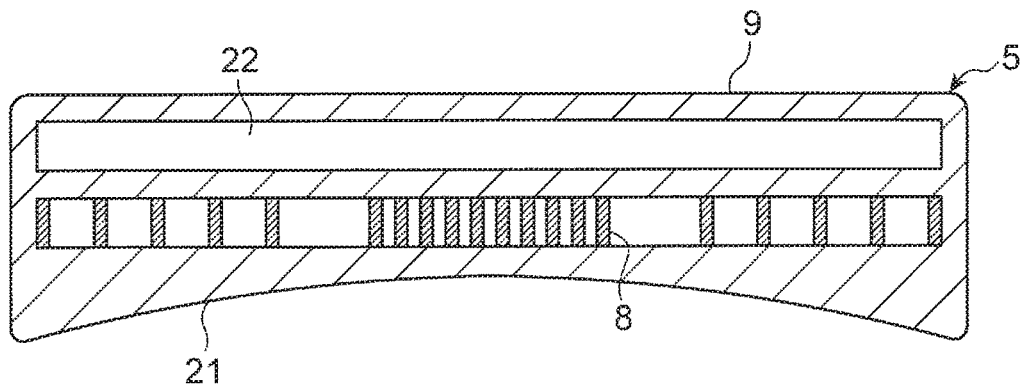
FIG. 15 is a cross-sectional view of a coil apparatus incorporating a flat coil (of non-overlapping type) and a magnetic body in a casing having a curved surface as a bottom surface.
Figure 16:
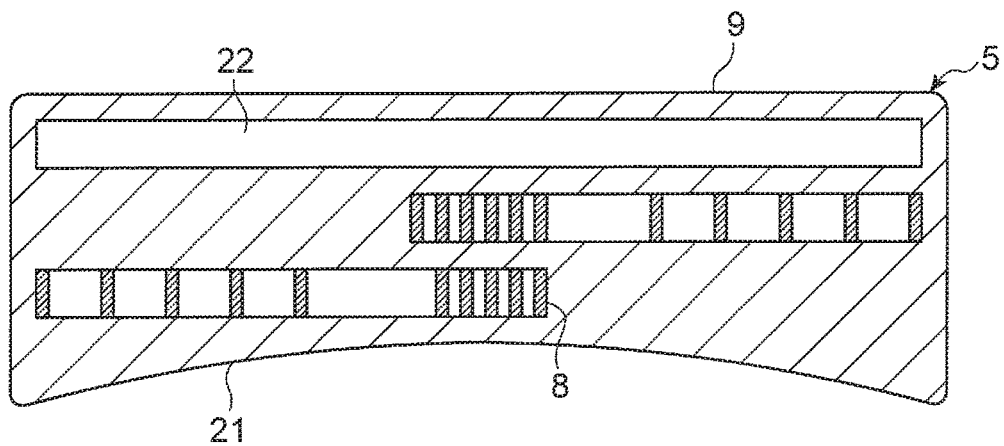
FIG. 16 is a cross-sectional view of a coil apparatus incorporating a flat coil (of overlapping type) and a magnetic body in a casing having a curved surface as a bottom surface.

[16] Thielscher A, Kammer T, "Electric field properties of two commercial figure-8 coils in TMS: calculation of focality and efficiency", Clinical Neurophysiology, July 2004, 115 (7), 1697-708

[17] Feitosa M, Fontana E, "Generalized series solution for the induced E-field distribution of slinky-type magnetic stimulators", Conference Proceedings of IEEE Engineering Medical Biology Society, 2006, 1:4655-8

[18] Ravazzani P, Ruohonen J, Tognola G, Anfosso F, O Ilikainen M, Ilmoniemi R J, Grandori F, "Frequency-related effects in the optimization of coils for the magnetic stimulation of the nervous system", IEEE Transactions on Biomedical Engendering, May 2002, 49(5):463-71

[19] Salvador R, Miranda P C, Roth Y, Zangen A, "High permeability cores to optimize the stimulation of deeply located brain regions using transcranial magnetic stimulation", Physics in Medical Biology, May 21, 2009; 54(10):3113-28

[20] Han B H, Lee S Y, Kim J H, Yi J H, "Some technical aspects of magnetic stimulation coil design with the ferromagnetic effect", Medical and Biology Engineering and Computing, September 2003, 41(5):516-8

[21] Epstein C M, Davey K R, "Iron-core coils for transcranial magnetic stimulation", Journal of Clinical Neurophysiology, August 2002, 19(4):376-81.

[22] Roth Y, Amir A, Levkovitz Y, Zangen A, "Three-dimensional distribution of the electric field induced in the brain by transcranial magnetic stimulation using figure-8 and deep H-coils", Journal of Clinical Neurophysiology, February 2007, 24(1):31-8

[23] Boroojerdi B, Foltys H, Krings T, Spetzger U, Thron A, Topper R, "Localization of the motor hand area using transcranial magnetic stimulation and functional magnetic resonance imaging", Clinical Neurophysiology, Vol. 110, pp. 699-704, (1996)

[24] Sekino M, Ueno S, "FEM-based determination of optimum current distribution in transcranial magnetic stimulation as an alternative to electroconvulsive therapy", IEEE Transactions on Magnetics, Vol. 40, pp. 2167-2169

[25] Tsuyama S, Katayama Y, Hyodo A, Hayami T, Ueno S, Iramina K, "Effects of coil parameters on the stimulated area by transcranial magnetic stimulation", IEEE Transactions on Magnetics, Vol. 45, pp. 4845-4848, (2009)

[26] Sekino M, Hirata M, Sakihara K, Yoorifuji S, Ueno S, "Intensity and localization of eddy currents in transcranial magnetic stimulation to cerebellum", IEEE Transactions on Magnetics Vol. 42, pp. 3575-3577, (2006)

[27] PHOTON Co., Ltd., "PHOT-SERIES EDDY ver7.2 64 bit"

[28] Web site of PHOTON Co., Ltd., "Electromagnetic Field Analysis WAVEjw", the Internet [searched on March 17, H28 (2016)] <URL> http://www.photon-cae.co.jp/product/series/index.html

The invention claimed is:

1. A coil apparatus for use in a transcranial magnetic stimulation apparatus, the coil apparatus comprising a coil arranged to oppose a surface of a head of a human to generate a current by an induced electric field in a magnetic stimulation-target region in a brain by electromagnetic induction, and to stimulate neurons, the coil apparatus comprising:

the coil configured by winding a conductive wire along a predetermined reference surface; and a magnetic body arranged between the head and the coil to oppose the coil, and arranged at a position at an opposite side of the head,
wherein the magnetic body is provided for flowing a current therein by an induced electric field when the coil is driven, and for increasing the current flowing by the induced electric field in a magnetic stimulation-target region of the brain as compared with that with no magnetic body, and
wherein the magnetic body is configured by laminating respective lamination plates configuring the magnetic body, in a lamination direction of respective turn winding wires of the coil.

2. A coil apparatus for use in a transcranial magnetic stimulation apparatus, the coil apparatus comprising a coil arranged to oppose a surface of a head of a human to generate a current by an induced electric field in a magnetic stimulation-target region in a brain by electromagnetic induction, and to stimulate neurons, the coil apparatus comprising:
the coil configured by winding a conductive wire along a predetermined reference surface; and
a magnetic body arranged between the head and the coil to oppose the coil, and arranged at a position at an opposite side of the head,
wherein the magnetic body is provided for flowing a current therein by an induced electric field when the coil is driven, and for increasing the current flowing by the induced electric field in a magnetic stimulation-target region of the brain as compared with that with no magnetic body,
wherein the coil is one of a non-eccentric figure-eight-shaped spiral coil having two coil parts, and an eccentric figure-eight-shaped spiral coil having two coil parts, and
wherein, when a direction of a line connecting centers of the two coil parts along the reference surface is defined as a first direction, and when a direction orthogonal to the first direction along the reference surface is defined as a second direction, the magnetic body is configured by laminating a plurality of magnetic steel sheets in one of the first direction and the second direction.

3. A coil apparatus for use in a transcranial magnetic stimulation apparatus, the coil apparatus comprising a coil arranged to oppose a surface of a head of a human to generate a current by an induced electric field in a magnetic stimulation-target region in a brain by electromagnetic induction, and to stimulate neurons, the coil apparatus comprising:
the coil configured by winding a conductive wire along a predetermined reference surface; and
a magnetic body arranged between the head and the coil to oppose the coil, and arranged at a position at an opposite side of the head,
wherein the magnetic body is provided for flowing a current therein by an induced electric field when the coil is driven, and for increasing the current flowing by the induced electric field in a magnetic stimulation-target region of the brain as compared with that with no magnetic body,
wherein the coil is one of a non-eccentric figure-eight-shaped spiral coil having two coil parts, and an eccentric figure-eight-shaped spiral coil having two coil parts, and
wherein, when a direction of a line connecting centers of the two coil parts along the reference surface is defined as a first direction, and when a direction orthogonal to the first direction along the reference surface is defined as a second direction, the magnetic body is configured to include:
a first laminated magnetic body part configured by laminating a plurality of magnetic steel sheets in the first direction; and
a second laminated magnetic body part configured by laminating a plurality of magnetic steel sheets in the second direction.

4. The coil apparatus for use in the transcranial magnetic stimulation apparatus as claimed in claim 3,
wherein the magnetic body includes:
one of the second laminated magnetic body part; and
a pair of the first laminated magnetic body parts,
wherein the second laminated magnetic body part is provided between the pair of first laminated magnetic body parts in the first direction.

5. The coil apparatus for use in the transcranial magnetic stimulation apparatus as claimed in claim 1,
wherein the reference surface is a plane, a curved surface, or a spherical surface.

6. The coil apparatus for use in the transcranial magnetic stimulation apparatus as claimed in claim 1,
wherein the coil is one of a non-eccentric spiral coil and an eccentric spiral coil.

7. The coil apparatus for use in the transcranial magnetic stimulation apparatus as claimed in claim 1,
wherein the coil is one of a non-eccentric figure-eight-shaped spiral coil having two coil parts, and an eccentric figure-eight-shaped spiral coil having two coil parts.

8. The coil apparatus for the transcranial magnetic stimulation apparatus as claimed in claim 1,
wherein the coil is a dome-shaped coil.

9. The coil apparatus for use in the transcranial magnetic stimulation apparatus as claimed in claim 2,
wherein the magnetic body has a shape of one of tetragonal shape, polygonal shape, circular shape, elliptical shape, and oblong shape when seen from a third direction orthogonal to the first direction and the second direction.

10. The coil apparatus for use in the transcranial magnetic stimulation apparatus as claimed in claim 2,
wherein the magnetic body includes an opening at a center when seen from a third direction orthogonal to the first direction and the second direction.

11. A transcranial magnetic stimulation apparatus comprising a coil apparatus and a control unit for generating dynamic magnetic fields for application to a brain of a human by means of the coil apparatus,
wherein the coil apparatus comprises a coil arranged to oppose a surface of a head of a human to generate a current by an induced electric field in a magnetic stimulation-target region in a brain by electromagnetic induction, and to stimulate neurons,
wherein the coil apparatus comprises:
the coil configured by winding a conductive wire along a predetermined reference surface; and
a magnetic body arranged between the head and the coil to oppose the coil, and arranged at a position at an opposite side of the head, and
wherein the magnetic body is provided for flowing a current therein by an induced electric field when the coil is driven, and for increasing the current flowing by the induced electric field in a magnetic stimulation-target region of the brain as compared with that with no magnetic body, and wherein the magnetic body is configured by laminating respective lamination plates configuring the magnetic body, in a lamination direction of respective turn winding wires of the coil.

12. A transcranial magnetic stimulation apparatus comprising a coil apparatus and a control unit for generating dynamic magnetic fields for application to a brain of a human by means of the coil apparatus,
wherein the coil apparatus comprises a coil arranged to oppose a surface of a head of a human to generate a current by an induced electric field in a magnetic stimulation-target region in a brain by electromagnetic induction, and to stimulate neurons,
wherein the coil apparatus comprises:
the coil configured by winding a conductive wire along a predetermined reference surface; and
a magnetic body arranged between the head and the coil to oppose the coil, and arranged at a position at an opposite side of the head, and
wherein the magnetic body is provided for flowing a current therein by an induced electric field when the coil is driven, and for increasing the current flowing by the induced electric field in a magnetic stimulation-target region of the brain as compared with that with no magnetic body,
wherein the coil is one of a non-eccentric figure-eight-shaped spiral coil having two coil parts, and an eccentric figure-eight-shaped spiral coil having two coil parts, and
wherein, when a direction of a line connecting centers of the two coil parts along the reference surface is defined as a first direction, and when a direction orthogonal to the first direction along the reference surface is defined as a second direction, the magnetic body is configured by laminating a plurality of magnetic steel sheets in one of the first direction and the second direction.

13. A transcranial magnetic stimulation apparatus comprising a coil apparatus and a control unit for generating dynamic magnetic fields for application to a brain of a human by means of the coil apparatus,
wherein the coil apparatus comprises a coil arranged to oppose a surface of a head of a human to generate a current by an induced electric field in a magnetic stimulation-target region in a brain by electromagnetic induction, and to stimulate neurons,
wherein the coil apparatus comprises:
the coil configured by winding a conductive wire along a predetermined reference surface; and
a magnetic body arranged between the head and the coil to oppose the coil, and arranged at a position at an opposite side of the head, and
wherein the magnetic body is provided for flowing a current therein by an induced electric field when the coil is driven, and for increasing the current flowing by the induced electric field in a magnetic stimulation-target region of the brain as compared with that with no magnetic body,
wherein the coil is one of a non-eccentric figure-eight-shaped spiral coil having two coil parts, and an eccentric figure-eight-shaped spiral coil having two coil parts, and
wherein, when a direction of a line connecting centers of the two coil parts along the reference surface is defined as a first direction, and when a direction orthogonal to the first direction along the reference surface is defined as a second direction, the magnetic body is configured to include:
a first laminated magnetic body part configured by laminating a plurality of magnetic steel sheets in the first direction; and
a second laminated magnetic body part configured by laminating a plurality of magnetic steel sheets in the second direction.

* * * * *